US010575893B2

(12) United States Patent
Mayse

(10) Patent No.: US 10,575,893 B2
(45) Date of Patent: Mar. 3, 2020

(54) SYSTEM AND METHOD FOR PULMONARY TREATMENT

(71) Applicant: Holaira, Inc., Plymouth, MN (US)

(72) Inventor: Martin L. Mayse, Wayzata, MN (US)

(73) Assignee: Nuvaira, Inc., Plymouth, MN (US)

( * ) Notice: Subject to any disclaimer, the term of this patent is extended or adjusted under 35 U.S.C. 154(b) by 0 days.

(21) Appl. No.: 15/177,012

(22) Filed: Jun. 8, 2016

(65) Prior Publication Data
US 2016/0278845 A1 Sep. 29, 2016

Related U.S. Application Data

(63) Continuation-in-part of application No. 13/081,406, filed on Apr. 6, 2011.
(Continued)

(51) Int. Cl.
*A61B 18/14* (2006.01)
*A61B 18/12* (2006.01)
(Continued)

(52) U.S. Cl.
CPC ........ *A61B 18/14* (2013.01); *A61B 17/12104* (2013.01); *A61B 18/12* (2013.01);
(Continued)

(58) Field of Classification Search
CPC .............. A61N 1/3601; A61N 1/36053; A61N 1/3606; A61N 1/3605; A61N 1/05; A61N 1/0519; A61N 1/36; A61B 18/1492; A61B 2018/00541; A61B 2018/00434; A61B 5/4836; A61B 2018/1861; A61B 18/12;
(Continued)

(56) References Cited

U.S. PATENT DOCUMENTS

| 6,547,776 B1 * | 4/2003 | Gaiser ................... A61M 29/02 604/103.02 |
| 7,371,231 B2 | 5/2008 | Rioiux et al. |

(Continued)

OTHER PUBLICATIONS

Office Action dated Nov. 22, 2016 for Canadian Application No. 2,795,564, 4 pages.
(Continued)

*Primary Examiner* — Deborah L Malamud
(74) *Attorney, Agent, or Firm* — Patterson Thuente Pedersen, P.A.

(57) ABSTRACT

Devices and methods for treating one or more pulmonary diseases while avoiding or minimizing injury to the esophagus and branches of the vagus nerve that run along the outside of the esophagus. The device includes at least one energy delivery element disposed on an elongate member and a means for protecting the esophagus and surrounding tissues, such as esophageal branches of the vagus nerve, during treatment. The energy delivery element is positionable to target at least one nerve in or around the tracheal wall when the elongate member is positioned in the trachea. Energy from the energy delivery element is delivered to the at least one nerve to treat pulmonary symptoms, conditions, and/or diseases, such as asthma, COPD, obstructive lung diseases, or other pulmonary diseases, while the protection means protects the esophagus and surrounding tissues from permanent damage.

12 Claims, 55 Drawing Sheets

Related U.S. Application Data

(60) Provisional application No. 61/321,346, filed on Apr. 6, 2010.

(51) Int. Cl.
| | | |
|---|---|---|
| *A61B 18/18* | (2006.01) | |
| *A61B 17/12* | (2006.01) | |
| *A61B 18/00* | (2006.01) | |
| *A61B 18/16* | (2006.01) | |
| *A61B 90/00* | (2016.01) | |
| *A61B 18/24* | (2006.01) | |
| *A61B 18/02* | (2006.01) | |
| *A61B 17/00* | (2006.01) | |

(52) U.S. Cl.
CPC ...... *A61B 18/1815* (2013.01); *A61B 17/1204* (2013.01); *A61B 17/12136* (2013.01); *A61B 18/1492* (2013.01); *A61B 18/24* (2013.01); *A61B 2017/00022* (2013.01); *A61B 2017/00026* (2013.01); *A61B 2017/00084* (2013.01); *A61B 2017/00867* (2013.01); *A61B 2018/00005* (2013.01); *A61B 2018/00017* (2013.01); *A61B 2018/0022* (2013.01); *A61B 2018/00023* (2013.01); *A61B 2018/00136* (2013.01); *A61B 2018/00148* (2013.01); *A61B 2018/00267* (2013.01); *A61B 2018/00297* (2013.01); *A61B 2018/00434* (2013.01); *A61B 2018/00488* (2013.01); *A61B 2018/00541* (2013.01); *A61B 2018/00577* (2013.01); *A61B 2018/00642* (2013.01); *A61B 2018/00666* (2013.01); *A61B 2018/00714* (2013.01); *A61B 2018/00821* (2013.01); *A61B 2018/00875* (2013.01); *A61B 2018/0262* (2013.01); *A61B 2018/147* (2013.01); *A61B 2018/1465* (2013.01); *A61B 2018/162* (2013.01); *A61B 2018/1861* (2013.01); *A61B 2090/0481* (2016.02); *A61B 2090/065* (2016.02)

(58) Field of Classification Search
CPC ... A61B 5/686; A61B 18/082; A61B 18/1206; A61B 18/14; A61B 2018/00488
See application file for complete search history.

(56) References Cited

U.S. PATENT DOCUMENTS

| | | |
|---|---|---|
| 7,608,275 B2 | 10/2009 | Deem et al. |
| 8,088,127 B2 | 1/2012 | Mayse et al. |
| 8,133,497 B2 | 3/2012 | Deem et al. |
| 8,172,827 B2 | 5/2012 | Deem et al. |
| 8,226,638 B2 | 7/2012 | Mayse et al. |
| 8,338,164 B2 | 12/2012 | Deem et al. |
| 8,483,831 B1 | 7/2013 | Hlavka et al. |
| 8,489,192 B1 | 7/2013 | Hlavka et al. |
| 8,731,672 B2 | 5/2014 | Hlavka et al. |
| 8,740,895 B2 | 6/2014 | Mayse et al. |
| 8,777,943 B2 | 7/2014 | Mayse et al. |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,507 B2 | 2/2015 | Mayse et al. |
| 8,961,508 B2 | 2/2015 | Mayse et al. |
| 9,005,195 B2 | 4/2015 | Mayse et al. |
| 9,017,324 B2 | 4/2015 | Mayse et al. |
| 9,125,643 B2 | 9/2015 | Hlavka et al. |
| 9,149,328 B2 | 10/2015 | Dimmer et al. |
| 9,339,618 B2 | 5/2016 | Deem et al. |
| 9,398,933 B2 | 7/2016 | Mayse |
| 2003/0060813 A1 | 3/2003 | Loeb et al. |
| 2003/0159700 A1 | 8/2003 | Laufer et al. |
| 2004/0226556 A1 | 11/2004 | Deem et al. |
| 2005/0182393 A1 | 8/2005 | Abboud et al. |
| 2006/0225742 A1 | 10/2006 | Deem et al. |
| 2007/0055328 A1 | 3/2007 | Mayse et al. |
| 2007/0100390 A1 | 5/2007 | Danaek et al. |
| 2007/0106292 A1 | 5/2007 | Kaplan et al. |
| 2007/0106339 A1* | 5/2007 | Errico ............... A61N 1/3601 607/42 |
| 2008/0039746 A1* | 2/2008 | Hissong ............. A61N 7/022 601/3 |
| 2008/0161890 A1 | 7/2008 | Lafontaine |
| 2008/0243112 A1 | 10/2008 | De Neve |
| 2009/0018538 A1 | 1/2009 | Webster et al. |
| 2009/0043301 A1 | 2/2009 | Jarrard |
| 2009/0306644 A1 | 12/2009 | Mayse et al. |
| 2011/0118725 A1 | 5/2011 | Mayse et al. |
| 2011/0152855 A1 | 6/2011 | Mayse et al. |
| 2011/0257647 A1 | 10/2011 | Mayse et al. |
| 2011/0301587 A1 | 12/2011 | Deem et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0203216 A1 | 8/2012 | Mayse et al. |
| 2012/0203222 A1 | 8/2012 | Mayse et al. |
| 2012/0209261 A1 | 8/2012 | Mayse et al. |
| 2012/0209296 A1 | 8/2012 | Mayse et al. |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0186341 A1 | 7/2014 | Mayse |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2015/0051597 A1 | 2/2015 | Mayse et al. |
| 2015/0141985 A1 | 5/2015 | Mayse et al. |
| 2015/0150625 A1 | 6/2015 | Deem et al. |
| 2015/0190193 A1 | 7/2015 | Mayse et al. |
| 2015/0366603 A1 | 12/2015 | Hlavka et al. |
| 2016/0022351 A1 | 1/2016 | Kaveckis et al. |
| 2016/0038725 A1 | 2/2016 | Mayse et al. |
| 2016/0192981 A1 | 7/2016 | Dimmer et al. |

OTHER PUBLICATIONS

Office Action dated Jun. 2, 2017 for Chinese Application No. 201510154983.9, 9 pages.

Communication dated May 2, 2017 for EP Application No. 15164212.1, 6 pages.

Office Action dated Oct. 27, 2016 for Chinese Application No. 201510154983.9, 5 page.

Application and File History of U.S. Appl. No. 13/081,406, filed Apr. 6, 2011, inventors Deem et al.

Decision to Revoke dated Feb. 27, 2018 for EP Patent No. 2555700, 92 pages.

Result of Oral Hearing dated Dec. 20, 2017 for EP Patent No. 2555700, 6 pages.

Written Submission in Preparation for Oral Hearing dated Oct. 30, 2017 for EP Patent No. 2555700, 280 pages.

Notice of Opposition dated Mar. 3, 2016 for EP Patent No. 2555700, 22 pages.

Patentee Reply to Notice of Opposition dated Oct. 21, 2016 for EP Patent No. 2555700, 67 pages.

File History for EP Patent No. 2555700, 192 pages.

Summons to Attend Oral Proceedings dated Apr. 12, 2018 for EP Application No. 15164212.1, 8 pages.

Office Action dated Oct. 30, 2018 for Canadian Application No. 2,795,564, 5 pages.

(56) References Cited

OTHER PUBLICATIONS

Search Report dated Feb. 19, 2019 for EP Application No. 18194554. 4, 12 pages.

* cited by examiner

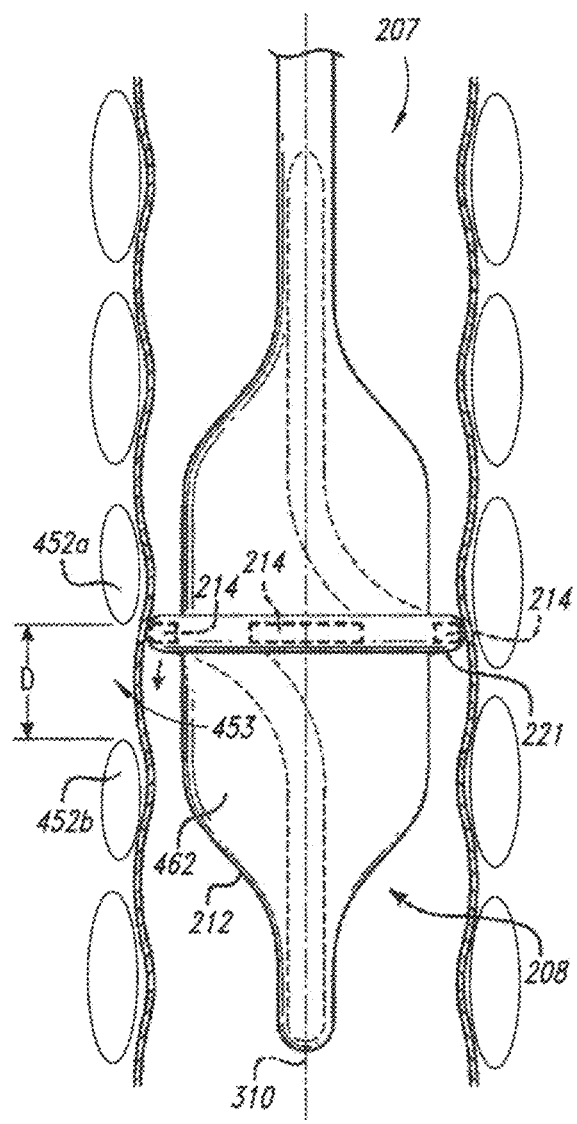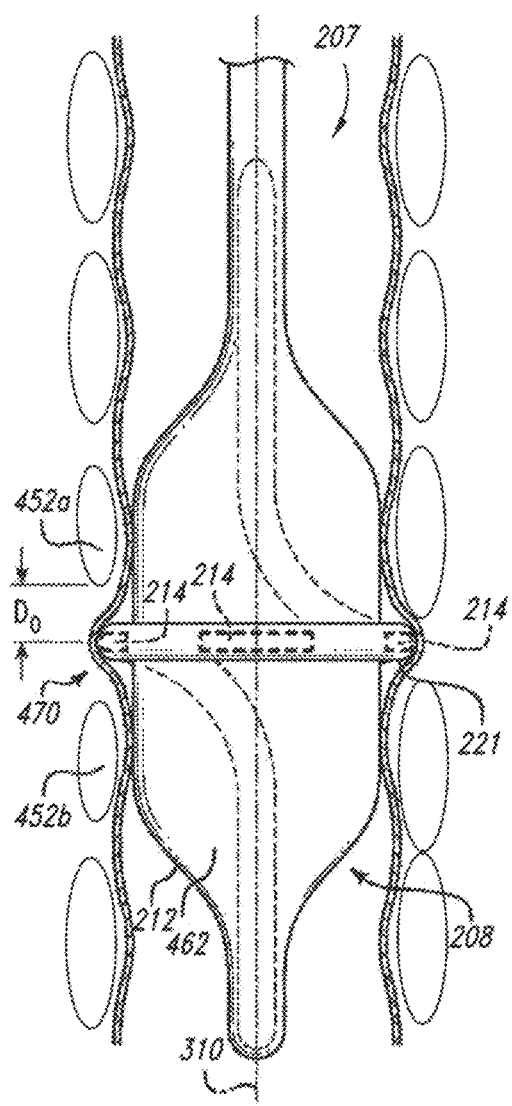
FIG. 20
FIG. 21

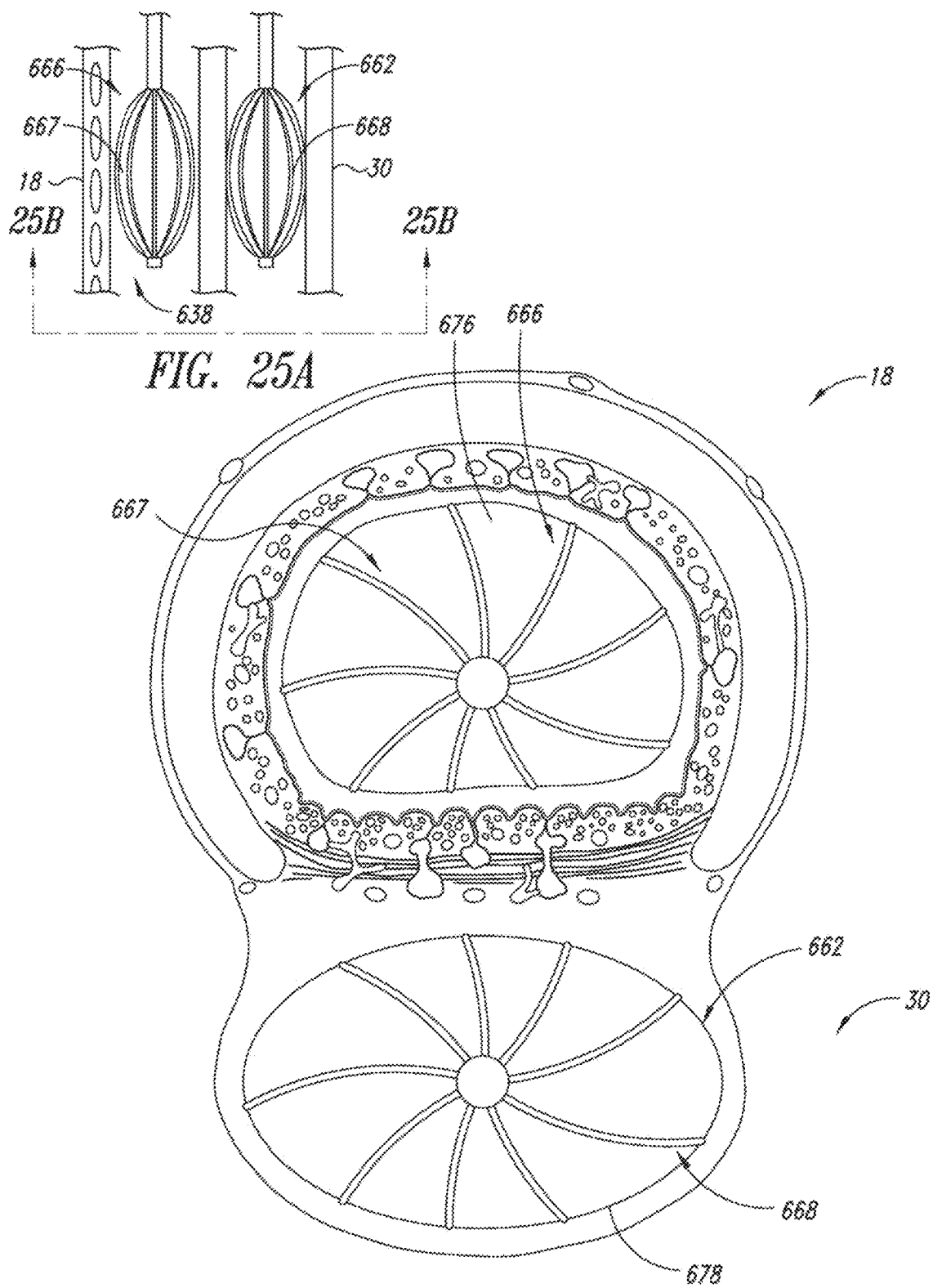

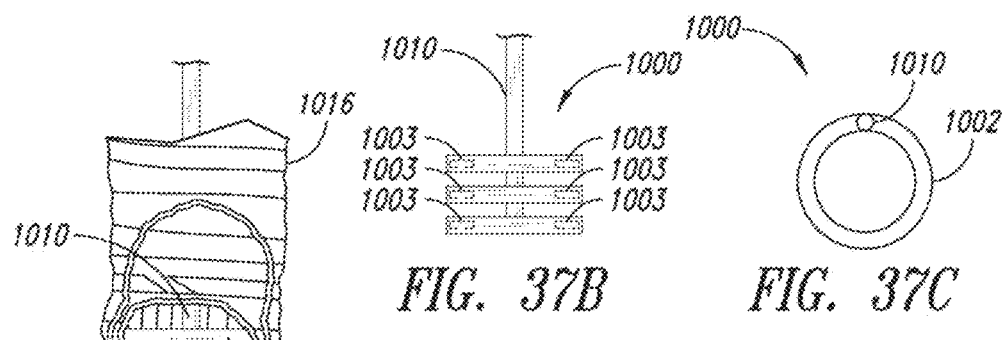
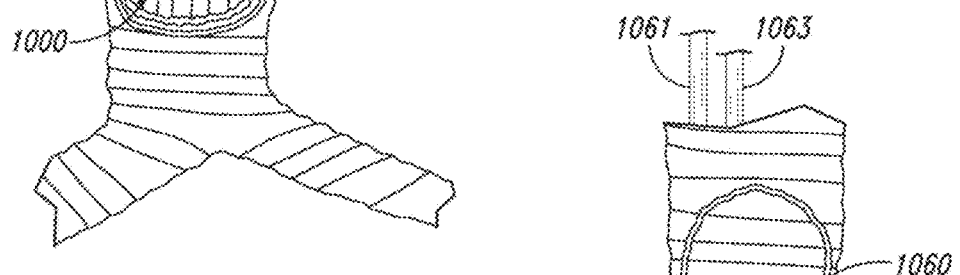
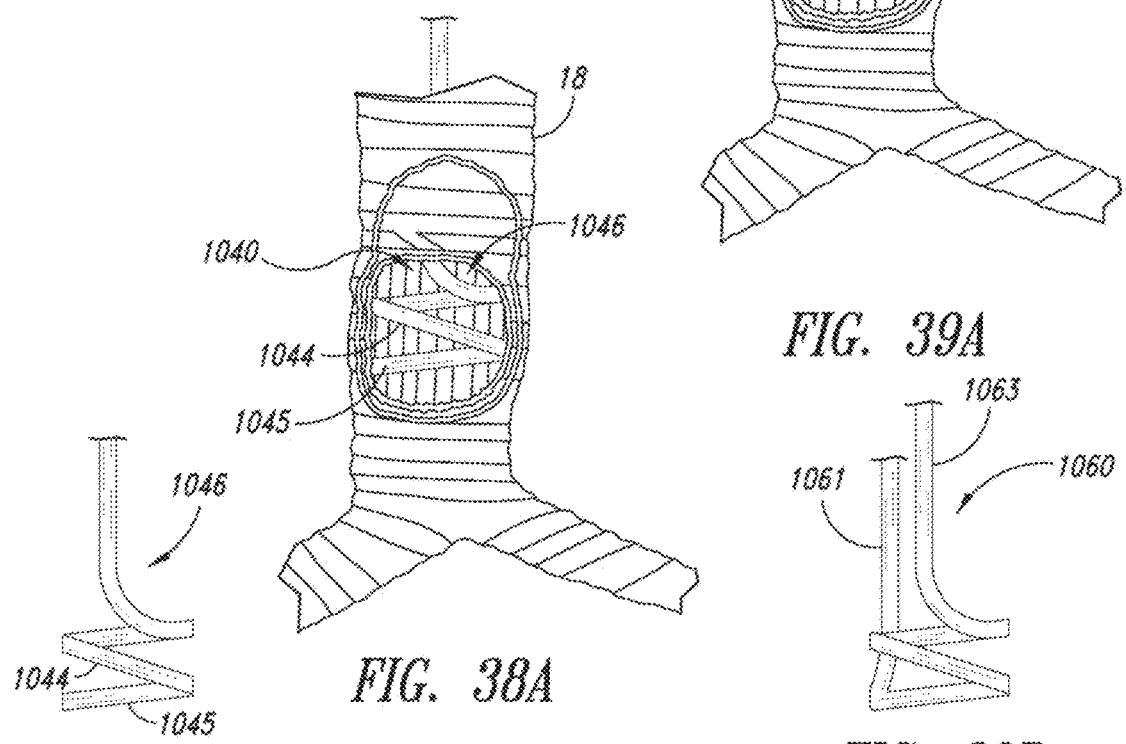
FIG. 37A  FIG. 37B  FIG. 37C
FIG. 38A  FIG. 38B
FIG. 39A  FIG. 39B

SYSTEM AND METHOD FOR PULMONARY TREATMENT

CROSS-REFERENCE TO RELATED APPLICATIONS

This application is a continuation-in-part of U.S. patent application Ser. No. 13/081,406 filed Apr. 6, 2011, which claims the benefit of U.S. Provisional Application No. 61/321,346 filed Apr. 6, 2010, each of which is hereby fully incorporated herein by reference.

BACKGROUND

Technical Field

The present invention generally relates to the field of pulmonary treatments.

Description of the Related Art

Pulmonary diseases are some of the most common medical conditions, affecting tens of millions of people in the U.S. alone. Pulmonary diseases result from problems in the respiratory tract that interfere with proper respiration. Many of these diseases require medical attention or intervention in order to restore proper lung function and improve a patient's overall quality of life. Some of the more common pulmonary diseases include asthma and chronic obstructive pulmonary disease or COPD. Symptoms of pulmonary disease like COPD and asthma vary but often include a persistent cough, shortness of breath, wheezing, chest tightness, and breathlessness. Generally, these symptoms are exacerbated when performing somewhat strenuous activities, such as running, jogging, brisk walking, etc. However, these symptoms may be noticed when performing non-strenuous activities, if the disease is allowed to progress unchecked. Over time, especially if medical attention is not sought, a person's daily activities will be significantly impaired, thus reducing overall quality of life.

A variety of treatments are available for pulmonary diseases includes reducing exposure to harmful agents, administering medications (e.g., bronchodilators, steroids, phosphodiesterase inhibitors, theophylline, antibiotics, etc.), administering lung therapy (e.g., oxygen therapy, pulmonary rehabilitation), and surgical intervention, such as bronchial thermoplasty. While these treatments are sometimes effective, typically the treatments are not without their drawbacks. For example, pharmacological treatment requires patient compliance, can cause undesirable or even harmful side effects, and may not always treat the underlying cause of the disease. Similarly, surgical intervention can result in the destruction of smooth muscle tone and nerve function, such that the patient is unable to respond favorably to inhaled irritants, systemic hormones, and both local and central nervous system input.

A relatively new and promising treatment for pulmonary diseases is targeted lung denervation (TLD). This method utilizes ablation, such as radio-frequency (RF) ablation via an ablation assembly to selectively treat target regions inside of the airway wall (e.g., anatomical features in the stromas) and/or target areas that run to the lung along the outside of the bronchus, while protecting superficial tissues such as the surface of the airway wall. For example, the mucous glands can be damaged to reduce mucus production a sufficient amount to prevent the accumulation of mucus that causes increased air flow resistance while preserving enough mucus production to maintain effective mucociliary transport, if needed or desired. Nerve branches/fibers passing through the airway wall or other anatomical features in the airway wall can also be destroyed.

Specially designed catheters allow for the introduction of an ablation assembly, generally comprising one or more collapsible electrodes or energy emitters, coupled to an expandable member, such as a balloon, into the airway of a patient via a delivery device. The delivery device can be a guide tube, a delivery sheath, a bronchoscope, or an endoscope and can include one or more viewing devices, such as optical viewing devices (e.g., cameras), optical trains (e.g., a set of lens), optical fibers, CCD chips, and the like. Once positioned in the desired region of the airway, such as the left and/or right main bronchi, the expandable member is expanded to position the one or more electrodes in contact with the airway wall.

Energy, such as RF energy, is supplied to the energy emitter to ablate the targeted tissue, causing a lesion to form, therefore temporarily or permanently damaging the targeted tissue, therefore affecting, e.g. attenuating nerve signals to or from, portions of the lungs associated with the targeted tissue. Simultaneously, a coolant is supplied through the catheter and is directed to the one or more electrodes and into the expandable member or balloon. This allows for cooling of the superficial tissue in contact with the electrode, as well as the adjacent tissues. The size, shape, and depth of the lesions are determined by the flow rate and temperature of the coolant, and the energy supplied to the energy emitter(s).

Devices, systems, and methods of targeted lung denervation are described in, for example, one or more of U.S. Pat. No. 8,088,127 to Mayse et al. and US Published Patent Application No. 2011/0152855 to Mayse et al., both of which are commonly assigned to the assignee of the present application and the disclosures of which are hereby incorporated by reference in their entireties.

One potential application of targeted lung denervation is treatment of the anterior pulmonary nerve plexus. An asthma treatment performed during the 1930's to 1950's, prior to the advent of effective asthma medications, was surgical sympathectomy of the posterior pulmonary nerve plexus. Although the surgery was very morbid, typically requiring severing large muscle groups and manipulating the ribs, pleura and lungs, it was in some cases effective.

There exists, in addition to the posterior pulmonary nerve plexus, an anterior pulmonary nerve plexus. Historically, the anterior pulmonary nerve plexus was never approached surgically due to its proximity to the heart and the great vessels. It is theorized that these nerves are also involved in airway constriction associated with asthma and other pulmonary diseases. There are several complicating factors to performing a denervation of these nerves from within the body. The nerves of interest run along the outside of the anterior trachea and bronchi, and the posterior plexus runs along the posterior, along and within the junction between the trachea and the esophagus. Damage to the esophagus or the branches of the vagus nerve that run along the outside of the esophagus and continue into the abdomen may be especially traumatic to a patient, and as a result of such difficulties there has historically been minimal interest in targeting the posterior and/or anterior pulmonary nerve plexus to treat pulmonary diseases.

Negative effects of ablation performed near the esophagus have been observed in association with cardiac ablation therapies, such as atrial fibrillation ablation therapies. These effects include esophageal fistulae and acute pyloric spasm and gastroparesis. Possible causes of these complications may be attributed to direct thermal energy delivered to esophageal tissue, injury to esophageal blood supply, late effects of an acidic environment within the esophagus, and/or injury to the vagus nerve and/or pulmonary nerve plexi.

In view of the risks of esophageal injury observed in cardiac ablation therapies, it would be advantageous if pulmonary-related ablation procedures could be performed near the esophagus without similar risks. Preferably such procedures would not only avoid injury to the esophagus directly, but injury to the peri-esophageal branches of the vagus nerve.

A need exists, therefore, for a solution to avoid injury to the esophagus during a pulmonary ablation procedure.

SUMMARY OF THE INVENTION

In general, embodiments of the invention are directed to devices and methods for treating one or more pulmonary diseases while avoiding or minimizing injury to the esophagus and branches of the vagus nerve that run along the outside of the esophagus. A number of possible approaches to avoiding injury to the esophagus and esophageal branches of the vagus nerve during pulmonary ablation therapy may be practiced either alone or in any combination contemplated by one of ordinary skill in the art.

At least some embodiments include a treatment system that can be used to perform pulmonary treatments to address a wide range of pulmonary symptoms, conditions, and/or diseases, including, without limitation, asthma, chronic obstructive pulmonary disease ("COPD"), obstructive lung diseases, or other diseases that lead to an unwanted (e.g., increased) resistance to airflow in the lungs.

In some embodiments, an apparatus for pulmonary treatment by select denervation includes an elongate member configured for insertion into the trachea to a position adjacent target nerve tissue, such as a pulmonary plexus. The apparatus further includes at least one energy delivery element disposed on the elongate member in a position corresponding to the anatomical location of at least one nerve in or adjacent the tracheal wall when the elongate member is positioned in the trachea. In certain embodiments, energy from a single energy delivery element ablates the at least one nerve. In other embodiments, a plurality of energy delivery elements cooperate to ablate or otherwise alter the nerve or other targeted tissue.

A pulmonary treatment method, in some embodiments, includes positioning at least one energy delivery element in a trachea or airway of the bronchial tree adjacent a nerve site to be treated. In some embodiments, energy from the element is delivered to a portion of the circumference of the trachea at the treatment site. Tissue adjacent the treatment site is cooled to prevent or reduce tissue damage outside the treatment site.

Some embodiments include an apparatus and method for targeting one or more target sites positioned between the lumens of the trachea and the esophagus. In certain embodiments, one or more devices are placed on the lumens of the trachea and/or esophagus to deliver energy so as to damage or otherwise alter one or more target sites located between the lumens of the trachea and the esophagus. The target sites can include nerve tissue. Preferably, such target sites are damaged while tissue closer to the lumens of the trachea and/or esophagus, including branches of the vagus nerve, are protected from damage.

A method for pulmonary treatment includes positioning at least one energy delivery element through at least a portion of the trachea into an airway adjacent a treatment site to be treated. In certain procedures, the airway is part of the trachea. In other procedures, the at least one energy delivery element is delivered through and out of the trachea and into the bronchial tree.

The method can further include delivering energy from the element to a portion of the circumference of the airway. The temperature of tissues can be adjusted to prevent or limited damaged to non-target tissue. In some procedures, tissues of an esophagus and branches of the vagus nerve are cooled or otherwise protected to prevent damage of the esophageal tissues while the energy is delivered. The esophageal tissues and nerves can also be cooled before and/or after delivering the energy.

The energy delivery element can be repositioned any number of times. In certain embodiments, the energy delivery element can be positioned in close proximity to the previous position. Energy is delivered to an adjacent treatment site. The adjacent site can barely overlap with the previous site. Alternatively, a small gap can be between the two treatment sites. The apparatus can be moved (e.g., rotated, translated, or both) to reposition the energy delivery element to provide a slight overlap or a slight gap circumferentially with respect to an already treated site.

In some embodiments, a pulmonary treatment apparatus includes an elongate member and a microwave antenna. The elongate member is insertable through at least a portion of a trachea into an airway. The microwave antenna is coupled to the elongate member and positionable in the airway at a treatment location proximate nerve tissue in a wall thereof. The microwave antenna is configured to deliver microwave energy so as to alter the nerve tissue in a manner which disrupts transmission of nerve signals therein while non-target tissue (e.g., tissue disposed between the microwave antenna and the nerve tissue) is not permanently injured. An active electrode can be non-inflatably (e.g., balloonlessly) expandable from a contracted configuration to an expanded configuration. Thus, the activated electrode can be moved without the use of a balloon or other type of expansion device.

A system for pulmonary treatment can include at least one pulmonary treatment device capable of damaging nerve tissue such that the destroyed nerve tissue impedes or stops the transmission of nervous system signals to nerves more distal along the bronchial tree. The nerve tissue can be temporarily or permanently damaged by delivering different types of energy to the nerve tissue. For example, the nerve tissue can be thermally damaged by increasing a temperature of the nerve tissue to a first temperature (e.g., an ablation temperature) while the wall of the airway is at a second temperature that is less than the first temperature. In some embodiments, a portion of the airway wall positioned radially inward from the nerve tissue can be at the first temperature so as to prevent permanent damage to the portion of the airway wall. The first temperature can be sufficiently high to cause permanent destruction of the nerve tissue. In some embodiments, the nerve tissue is part of a nerve trunk located in connective tissue outside of the airway wall. The smooth muscle and nerve tissue in the airway wall can remain functional to maintain a desired level of smooth muscle tone. The airway can constrict/dilate in response to stimulation (e.g., stimulation caused by inhaled irritants, the local nervous system, or systemic hormones). In other embodiments, the nerve tissue is part of a nerve branch or nerve fibers in the airway wall. In yet other embodiments, both nerve tissue of the nerve trunk and nerve tissue of nerve branches/fibers, in and/or along the airway wall, are simultaneously or sequentially damaged. Various types of activatable elements, such as ablation elements in the form of microwave antenna, ultrasound, RF electrodes, heating elements, or the like, can be utilized to output the energy.

At least some methods of pulmonary treatment include positioning an elongate member through at least a portion of the trachea. The elongate member has a treatment element and a sensor coupled thereto. A first tissue characteristic is sensed using the sensor with the treatment element at a first airway location. The first tissue characteristic is compared to a reference value to evaluate the location of the treatment element in the airway. The treatment element is activated to treat an airway.

In certain embodiments, an apparatus for pulmonary treatment includes an elongate member insertable through a trachea into an airway and an active electrode coupled to the elongate member. The active electrode is configured to deliver energy to target tissue in a wall of the airway. A return electrode is positionable in the airway or the esophagus and configured to receive the energy from the target tissue. A protection member is configured to cool non-target tissue proximate to the target tissue. The non-target tissue can be surrounded or can be spaced apart from the target tissue.

The active electrode is expandable from a contracted configuration to an expanded configuration without the use of a balloon. The device can be self-expanding. For example, the device can include a self-expanding basket, a cage, a wire mesh, or other type of component capable of assuming a helical, spiral, corkscrew, or similar configuration. As such the active electrode can be non-inflatably expanded or actuated.

A method of pulmonary treatment includes delivering energy at a first power level from an active portion of an energy delivery element to create a first lesion covering a first portion of a circumference of an airway. Energy is delivered at a second power level from the active portion of the energy delivery element to create a second lesion covering a second portion of the circumference of the airway displaced from the first portion. The first power level is substantially greater than the second power level. In certain embodiments, the second portion is circumferentially or axially displaced from the first portion relative to a lumen of the airway. For example, the second portion can be both circumferentially displaced and axially displaced from the first portion.

Another method of pulmonary treatment includes delivering a first amount of energy from an energy delivery device to a first portion of a wall of an airway and delivering a second amount of energy from the energy delivery device to a second portion of the airway wall. The first portion of the wall and the second portion of the wall are spaced apart from one another or can partially overlap one another. For example, most of the first and second portions by area or volume can overlap one another.

A method of pulmonary treatment includes positioning an energy delivery element in an airway of a subject. The energy delivery element is non-inflatably actuated. The energy delivery element can be moved into engagement with a wall of the airway without using a balloon or other type of inflation device. The energy delivery element can be self-expanding. For example, the energy delivery element can be a self-expandable cage. The non-inflatably expandable cage can move one or more electrodes proximate to or in contact with the airway wall.

Energy can be delivered from the energy delivery element to the wall of the airway to alter target nerve tissue therein or proximate thereto. A cooling medium is passed into the airway into direct contact with the wall to absorb heat from the wall while delivering the energy. Alternatively, a protection device can be used to cool the airway wall.

The energy delivery element can comprise a first electrode. The first electrode is positioned within a first space between a first pair of adjacent cartilage rings of the airway. A second electrode is placed in a second space between a second pair of adjacent cartilage rings of the airway. The electrode can be part of a helical or corkscrew shaped device.

In embodiments, a surface layer of tissue of the wall (e.g., a wall of the trachea, a wall of the esophagus, etc.) can be protected from permanent injury while a lesion of permanently injured tissue is created at a depth below the surface layer. The surface layer is at least about 2 mm in thickness. At least a portion of the lesion contains nerve tissue. In certain procedures, the nerve tissue is altered sufficiently to reduce airway constriction in the subject.

In one embodiment directed to protecting the esophagus and branches of the vagus nerve that run along the outside of the esophagus the esophagus during deneravation therapy, the adjacent tissue to the treatment site is actively cooled. In this embodiment, to cool the tissue, a cooling medium can be delivered through a device positioned along a lumen of the esophagus. The device can have one or more cooling balloons configured to contact the wall of the esophagus to absorb heat, thereby cooling non-targeted tissue. Additionally or alternatively, an apparatus in the trachea combined with or separate from the at least one energy delivery element can include one or more cooling devices (e.g., cooling balloons).

In this embodiment, a system for pulmonary treatment includes a pulmonary treatment device and a protection device. The pulmonary treatment device has one or more energy delivery elements positionable through at least a portion of a trachea into in an airway. The one or more energy delivery elements are configured to deliver energy to a wall of the airway to alter nerve tissue located in or proximate to the wall of the airway. The protection device has a protection member positionable in an esophagus even when the pulmonary treatment device is positioned in the airway. The protection member is configured to absorb heat from a wall of the esophagus to inhibit damage to esophageal tissue including certain branches of the vagus nerve. In some procedures, the system is used to ablate nerve tissue of nerve trunks traveling along the airway. Additionally or alternatively, nerve tissue within the airway wall can be ablated.

A cooling apparatus can be associated with the energy delivery element and/or protection device to limit tissue damage adjacent select denervation sites. The cooling apparatus can include one or more pumps, blowers, conduits, facemasks, valves, or the like. Media from the cooling apparatus can flow through the subject to cool internal tissue. In some embodiments, the cooling apparatus includes a pump that delivers chilled air through a conduit into a lumen of the esophagus. The chilled air circulates within the lumen to cool the esophageal tissue.

The cooling medium can include one or more gas or other type of media. The energy delivery element is coupled to an elongate member such that the cooling medium is introduced into the airway through a channel in the elongate member. The cooling medium flows through a channel in the energy delivery element to absorb heat therefrom.

In an alternative embodiment, the protection device can be positioned in the esophagus to absorb heat from esophageal tissue, including branches of the vagus nerve, while delivering the energy. Energy can be received by the protection device with or delivering energy from a second electrode coupled to the protection device.

According to another embodiment directed to protecting the esophagus and branches of the vagus nerve that run along the outside of the esophagus, a method includes selecting a treatment site within the airway, and particularly along the bronchus, that is separated from esophagus by a distance selected to reduce or eliminate the risk of applying excessive heat to esophageal tissues, including certain branches of the vagus nerve. For example, moving an ablation therapy or pulmonary treatment device farther away from the esophagus can be accomplished by moving the device more distal within the bronchus from the bifurcation of the left and right bronchus and closer to the lung. This is because the separation between the bronchus and the esophagus, particularly in the longer left bronchus, increases as the distance along the bronchus from the bifurcation increases.

According to yet another embodiment, reducing the power output of the therapy device, either generally around a circumference of the airway or only within the circumferential vicinity of the esophagus, such as a posterior portion of the bronchus, can reduce or avoid the occurrence of damage to the esophagus and branches of the vagus nerve that run along the outside of the esophagus. By reducing the power output, and therefore rate of energy provided to the treatment site in the vicinity of the esophagus, the risk of damage to the esophagus and vagus nerve branches is minimized. It has been found that lower power may be selectively applied only to specific tissue areas closest to the esophagus while achieving sufficient overall procedural efficacy. Similarly, cooling may be increased either by increased flow rate of coolant and/or decreased temperature of coolant supplied in this vicinity to more slowly bring the tissue up to temperature, and providing the ability to quickly cool the area once the power output is shut off.

According to another embodiment of the invention, in addition or as an alternative to actively cooling the esophagus during pulmonary ablation therapy described above, a contrast media, cooled or not cooled, can be circulated through the balloon catheter, and imaged so that the location of the esophagus relative to the treatment site is known either prior to and/or throughout the ablation treatment. In the event the esophagus is determined to be too close to safely deliver energy to the treatment site in the airway, delivering pulmonary ablation therapy in the vicinity can be reduced or avoided altogether, and risk of injury to the esophagus and branches of the vagus nerve that run along the outside of the esophagus is minimized.

According to another embodiment of the invention, monitoring the temperature of the esophagus during pulmonary ablation therapy and halting therapy as necessary can prevent or minimize esophageal damage and unwanted damage to branches of the vagus nerve that run along the outside of the esophagus. In this embodiment, a temperature of one or more portions of esophagus and/or surrounding tissue is monitored with a temperature probe placed in or around the esophagus near the treatment site during ablation treatment. In the event the observed temperature rises to an unacceptable or undesirable level, the power output may be reduced, cooling increased, or treatment may be halted altogether.

In yet another embodiment, physically moving the esophagus farther away from the pulmonary treatment site prior to and during the pulmonary ablation therapy may be an option for minimizing injury to the esophagus and branches of the vagus nerve that run along the outside of the esophagus. An esophagoscope or other suitable instrument may be placed in the esophagus and utilized to temporarily re-position the esophagus further from the treatment site while energy is applied to pulmonary tissue. In most individuals, the esophagus has significant mobility such that the esophagus can be readily moved at a safe distance from the treatment site.

In an alternative embodiment for moving the esophagus, a minimally invasive procedure is employed in which an expandable member, such as a balloon catheter, is percutaneously inserted and positioned interstitially between the airway proximate the treatment site and the esophagus. The balloon catheter is deployed, such as by filling with a gas or liquid, thereby lifting the esophagus away from the airway. Optionally, the liquid or gas can be cooled and circulated within the balloon catheter to provide additional protection via cooling of the esophagus. Optionally, a contrast media can be circulated within the balloon for imaging of the catheter. In an alternative embodiment, an expandable member can comprise an expandable basket, or other non-balloon type devices.

As described above, in some embodiments, a method for treating one or more pulmonary diseases may include damaging nerve tissue of a vagal nerve trunk extending along the outside of a bronchial tree airway or a nerve trunk within the airway wall so as to attenuate nervous system signals transmitted to a portion of the bronchial tree, while protecting the esophagus and branches of the vagus nerve that run along the outside of the esophagus. The nerve trunk may be the main stem of a nerve, comprising a bundle of nerve fibers bound together by a tough sheath of connective tissue. In some embodiments, the nerve tissue is damaged while maintaining a functionality of one or more anatomical features, such as blood vessels, also extending alongside the airway so as to preserve a respiratory function of the portion of the bronchial tree after the nerve tissue is damaged.

In some embodiments, a treatment system can be navigated through airways, such as the right and left main bronchi of the lung root, as well as more distal airways within the lungs, to treat a wide range of pulmonary symptoms, conditions, and/or diseases, including, without limitation, asthma, COPD, obstructive lung diseases, or other diseases that lead to an increased resistance to airflow in the lungs. A collapsible ablation assembly described above can be conveniently passed through airways. An energy emitter assembly of the ablation assembly can treat one or more target sites without treating non-targeted sites. Even if targeted anatomical features (e.g., nerves, glands, membranes, and the like) of main bronchi, lobar bronchi, segmental bronchi or subsegmental bronchi are treated, non-targeted anatomical features can be substantially unaltered. For example, the treatment system can destroy nerve tissue at target sites without destroying to any significant extent non-targeted tissue that can remain functional after performing treatment. The energy emitter assembly is coolable to avoid or limit destruction of non-targeted tissue.

Conditions and symptoms associated with pulmonary diseases can thereby be reduced, limited, or substantially eliminated. For example, airway obstruction can be treated to elicit reduced airflow resistance. Blood vessels or other tissue can remain intact and functional during and/or after treatment. The respiratory function that is preserved can include gas exchange, mucociliary transport, and the like. In some embodiments, the nerve tissue, such as nerve tissue of nerve trunks located outside of the airway, is damaged without damaging to any significant extent a portion of the airway wall that is circumferentially adjacent to the damaged nerve tissue. Accordingly, non-targeted tissue can be substantially unaltered by the damage to the airway nerve tissue.

Embodiments of the invention may include a pulmonary treatment catheter and handle system including a catheter assembly, a handle assembly, and a scope coupling assembly for coupling the handle assembly and catheter assembly to a delivery device, such as a bronchoscope. Embodiments further include a kit including the catheter assembly and handle assembly for coupling together and to a delivery device, such as a bronchoscope, via the scope coupling assembly, and instructions for methods of using such. The catheter assembly is further fluidly and electrically coupled to a system console, including a coolant supply and return reservoir, and an energy supply such as a RF generator, via the handle assembly.

The catheter assembly, handle assembly, and scope coupling assembly cooperate together to facilitate both circumferential and axial positioning of a catheter electrode in a treatment site, such as an airway, conduit, or vessel for treatment of the tissue, while maintaining known rotational and axial orientation of portions of the catheter assembly, such as an ablation assembly including an energy emitter or electrode, within the treatment site. The system can further facilitate optical coupling of the ablation assembly of the catheter assembly with a viewing device, such as a fiber optic camera at a working end of a bronchoscope, while maintaining independent movement of the viewing device with respect to the ablation assembly to achieve maximum viewing flexibility of the treatment site and ablation assembly. This allows for full viewing access of the electrode of the ablation assembly within the treatment site regardless of its orientation or positioning within the treatment site.

In embodiments, the catheter assembly comprises a targeted lung denervation RF, microwave, or ultrasound catheter, and generally includes an elongate shaft, and an ablation assembly coupled to a distal portion of the shaft, the ablation assembly including an expandable member, such as a balloon or basket, and one or more electrodes or energy emitters coupled to the expandable member. The catheter assembly also includes a cooling circuit including a coolant inflow and outflow lumen within the elongate shaft, and a coolant inlet path and return path (e.g., cooling conduit(s)) to circulate coolant to the expandable member and to the energy emitter, one or more power wires for supplying power to the energy emitter, optional thermocouple(s) and associated wires for measuring and sensing temperature at locations proximal to the electrode, optional cooling circuit pressure sensors and associated wired for measuring and sensing pressure within the cooling circuit, and/or optional pressure relief valves.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE SEVERAL VIEWS OF THE DRAWINGS

The invention may be more completely understood in consideration of the following detailed description of various embodiments of the invention in connection with the accompanying drawings, in which:

FIG. 20 is a side elevational view of an electrode adjacent a cartilaginous ring.

FIG. 21 is a side elevational view of electrodes positioned between cartilaginous rings.

FIG. 25A is a schematic view of a tracheal device and an esophageal device in a subject.

FIG. 25B is a schematic view of an embodiment employing trachea-to-esophagus circumferential bipolar electrodes.

FIGS. 31A and 32B are schematic views of an embodiment of the present invention employing trachea-to-esophagus bipolar electrodes with no balloon support.

FIGS. 37A-37C are schematic views of an embodiment of the present invention employing inter-cartilage electrodes in a stacked ring configuration.

FIGS. 38A and 38B are schematic views of an embodiment of the present invention employing inter-cartilage electrodes in a coiled configuration.

FIGS. 39A and 39B are schematic views of an embodiment of the present invention employing inter-cartilage electrodes with a winding adjustment element.

Figure 1:
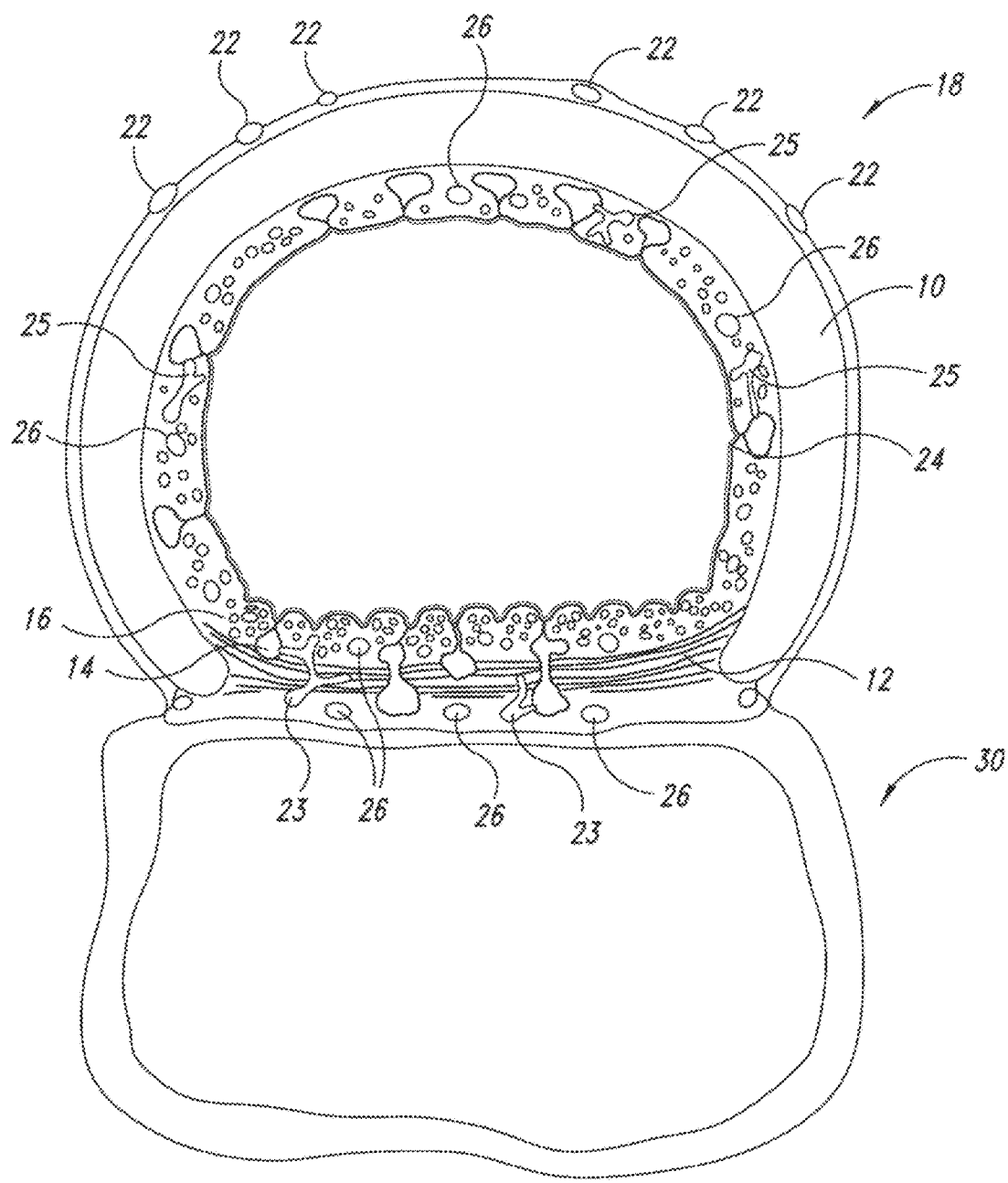
FIG. 1 shows a cross section of the trachea and esophagus, and approximate locations of the anterior and posterior plexus nerves.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION

Throughout this disclosure, the words disrupt, ablate, modulate, denervate will be used. It should be understood that these globally refer to any manipulation of the nerve that changes the action of that nerve. This can be a total cessation of signals, as in ablation or severing, or it can be a modulation, as is done by partial or temporary disruption, pacing, etc.

Similarly, trachea is often used to describe a segment wherein the devices and methods will be used. It should be understood that this is shorthand and can be meant to encompass the trachea itself, as well as the right and left main bronchi and other portions of the pulmonary tree as necessary.

It should be noted that the pulmonary nerves referred to in the disclosure not only include nerves that innervate the pulmonary system but also any neural structures that can influence pulmonary behavior. For example, elements of the cardiac plexus, or the nerves that innervate the esophagus, also interact with the airways and may contribute to asthmatic conditions. The nerves can include nerve trunks along the outer walls of hollow vessels, nerve fibers within the walls of hollow vessels (e.g., the wall of the trachea and/or esophagus), nerves within a bridge between the trachea and esophagus, or at other locations. The left and right vagus nerves originate in the brainstem, pass through the neck, and descend through the chest on either side of the trachea. These or a portion of these nerves can be targeted. The vagus nerves spread out into nerve trunks that include the anterior and posterior pulmonary plexuses that wrap around the trachea, the left main bronchus, and the right main bronchus. The nerve trunks also extend along and outside of the branching airways of the bronchial tree. Nerve trunks are the main stem of a nerve comprising a bundle of nerve fibers bound together by a tough sheath of connective tissue. The vagus nerves, including their nerve trunks, along the trachea or other nerve tissue along, proximate to, or in the bronchial tree can be targeted, while branches that run along, proximate to, or in the esophagus can be not targeted and/or protected via the embodiments set forth below. A treatment device in the form of a tracheal device can be positioned at different locations within an airway (e.g., the trachea, one of the main stem bronchi, or other structures of the bronchial tree).

The pulmonary branches of the vagus nerve along the left and right main stem bronchus intermedius are particularly preferred targets. The nerve trunks of the pulmonary branches extend along and outside of the left and right main stem bronchus and distal airways of the bronchial tree. Nerve trunks of the main stem nerve comprise a bundle of nerve fibers bound together by a tough sheath of connective tissue. Any number of procedures can be performed on one or more nerve trunks to affect the portion of the lung associated with those nerve trunks. Because some of the nerve tissue in the network of nerve trunks coalesce into other nerves (e.g., nerves connected to the esophagus, nerves though the chest and into the abdomen, and the like), specific sites can be targeted to minimize, limit, or substantially eliminate unwanted damage of those other nerves.

Some fibers of anterior and posterior pulmonary plexuses coalesce into small nerve trunks which extend along the outer surfaces of the trachea and the branching bronchi and bronchioles as they travel outward into the lungs. Along the branching bronchi, these small nerve trunks continually ramify with each other and send fibers into the walls of the airways. Any of those nerve trunks or nerve tissue in walls can be targeted.

The aspects, embodiments, features, systems, devices, materials, methods and techniques described herein may, in some embodiments, be similar to any one or more of the embodiments, features, systems, devices, materials, methods and techniques disclosed in any one or more of the following applications and patents: PCT Publication Nos. WO2014/143898 and WO2015/038886, both to Mayse et al.; U.S. Patent Application Publication Nos. 2011/0152855 to Mayse et al., 2011/0301587 to Deem et al., 2012/0310233 to Dimmer et al., 2013/0310822 to Mayse et al., 2014/0186341 to Mayse, and 2014/0257271 to Mayse et al.; U.S. Pat. No. 8,088,127 to Mayse et al., U.S. Pat. No. 8,172,827 to Deem et al., U.S. Pat. No. 8,483,831 Hlavka et al., and U.S. Pat. No. 8,911,439 to Mayse et al. Further, the systems and methods disclosed herein can employ any of the cooling systems described in U.S. Patent Application Publication No. 2014/0276792 and PCT Publication No. WO2014/160422, both to Kaveckis et al., and/or any of the handle systems described in PCT Publication Nos. WO2015/089377 to Harshman et al. The disclosures of each of the above-identified applications and patents are hereby incorporated by reference in their entireties, except for the claims and any expressly contradictory definitions.

Furthermore, it is contemplated that application is not limited to protection of the esophagus and branches of the vagus nerve that run along the outside of the esophagus (herein collectively referred to as "esophageal tissue" and "esophageal protection") during the application of energy, but can also be employed for esophageal protection during the application of toxins, medicants, and/or other agents, for the insertion of insertable devices such as needles into an airway wall for the delivery of energy and/or toxins and the like, and/or any other treatment or delivery method in which it is desired to protect esophageal or other non-targeted areas. For example, it may be advantageous to monitor the location of the esophagus, esophageal tissue, nerves running along the esophagus, or other such tissues in relation to a treatment area before, during, and/or after treatment so as to alter treatment in certain situations to protect the non-targeted areas.

The aspects, embodiments, features, systems, devices, materials, methods and techniques described in the attached disclosure may, in certain embodiments, be applied to or used in connection with any one or more of the embodiments, features, systems, devices, materials, methods and techniques disclosed in the above-mentioned applications and patents.

Figure 2:
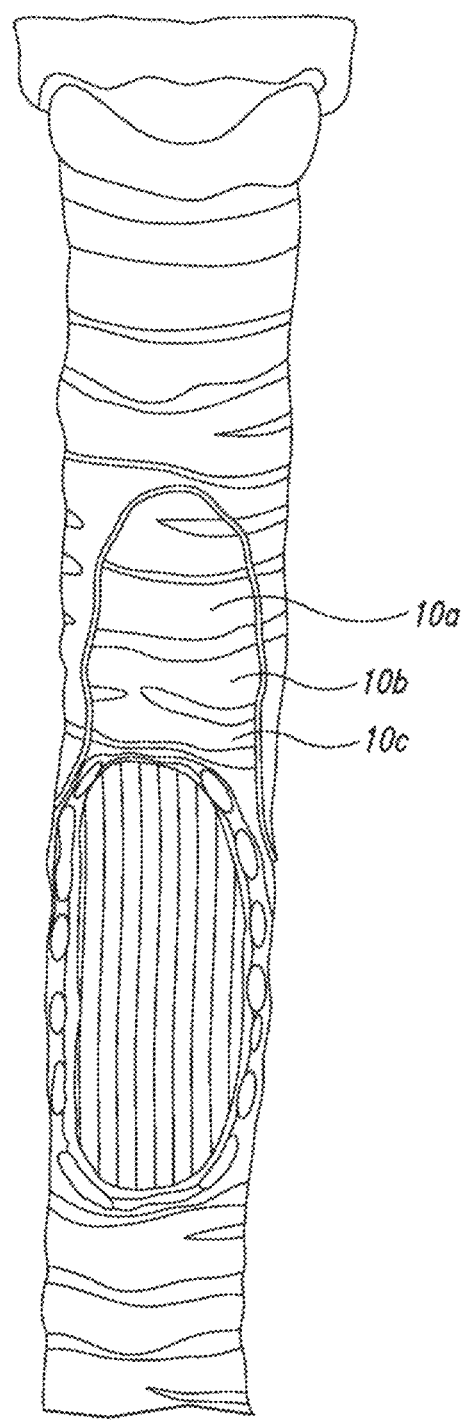
FIG. 2 shows the cartilaginous rings of the trachea. The connective tissue sheath is shown cut away.

As illustrated in FIG. 1, the C-shaped structure 10 that separates the inner elements of the airway—the smooth muscle 12, goblet cells 16, mucosa, anterior plexus nerves 22, posterior plexus nerves 23, epithelium 24, nerves 25, arteries 26, etc.,—from the nerves are thick bands of cartilage 10. These bands 10 cover the majority of the circumference of the trachea and larger bronchi, with a discontinuity only along the posterior segment where the trachea and esophagus are coincident. As further shown in FIG. 2, these bands 10a, 10b, 10c (collectively "10") are discrete elements, arranged longitudinally along the length of the trachea 18 and large bronchi, with thinner areas of connective tissue between them. The anterior plexus runs outside of these bands. So it can be seen that any modality designed to sever or disrupt these nerves will be heavily guarded against by these rings.

A different complication exists along the posterior border where the discontinuity in the cartilage bands exists. Here, the trachea and esophagus are coincident, connected to one another by an area of connective tissue. Here the problem is the opposite of that on the posterior side. The esophagus can be easily damaged by devices operating from within the lung to disrupt or modulate the nerves running between the two lumens. A rare but fatal complication of cardiac ablation for the treatment of atrial fibrillation occurs when ablations performed within the heart create a weakness along the esophagus (the posterior left atrium is also adjacent the esophagus). In some cases, this weakness turns into a fistula, causing atrial rupture, massive hemorrhage and death. So it is critical to protect these ancillary structures or to direct the means for disruption or modulation away from them.

Figure 3:
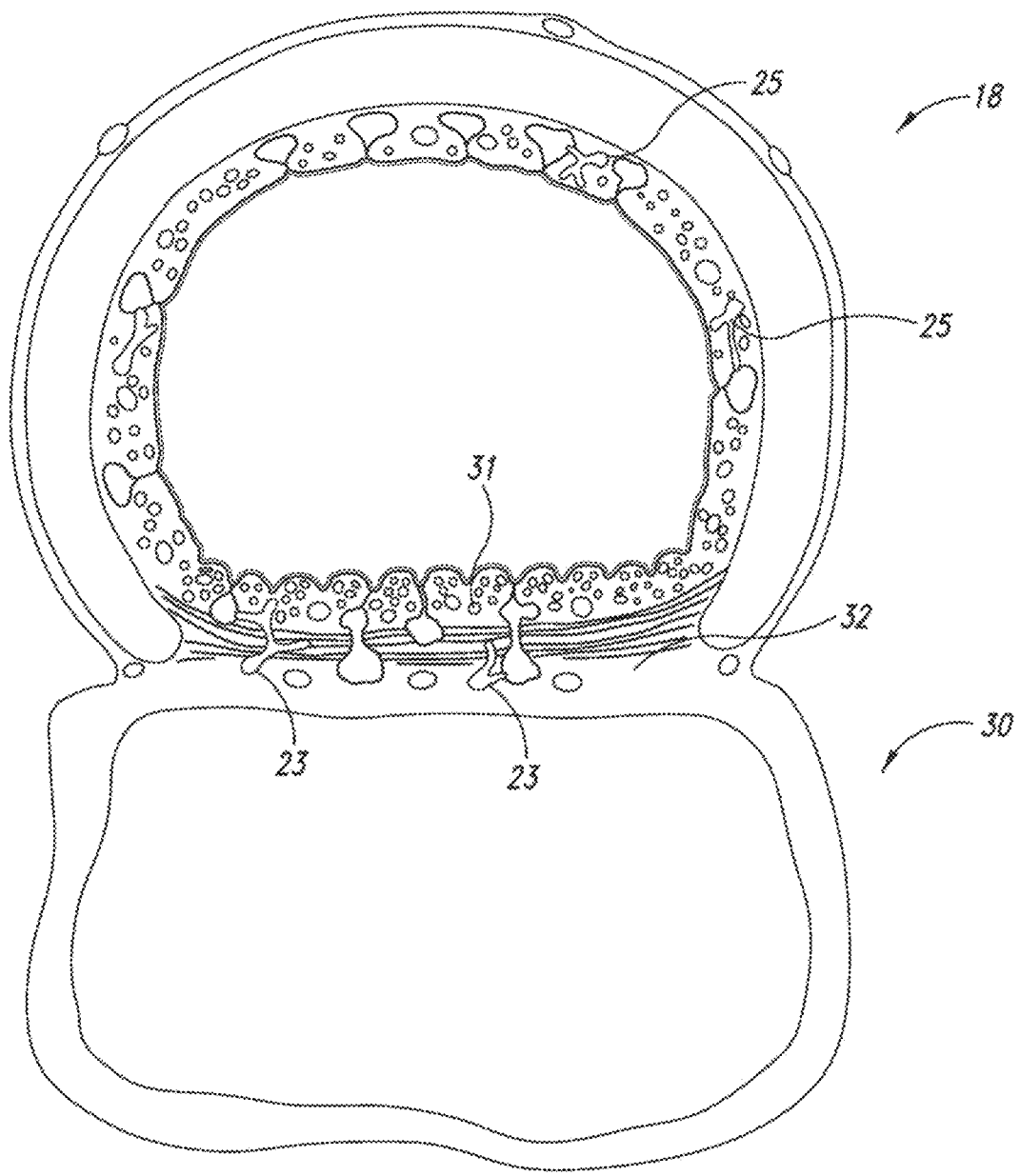
FIG. 3 shows the trachea in cross section, illustrating a target region in the pulmonary plexus for treatment in embodiments of the present invention.

It can be seen from these descriptions of the anatomy of the trachea 18 and esophagus 30 that (as shown in FIG. 3) energy or treatment means directed at or through the posterior wall 31 of the trachea 18, or the anterior wall 32 of the esophagus 30, would have direct access to the posterior pulmonary plexus 23.

A potential region of interest for pulmonary nerve therapy is further described with reference to FIG. 4A. Nerves which supply the pulmonary plexus arise from multiple levels of the thoracic spine 38 as well as multiple levels of the vagus nerve. Treatment and/or therapy delivery may occur anywhere within this potential target region 40, as a single treatment or as a plurality of treatments, administered in a single treatment session or staged over multiple sessions.

To modulate or disable the pulmonary nerves, it can be seen from the above anatomical descriptions that protection and or therapy can be delivered via the trachea 18, main stem bronchii or other airways further distally in the bronchial tree, the esophagus 30, or combinations of these. Following are brief descriptions of a number of different embodiments wherein energy is delivered to the targeted nerves through combinations of devices, or in some embodiments, through a single device. The targeted nerves can run along the trachea 18 and the esophagus 30, between the trachea 18 and the esophagus 30, or other suitable locations. For example, nerve tissue within walls of the trachea 18 and/or the esophagus 30 can be destroyed or otherwise altered. Alternatively or additionally, nerve trunks running along the outer wall of the trachea 18 and/or the esophagus 30 can be altered or destroyed.

Figure 4:
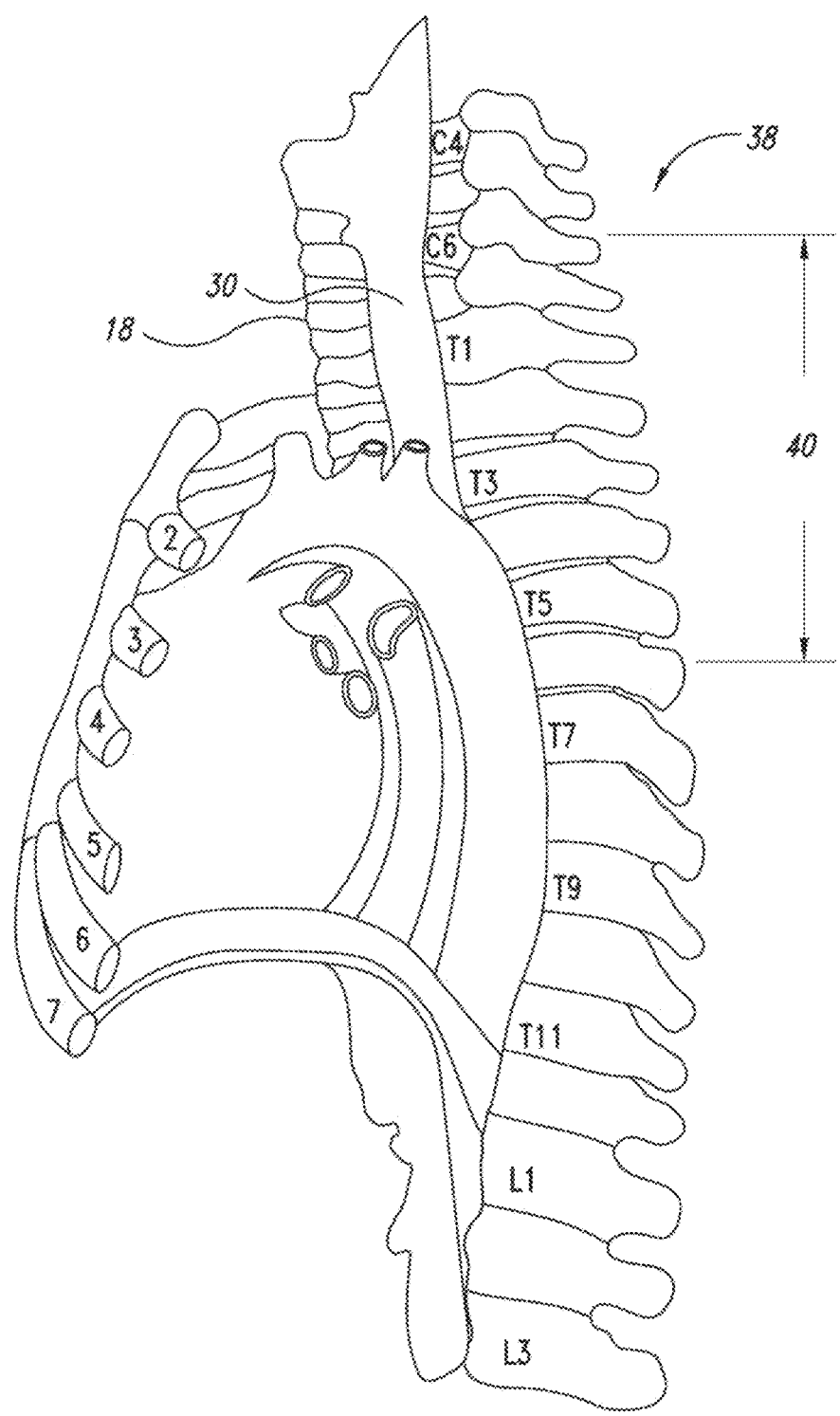
FIG. 4 is a lateral view illustrating the length of a potential target region corresponding to the cross section in FIG. 3.
Figure 4A:
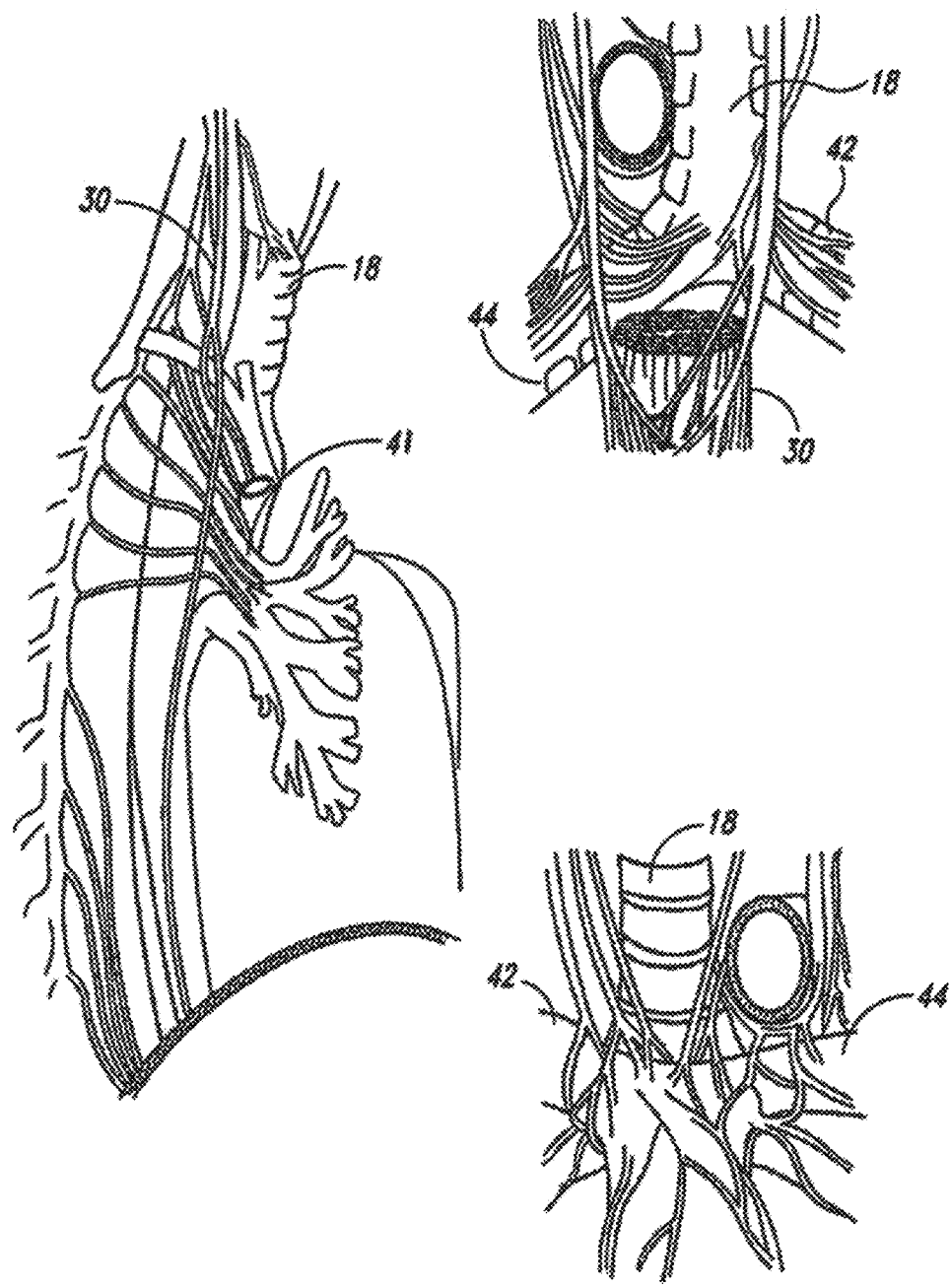
FIG. 4A is an anatomical drawing showing details of the posterior pulmonary plexus.

In addition to the potential access to the pulmonary plexus 23 from the area of the trachea 18 and the correlated area in the esophagus 30, it can be seen from FIG. 4A that a good number of branches from the thoracic ganglia 40 converge in the area of the carina, and the areas of the upper right bronchi 42 and upper left bronchi 44. Thus, the esophagus 30 may still need to be protected if tissue modification is to be done in the area of the carina, but as the target area moves more distally down the right and left bronchi, the need for esophageal protection diminishes.

Another reason that it may be beneficial to focus the treatment area more towards the individual right and left bronchi 42, 44 is that the recurrent laryngeal nerve may in some cases be collocated with nerves supplying the pulmonary plexus as they travel down the tracheal/esophageal interface to the lower areas of the plexus. Damage to the laryngeal nerve was shown in the surgical literature for pulmonary sympathectomy to be associated with complications of speech and swallowing, so preserving its function is critical.

Of note, as the treatment zone is located farther down the bronchial tree, past the carina and away from the trachea, the cartilaginous rings become completely circumferential—the area of non-coverage which was available for exploitation by a treatment device is no longer present. With this in mind, devices targeting regions of full cartilaginous coverage may have the requirement that they need to traverse and deliver therapy around, between or through these rings in order to reach the target nerves.

According to certain embodiments of the invention, devices may be configured for the delivery of radio frequency energy to modulate or disable the pulmonary plexus. While embodiments shown are configured for delivery of RF energy, many of the configurations can also be adapted to accommodate a catheter based microwave antenna, high energy pulse electroporation, or similar energy modalities.

The RF energy can be delivered in a traditional conductive mode RF, where the energy is directly applied to the tissue through a direct contact electrode, or it can be delivered through the use of capacitive coupling to the tissue. In capacitive coupling, a slightly higher frequency signal is typically used compared to traditional RF, and the energy is delivered to the tissue across a dielectric, which is often a cooling element. In one example of capacitive coupling, energy may be delivered across a cooling plate that keeps the surface of tissue contacted from being harmed as energy is delivered deeper into the target tissue.

The RF energy can be delivered to different target regions, which can include, without limitation, nerve tissue (e.g., tissue of the vagus nerves, nerve trunks, etc.), fibrous tissue, diseased or abnormal tissues (e.g., cancerous tissue, inflamed tissue, and the like), cardiac tissue, muscle tissue, blood, blood vessels, anatomical features (e.g., membranes, glands, cilia, and the like), or other sites of interest. In RF ablation, heat is generated due to the tissue resistance as RF electrical current travels through the tissue. The tissue resistance results in power dissipation that is equal to the current flow squared times the tissue resistance. To ablate deep tissues, tissue between an RF electrode and the deep tissue can become heated if active cooling is not employed using a cooling device, such as a cooling plate or cooling balloon. The cooling device can be used to keep tissue near the electrode below a temperature that results in cell death or damage, thereby protecting tissue. For example, cooling can prevent or limit overheating at the electrode-tissue interface. Overheating (e.g., tissue at temperatures above 95° C. to about 110° C.) can lead to the formation of coagulum, tissue desiccation, tissue charring, and explosive outgassing of steam. These effects can result in increased tissue resistance and reduced RF energy transfer into the tissue, thereby limiting the effective RF ablation lesion depth. Active cooling can be used to produce significantly deeper tissue lesions. The temperature of coolant for active cooling can be about 0° C. to about 24° C. In some embodiments, the coolant and electrode produce a lesion at a therapeutic depth of at least about 3 mm while protecting tissue at shallower depths from lethal injury. In some embodiments, the lesions can be formed at a depth of about 3 mm to about 5 mm to damage nerve tissue. Other temperatures and depths can be achieved.

Figure 5:
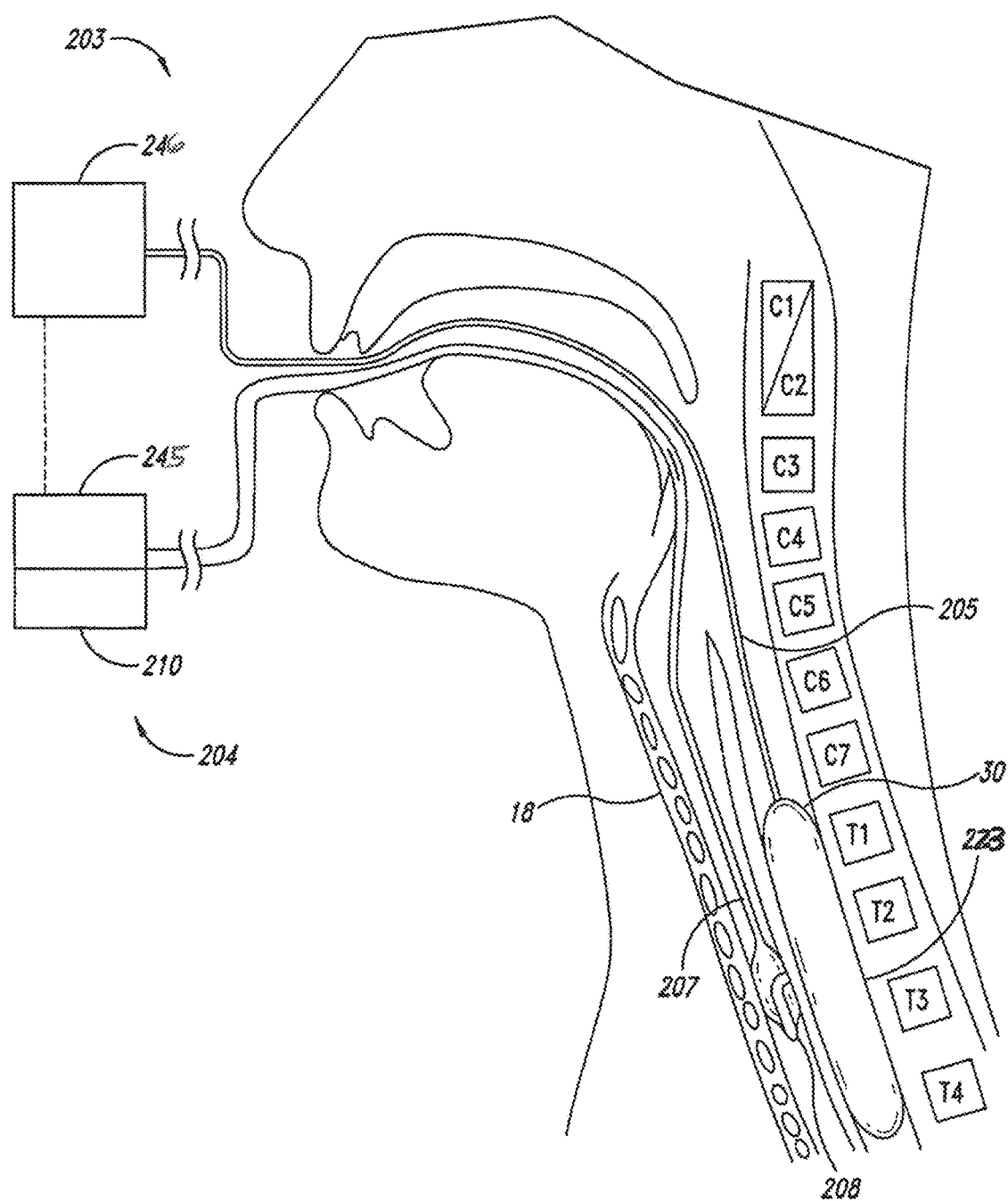
FIG. 5 is a lateral view of a treatment system positioned in the trachea and the esophagus.

FIG. 5 shows a system 204 including a pulmonary treatment device in the form of a tracheal catheter 207 positioned in the trachea 18 and a protection device 205, or temperature control device, positioned in the esophagus 30. An energy delivery assembly 208 is positioned to deliver energy to ablate targeted tissue between the trachea 18 and esophagus 30 while protecting non-targeted tissue. The temperature control device 205 includes a protection member 212 that absorbs heat to cool and protect tissue of the esophagus 30, thereby inhibiting damage to esophageal tissue. The tracheal catheter 207 can deliver a sufficient amount of energy to the trachea wall to heat and damage target tissue while the temperature control device 205 absorbs a sufficient amount of heat from the esophagus wall to inhibit damage to esophageal tissue while the target tissue is damaged. The tracheal device 204 and the temperature control device 205 can cooperate to ablate or otherwise alter targeted tissue, such as the pulmonary plexus 32.

It will be understood that, with regard to any of the embodiments described herein, while described here for use in the trachea, the devices and methods of the invention may be used for treatment in more distal airways including the mainstem bronchii, broncus intermedius, and more distal branches of the bronchial tree. Thus the terms "tracheal device" and the like are not intended to be limited to devices used in the trachea and may be interpreted to mean devices for use in any location in the trachea or bronchial tree where nerve tissue may be targeted to treat asthma and other pulmonary diseases using the techniques described herein.

Figure 6:
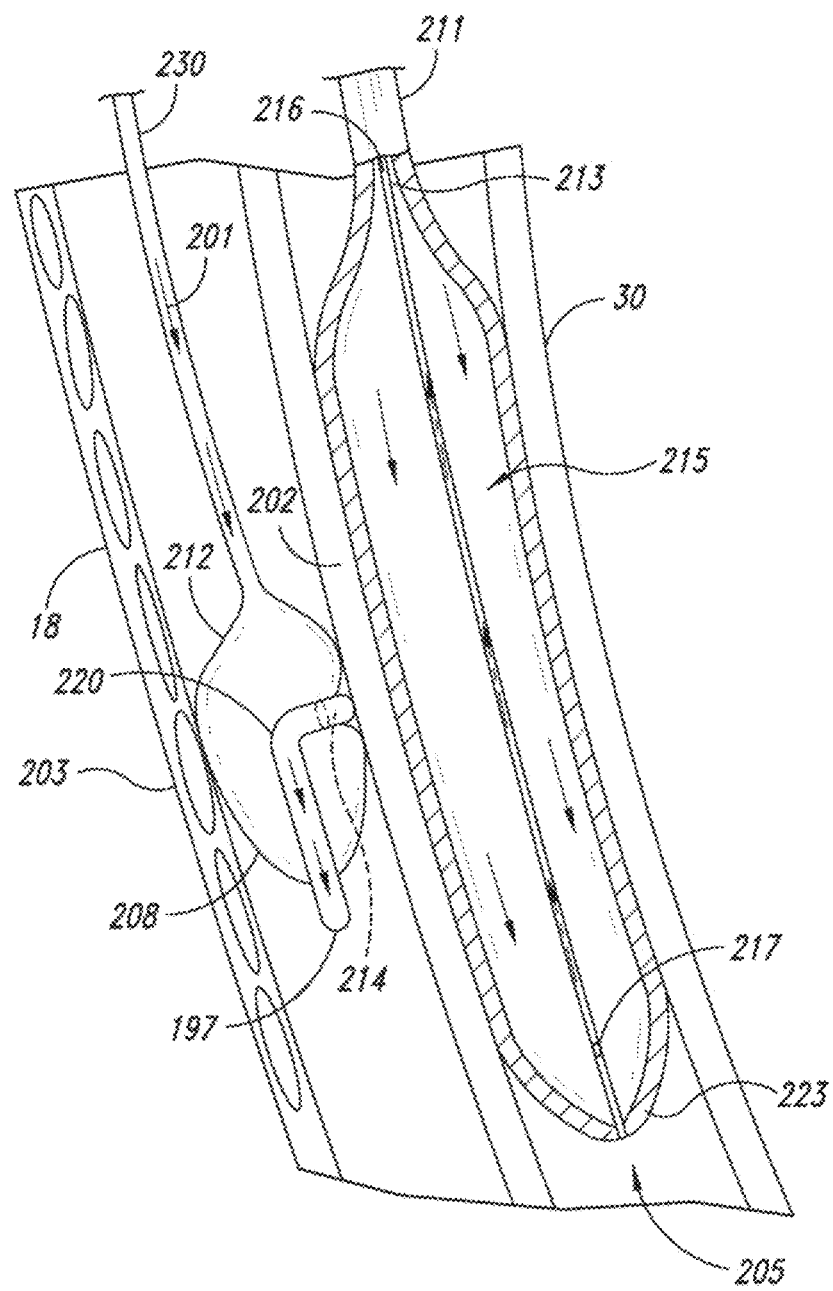
FIG. 6 is a detailed view of a treatment device in the trachea and an esophageal device in the esophagus.
Figure 7:
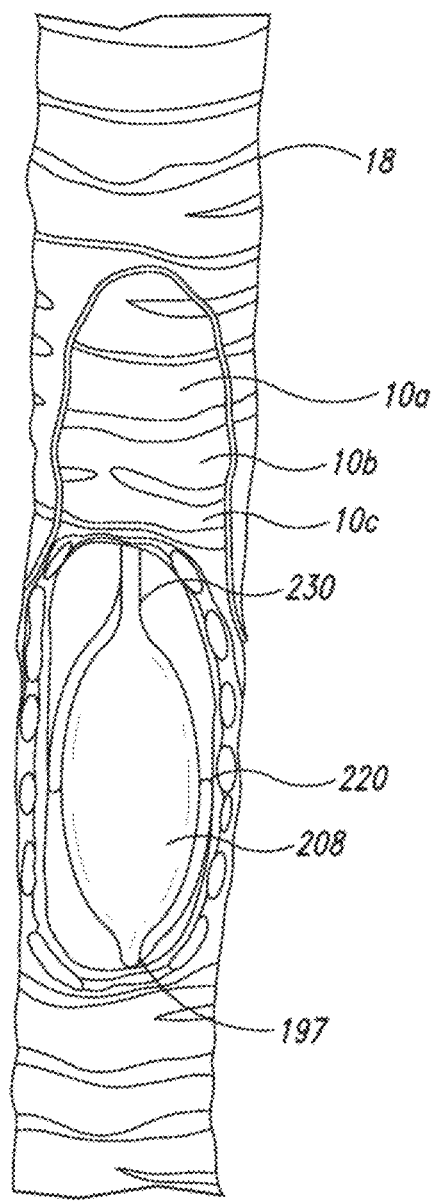
FIG. 7 is cutaway view of a trachea and a distal tip of the treatment device.

Referring to FIGS. 6 and 7, if the energy delivery assembly 208 includes an energy delivery element in the form of an RF electrode 214, the electrode 214 can be brought into contact with or proximate to an inner surface of the trachea 18. The RF electrode 214 can output RF energy which travels through the tissue and is converted into heat. The heat causes formation of a lesion. The RF energy can be directed radially outward towards the targeted tissue without causing appreciable damage to non-targeted tissue (e.g., tissue of the esophagus 30, inner tissue of the trachea 18, anterior tissue of the trachea 18) using coolant (represented by arrows 201). A wide range of different procedures, such as, for example, denervation of a portion of the trachea 18, an entire circumference of the trachea 18, target nerve trunks travelling to one lung or both lungs, or the like. Nerve tissue is damaged to relax the muscle tissue in the bronchial tree to dilate the airway to reduce air flow resistance in one or both lungs, thereby allowing more air to reach the alveolar sacs for the gas exchange process. Decreases in airway resistance may indicate that passageways of airways are opening, for example in response to attenuation of nervous system input to those airways. The balloon 212 can absorb heat to cool the anterior region 203 (shown removed in FIG. 7) of the trachea 18. Emitter assembly 220 wraps around the balloon 212 to contact the posterior region 202 of the trachea 18, as shown in FIG. 6. The emitter assembly 220 extends along the balloon 212 to a distal tip 197.

A physician can select and ablate or otherwise alter appropriate nerve tissue to achieve a desired decrease in airway resistance, which can be measured at a subject's mouth, a bronchial branch that is proximate to the treatment site, a trachea, or any other suitable location. The airway resistance can be measured before performing the therapy, during the therapy, and/or after the therapy. In some embodiments, airway resistance is measured at a location within the bronchial tree by, for example, using a vented treatment system that allows for respiration from areas that are more distal to the treatment site. Any number of procedures can be used to treat asthma, COPD, and other diseases, conditions, or symptoms.

The temperature control device 205 of FIG. 6 includes an elongate member 211 connected to the inflatable member 223. Media, such as chilled saline, flows through an input lumen 213 and circulates through a chamber 215. The media absorbs heat and exits the chamber 215 through an outlet 217. The media flows proximally through an output tube 216. The longitudinal length of the inflatable member 223 can be longer than a longitudinal length of the energy delivery assembly 208 to ensure that a longitudinal section of tissue extending distally and proximally of the targeted tissue is cooled to avoid unwanted tissue alteration, for example, tissue damage.

Figure 8A:
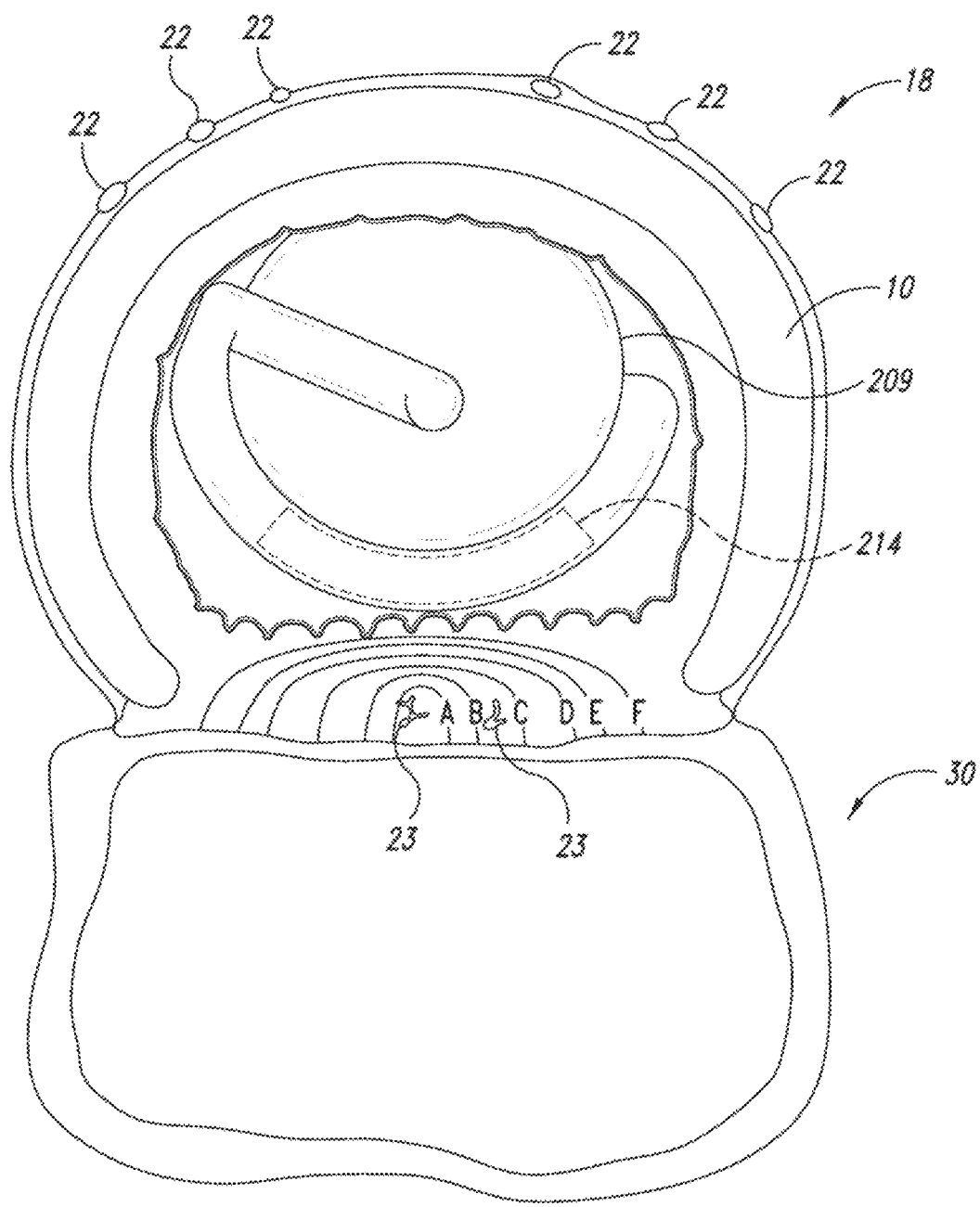
FIG. 8A is a cross-sectional view of the trachea and isotherms in tissue of the trachea and the esophagus.
Figure 8B:
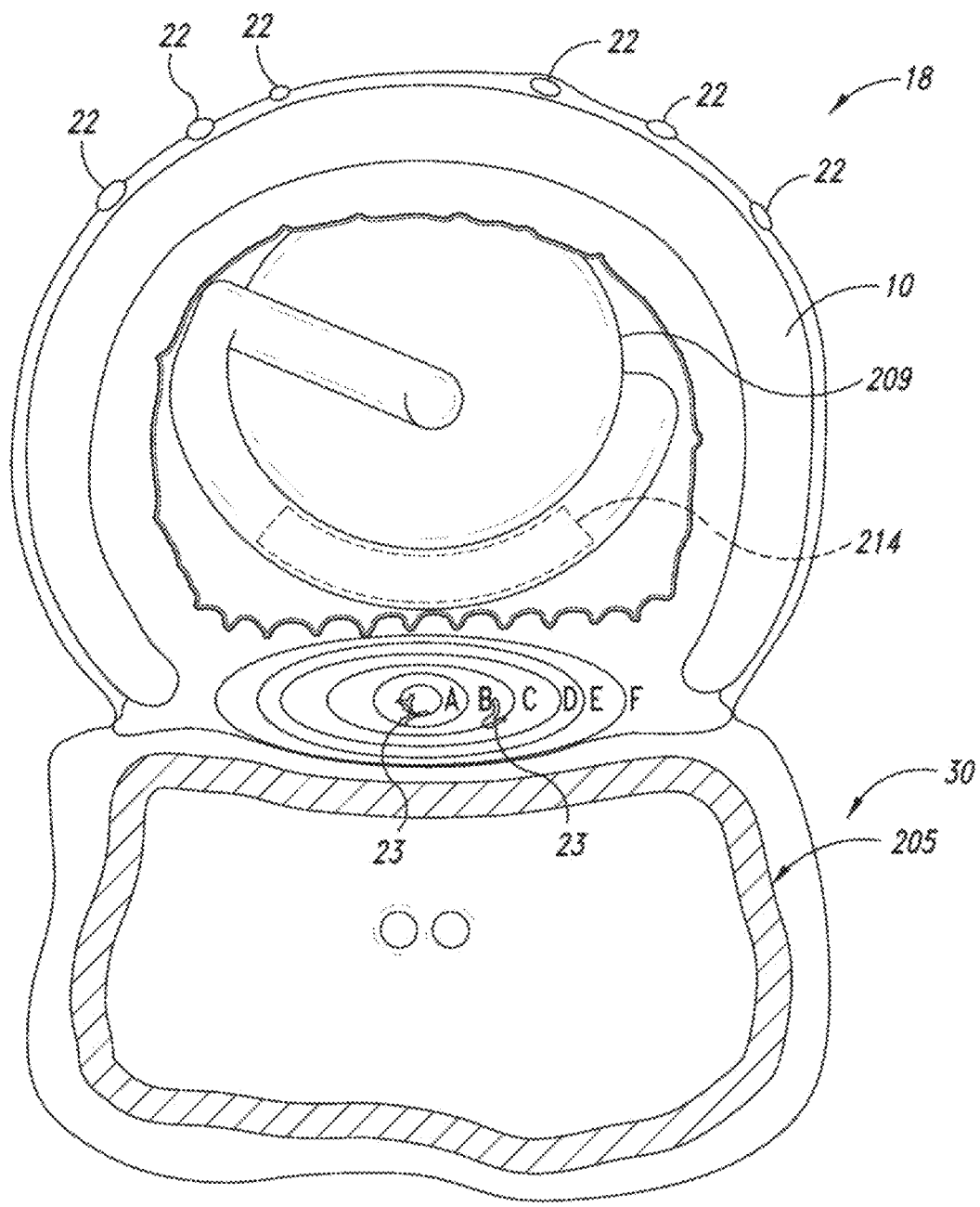
FIG. 8B is a cross-sectional view of the trachea and isotherms in tissue of the trachea and the esophagus.

FIGS. 8A and 8B show isotherms. By adjusting the rate of power delivery to an electrode 214, the rate at which media is passed into the energy delivery assembly 208, the rate at which media is passed into the inflatable member 212, the temperatures of the media, the sizes and configuration of energy delivery assembly 208/inflatable member 212, and the exact contour and temperature of the individual isotherms can be modified. An energy distribution can be produced which results in isotherm A being warmest and, moving radially outward from isotherm A, each successive isotherm becomes cooler, with isotherm F being coolest. At minimum, the temperature at isotherm A will be high enough to produce cell death in the target tissue. In at least some preferred embodiments, isotherm A will be in a range of about 50° C. to about 90° C., more preferably about 60° C. to about 85° C., and most preferably about 70° C. to about 80° C. Isotherm F will be at or around body temperature, and the intervening isotherms will be at intervals between body temperature and the temperature at isotherm A. For example, by selecting the proper temperature and flow rate of saline and the rate of power delivery to the electrode, it is possible to achieve temperatures in which isotherm A=70° C., B=55° C., C=50° C., D=45° C., E=40° C., and F=37° C. In some tissues, a lethal temperature may be greater than or equal to about 70° C. For example, the A isotherm can be about 75° C. to about 80° C. to form lesions in nerve tissue. Different isotherms and temperature profiles can be generated for different types of tissue because different types of tissue can be affected at different temperatures. Further adjustments make it possible to achieve temperatures where isotherm A=50° C., B=47.5° C., C=45° C., D=42.5° C., E=40° C., and F=37° C. Alternative adjustments make it possible to achieve temperatures where isotherm A is equal to or greater than 90° C., B=80° C., C=70° C., D=60° C., E=50° C., and F=40° C. Only those areas contained within the A and B isotherms will be heated enough to induce cell death for certain types of tissue. Other temperature ranges are also possible depending on the lethal temperature of the target tissue. In some procedures, tissue at a depth of about 2 mm to about 8 mm in the airway wall can be ablated while other non-targeted tissues at a depth of less than 2 mm in the airway wall are kept at a temperature below a temperature that would cause cell death. The isotherms of FIG. 8A can be generated without cooling using the temperature control device 205. By cooling tissue using the temperature control device 205, the isotherms generate bands, as illustrated in FIG. 8B. Advantageously, the interior tissues of the trachea 18 and the esophagus 30 can be undamaged while deep tissue, including nerve tissue 23, is damaged.

Figure 9:
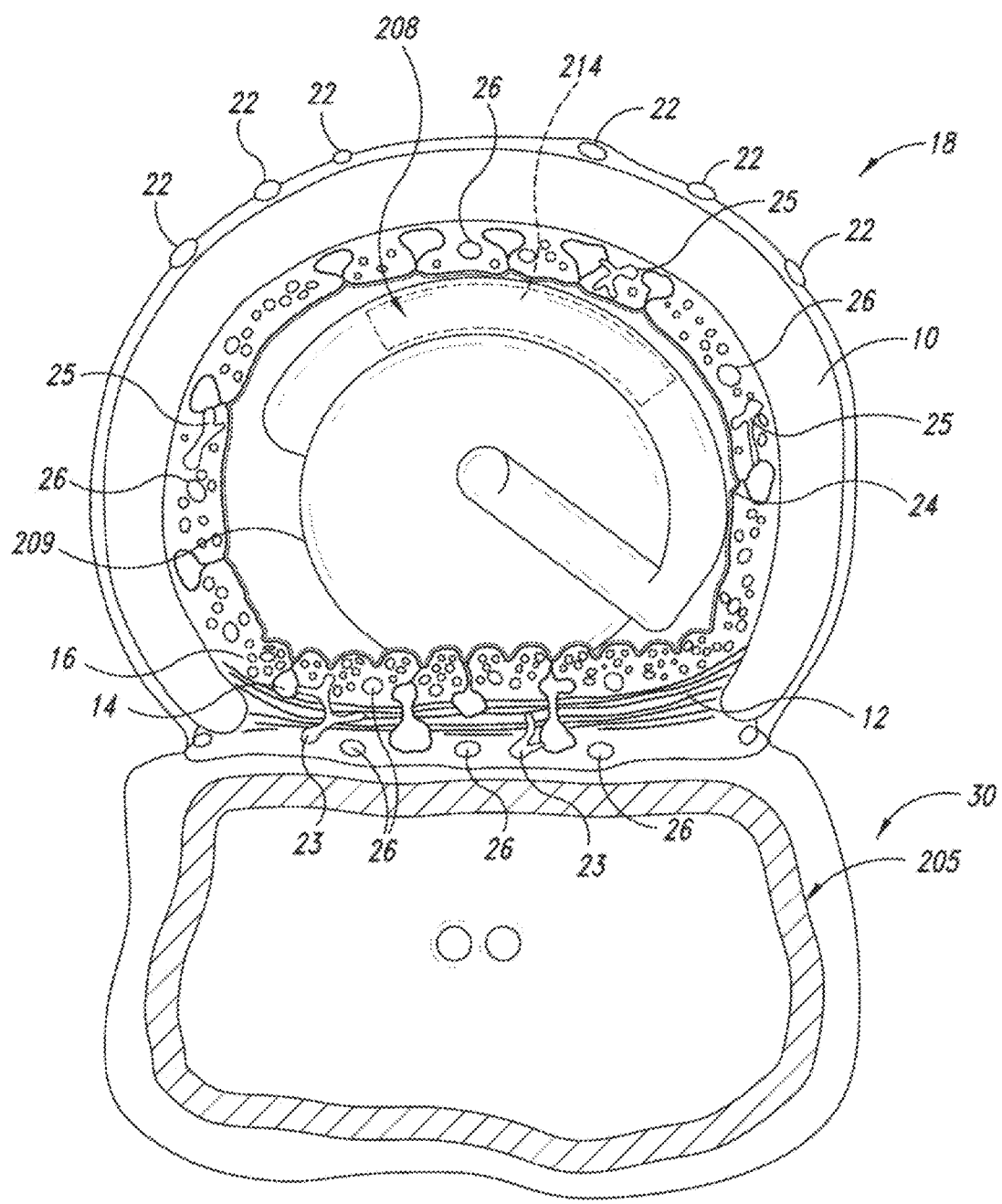
FIG. 9 illustrates a tracheal treatment device and an esophageal treatment device.

The RF electrode 214 can be positioned at other locations. FIG. 9 shows the RF electrode 214 positioned to target the right anterior plexus 22. After each application of energy, the energy delivery assembly 208 can be angularly rotated to treat a different section of the trachea wall. In some procedures, an entire circumference of the trachea wall 18 can be treated. In other embodiments, circumferential segments of the trachea wall 18 are treated to target specific tissue while minimizing tissue damage of adjacent sections of the trachea wall. Throughout the procedure, the temperature control device 205 can cool the esophageal tissue.

Different amounts of energy can be delivered to different sections of the trachea 18. Energy delivered at a first power level from the electrode 214 can create a first lesion covering a first portion of a circumference of the airway. Energy delivered at a second power level from the electrode 214 can create a second lesion covering a second portion of the circumference of the airway displaced from the first portion. The first power level is substantially different (e.g., greater) than the second power level. For example, the second power level can be about 40% to about 90% of the first power level, more preferably about 50%-80% of the first power level. The second power level can be selected to avoid permanent injury to non-target tissue proximate to the treatment site. The second portion can be circumferentially or axially displaced from the first portion relative to lumen of the airway. The first portion of the circumference can be on an anterior aspect of the airway, and the second portion can be on a posterior aspect of the airway.

Because the anterior region of the trachea 18 is spaced well apart from the esophagus 30, a higher amount of energy can be used to ablate the pulmonary plexus 22. As the electrode 214 is rotated towards the esophagus 30, the amount of emitted energy can be reduced. This can help minimize, limit, or substantially eliminate tissue damage to the esophageal tissue. Different amounts of energy can be delivered to different regions (e.g., circumferential locations) of the trachea 18. A relatively high amount of energy can be delivered to the anterior region of the trachea 18 as compared to the amount of energy delivered to the posterior region of trachea 18. A lower amount of energy can be delivered to the posterior tissue of the trachea 18 to avoid damage to esophagus tissue. In some protocols, about 20 watts of energy is delivered to electrode 214 to ablate tissue located at the anterior region of the trachea 18. The electrode 214 can emit no more than about 15 watts of energy when it is positioned to contact the posterior region of the trachea 18. In various procedures, the amount of energy delivered to the electrode 214 can be at least about 40% but less than 90% of the energy delivered to the electrode 214 at a different region of the trachea 18. In certain embodiments, the amount of energy emitted by the electrode 214 positioned along the posterior portion of the trachea 18 is in a range of about 50% to about 80% of the energy delivered to the electrode 214 positioned at the anterior portion of the trachea 18. In other embodiments, the amount of energy emitted by the electrode 214 positioned along the posterior portion of the trachea 18 is in a range of about 60% to about 90% of the energy delivered to the electrode 214 positioned at the anterior portion of the trachea 18. Other relative percentages are also possible.

As the mainstem bronchi pass from the lung root at the main carina out towards the lungs, a variety of external structures lie in close proximity to their outer surfaces. Anteriorly, these external structures are the pulmonary arteries and veins, aorta and superior vena cava; medially they are the soft tissues of the mediastinum and the heart; laterally the external structure is the lung parenchyma; posteriorly on the right it is again lung parenchyma; proximally on the left it is the esophagus; and distally it is the lung. Additionally, the continuation of the left main vagus nerve as it passes inferiorly to innervate the abdomen and pelvis is interposed between the esophagus and the left main bronchi.

Due to the high rate of blood flow through the blood vessels and the heart, these structures are effective heat sinks and much of the heat generated during treatment is removed from their walls during treatment. Thus, the walls of the blood vessels and of the heart are relatively unaffected by the treatment. The mediastinal soft tissues and the lung lack the heat sinking effect seen in the blood vessels and heart, but they may tolerate thermal injury without untoward clinical consequences. However, the esophagus and interposed vagus nerve lack significant blood flow and may be susceptible to thermal injury during treatment in the left mainstem bronchus.

In one procedure, the treatment site to which RF energy is applied is the most distal centimeter of the left mainstem bronchus. Because the esophagus 30 runs along the posterior aspect of the proximal portion of the left mainstem bronchus, at this most distal aspect of the bronchus, the posterior wall is in contact with lung parenchyma only. Thus, the RF energy can be delivered to the most distal centimeter of the left mainstem bronchus to avoid injury to the esophagus 30. Other types of energy can also be delivered to this location.

In another procedure, the posterior wall of the left mainstem bronchus is either not treated or is treated with a lower dose of energy, while the remainder of the airway's circumference is treated with a higher dose of energy. When the balloon 212 of FIGS. 5 and 6 has a longitudinal length of about 8 mm to about 12 mm, the electrode 214 can be cooled with either room temperature water or iced water coolant passing through the electrode 214 and balloon 212. In certain procedures, the rate of flow of the water or coolant through the balloon 212 and the electrode 214 can be maintained at about 100 ml per minute for a treatment duration of about 120 seconds, while power levels are maintained at less than 15 W applied on the posterior wall of the mainstem bronchus to cause substantially no injury to the esophagus 30 or the interposed vagus nerve. Other combinations of electrode size, coolant, coolant temperature, coolant flow, treatment duration and power could be used to achieve the same results.

Figure 10:
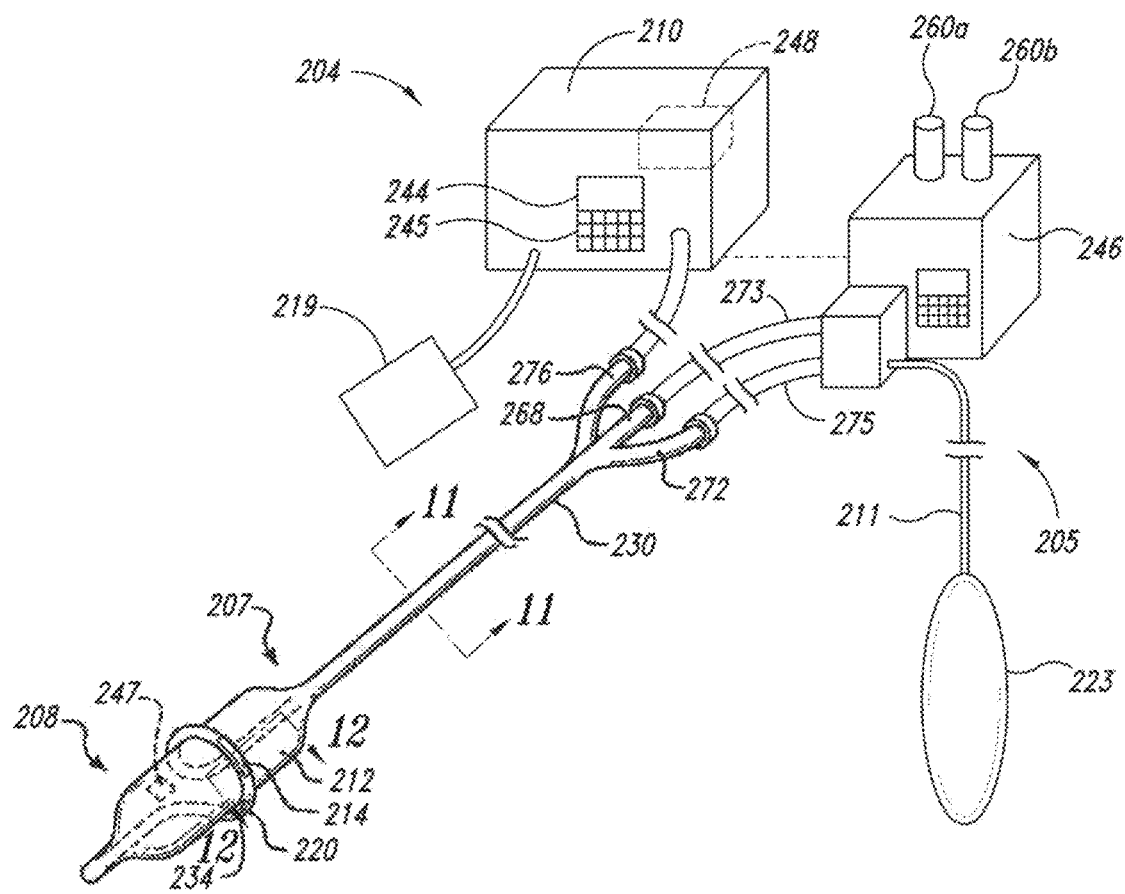
FIG. 10 is an isometric view of a treatment system.

Referring to FIG. 10, the treatment system 204 includes a media delivery system 246 and a control module 210 coupled to an elongate member in the form of a shaft 230 of the catheter 207. The temperature control device 205 is coupled to the media delivery system 246. An electrode pad 219 for placement against the patient is connected to the control module 210. Energy delivery assembly 208 comprises an emitter assembly 220 extending from the elongate shaft 230 and wrapping around a balloon 212. The balloon 212 can be inflated from a collapsed state (see FIG. 15) to the expanded state shown in FIG. 10. As the balloon 212 inflates, the electrode 214 can be moved towards the airway wall. The fully inflated balloon 212 can hold the electrode 214 near (e.g., proximate or in contact with) tissue through which energy is delivered. The coolant can absorb thermal energy to cool the balloon 212 or the energy emitter assembly 220, or both. This in turn cools the outer surface of the airway wall.

The control module 210 can include, without limitation, one or more computers, processors, microprocessors, digital signal processors (DSPs), field programmable gate arrays (FPGA), computing devices, and/or application-specific integrated circuits (ASICs), memory devices, buses, power sources, and the like. For example, the control module 210 can include a processor in communication with one or more memory devices. Buses can link an internal or external power supply to the processor. The memories may take a variety of forms, including, for example, one or more buffers, registers, random access memories (RAMs), and/or read-only memories (ROMs). Programs, databases, values, or other information can be stored in memory. For example, in some embodiments, the control module 210 includes information associated with tissue characteristics. A comparison can be performed between sensed tissue characteristics and stored tissue characteristics. Operation of the catheter 207 can be adjusted based, at least in part, on the comparison. Different types of reference values (e.g., reference values for non-treated tissue, reference values for treated tissues, impedance values, etc.) corresponding to tissue characteristics can be utilized in such a protocol. The control module 210 may also include a display 244, such as a screen, and an input device 245. The input device 245 can include one or more dials, knobs, touchpads, or a keyboard and can be operated by a user to control the catheter 207. Optionally, the input device 245 can also be used to control operation of the temperature control device 205.

The control module 210 can store different programs. A user can select a program that accounts for the characteristics of the tissue and desired target region. For example, an air-filled lung can have relatively high impedance, lymph nodes have medium impedance, and blood vessels have relatively low impedance. The control module 210 can determine an appropriate program based on the impedance. A differential cooling program can be executed to deliver different temperature coolants through the balloon 212 and the emitter assembly 220. The temperature difference can be at least 10° C. Performance can be optimized based on feedback from sensors that detect temperatures, tissue impedance, or the like. For example, operation of the energy delivery assembly 208 can be controlled based on a surface temperature of the tissue to which energy is delivered. If the surface temperature becomes excessively high, cooling can be increased and/or electrode power decreased in order to produce deep lesions while protecting surface tissues.

The control module 210 can function as an energy generator, such as a radio frequency (RF) electrical generator. RF energy can be outputted at a desired frequency. Example frequencies include, without limitation, frequencies in a range of about 50 KHZ to about 1,000 MHZ. When the RF energy is directed into tissue, the energy is converted within the tissue into heat causing the temperature of the tissue to be in the range of about 40° C. to about 99° C. The RF energy can be applied for about 1 second to about 120 seconds. In some embodiments, the RF generator has a single channel and delivers approximately 1 to 25 watts of RF energy and possesses continuous flow capability. Other ranges of frequencies, time intervals, and power outputs can also be used. An internal power supply 248 can be an energy storage device, such as one or more batteries. Electrical energy can be delivered to the energy emitter assembly 220, which converts the electrical energy to RF energy or another suitable form of energy. Other forms of energy that may be delivered include, without limitation, microwave, ultrasound, direct current, or laser energy. Alternatively, cryogenic ablation may be utilized wherein a fluid at cryogenic temperatures is delivered through the shaft 230 to cool a cryogenic heat exchanger on the assembly 208.

Referring again to FIGS. 5 and 10, the control module 210 can have one or more communication devices to wirelessly, optically, or otherwise communicate with the media delivery system 246. Pumps of the media delivery system 246 can be operated based on the signals. In other embodiments, the control module 210 can include the media delivery system 246. A single unit can therefore control operation of the catheter 207 and the temperature control device 205.

The media delivery system 246 can pump cooling media through the pulmonary treatment device 207 and the temperature control device 205 and includes a media container 260a coupled to a supply line 268 and a media container 260b coupled to a return line 272. Luer connectors or other types of connectors can couple the lines 268, 272 to lines 273, 275. The media container 260a can include a container (e.g., a bottle, a canister, a tank, a bag, or other type of vessel for holding fluid or other media). In pressurizable embodiments, the media container 260a includes one or more pressurization devices (e.g., one or more pumps, compressors, or the like) that pressurize coolant. Temperature control devices (e.g., Peltier devices, heat exchangers, or the like) can cool or recondition the fluid. The media can be a coolant including saline, deionized water, refrigerant, cryogenic fluid, gas, mixtures thereof, or the like. In other embodiments, the media container 260a can be an insulated container that holds and delivers a chilled coolant to the supply line 268. In embodiments, the media container 260a is bag, such as an IV type bag, configured to be held on a pole.

The balloon 212 optionally has a sensor 247 (illustrated in dashed line in FIG. 10) that is communicatively coupled to the control module 210. The control module 210 can command the catheter 207 based on signals from the sensor 247 (e.g., a pressure sensor, a temperature sensor, a thermocouple, a pressure sensor, a contact sensor, an impedance sensor, or the like). Sensors can also be positioned on energy emitter assembly 220, along the elongate shaft 230, or at any other location. In a closed loop system, the electrical energy is delivered to the electrode 214 based upon feedback signals from one or more sensors configured to transmit (or send) one or more signals indicative of one or more tissue characteristics, energy distribution, tissue temperatures, or any other measurable parameters of interest. Based on those readings, the control module 210 adjusts operation of the electrode 214. Alternatively, in an open loop system, the operation of the electrode 214 is set by user input. For example, the user can observe tissue temperature or impedance readings and manually adjust the power level delivered to the electrode 214. Alternatively, the power can be set to a fixed power mode. In yet other embodiments, a user can repeatedly switch between a closed loop system and an open loop system.

In certain procedures, the sensor 247 can sense one or more tissue characteristics. The control module 210 can analyze the sensed tissue characteristics. For example, the control module 210 compares at least one sensed tissue characteristic to at least one stored reference value to, for example, evaluate the location of the electrode 214 relative to the airway. The evaluation can include, without limitation, determining the position of the electrode 214 relative to a reference location. The control unit 210 can estimate the location of at least one non-target structure or tissue based on impedance and/or other measurable characteristic. After estimating the location of the non-target structure or tissue, the electrode 214 can be repositioned before delivering energy so as to avoid injury to the non-target structures or tissue. Previously treated tissue can be detected based on impedance and/or other measurable characteristics. The electrode 214 can be activated to treat the airway when it is determined that the electrode 214 is located in the desired position.

Media flowing through the conduit 234 cools the electrode 214. Alternatively, flow diverters within the balloon 212 can direct some or all of the coolant in the balloon 212 towards the electrode 214 or a balloon sidewall and may provide a separate cooling channel for the electrode 214. In some embodiments, one or more cooling channels extend through the electrode 214 (e.g., electrode 214 may be tubular so that coolant can flow through it). In other embodiments, the coolant flows around or adjacent the electrode 214. For example, an outer member, illustrated as the conduit 234 in FIG. 10, can surround the electrode 214 such that fluid can flow between the electrode 214 and the conduit 234. Additionally or alternatively, the energy delivery assembly 208 can be actively cooled or heated using one or more thermal devices (e.g., Peltier devices), cooling/heating channels, or the like.

Figure 11:
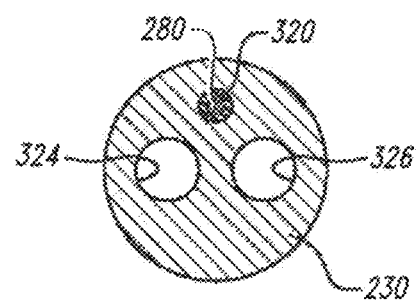
FIG. 11 is a cross-sectional view of a tracheal catheter taken along a line 11-11.

Referring to FIGS. 10 and 11, the elongate shaft 230 extends from the control module 210 to the energy delivery assembly 208 and includes a power line lumen 320, a delivery lumen 324, and a return lumen 326. A power line 280 extends through the power line lumen 320 and couples the control module 210 to the electrode 214. The delivery lumen 324 provides fluid communication between the media container 260a and the energy emitter assembly 220 and balloon 212. The return lumen 326 provides fluid communication between the balloon 212 and/or electrode 214 and the fluid receptacle 260b. The elongate shaft 230 can be made, in whole or in part, of one or more metals, alloys (e.g., steel alloys such as stainless steel), plastics, polymers, and combinations thereof, as well as other biocompatible materials, and can be flexible to pass conveniently along highly branched airways. Sensors can be embedded in the elongate shaft 230 to detect the temperature of the fluids flowing therethrough.

Figure 12:
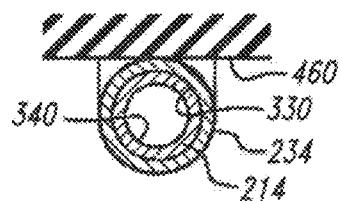
FIG. 12 is a cross-sectional view of the tracheal catheter taken along a line 12-12.

FIG. 12 shows the electrode 214 positioned in a channel 330 of the conduit 234 and includes a coolant channel 340. The electrode main body 350 can be a rigid tube made, in whole or in part, of metal (e.g., titanium, stainless steel, or the like). In some embodiments, conduit 234 does not extend over the entire electrode 214, leaving a central portion of the tubular electrode exposed for direct contact with the airway wall. In other embodiments, the electrode main body 350 is made, in whole or in part, of a shape memory material. Shape memory materials include, for example, shape memory metals or alloys (e.g., Nitinol), shape memory polymers, ferromagnetic materials, combinations thereof, and the like. These materials can assume predefined shapes when released from a constrained condition or different configurations when activated with heat. In some embodiments, the shape memory material can be transformed from a first preset configuration to a second preset configuration when activated (e.g., thermally activated).

Figure 13:
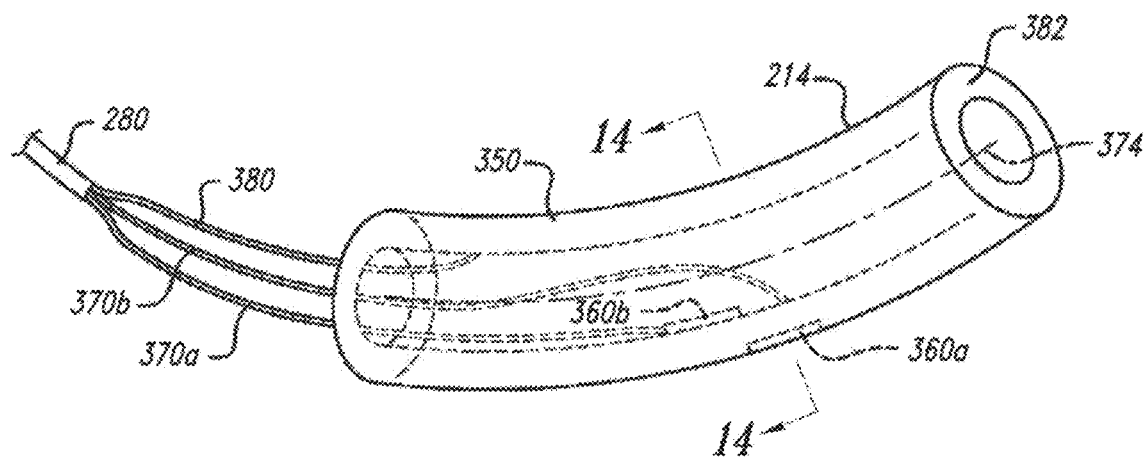
FIG. 13 is an isometric view of an electrode assembly.
Figure 14:
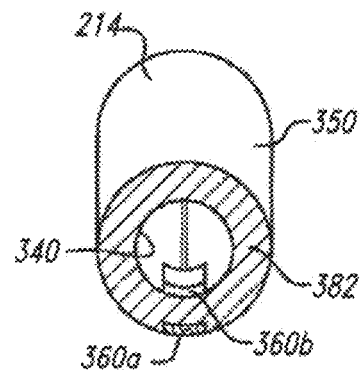
FIG. 14 is a cross-sectional view of the electrode assembly of FIG. 13 taken along a line 14-14.

As shown in FIGS. 13 and 14, sensors 360a, 360b (collectively "360") are coupled to the electrode main body 350. A pair of lines 370a, 370b (collectively "370") pass through the channel 340 and are coupled to the sensors 360a, 360b, respectively. In some embodiments, the sensor 360a is a contact sensor, and the sensor 360b is a temperature sensor, impedance sensor, and/or a pressure sensor. The number, positions, and types of sensors can be selected based on the treatment to be performed.

In multilayer embodiments, the electrode main body 350 can include at least one tube (e.g., a non-metal tube, a plastic tube, etc.) with one or more films or coatings. The films or coatings can be made of metal, conductive polymers, or other suitable materials formed by a deposition process (e.g., a metal deposition process), coating process, etc., and can comprise, in whole or in part, silver ink, silver epoxy, combinations thereof, or the like.

Radio-opaque markers or other types of visualization features can be used to position the main body 350. To increase visibility of the electrode 214 itself, the electrode 214 may be made, in whole or in part, of radiographically opaque material.

Figure 15:
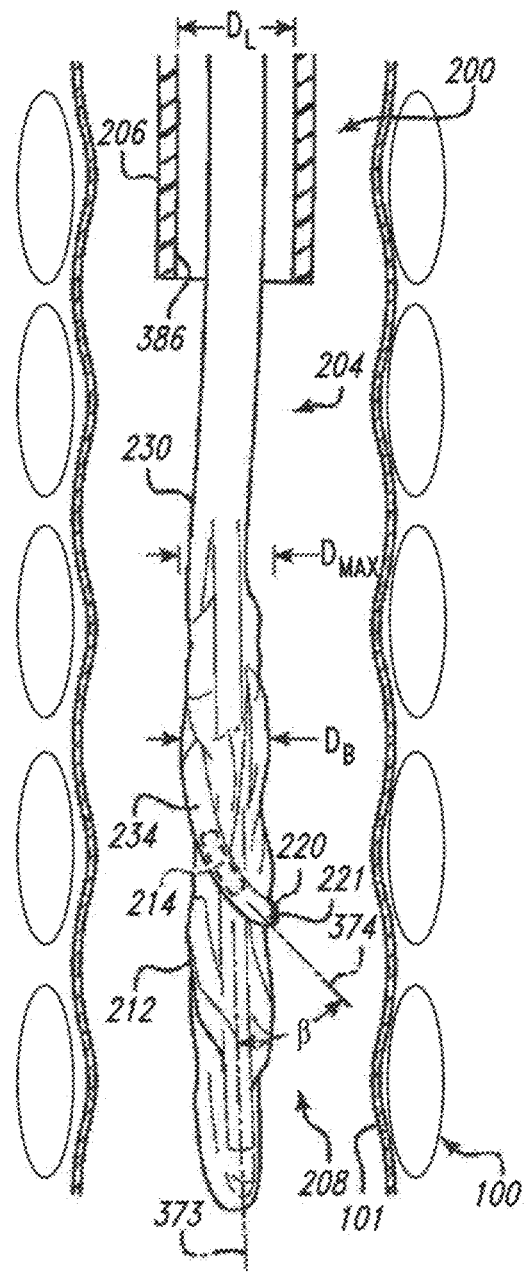
FIG. 15 is a partial cross-sectional view of a treatment system with a catheter extending out of a delivery apparatus.
Figure 16:
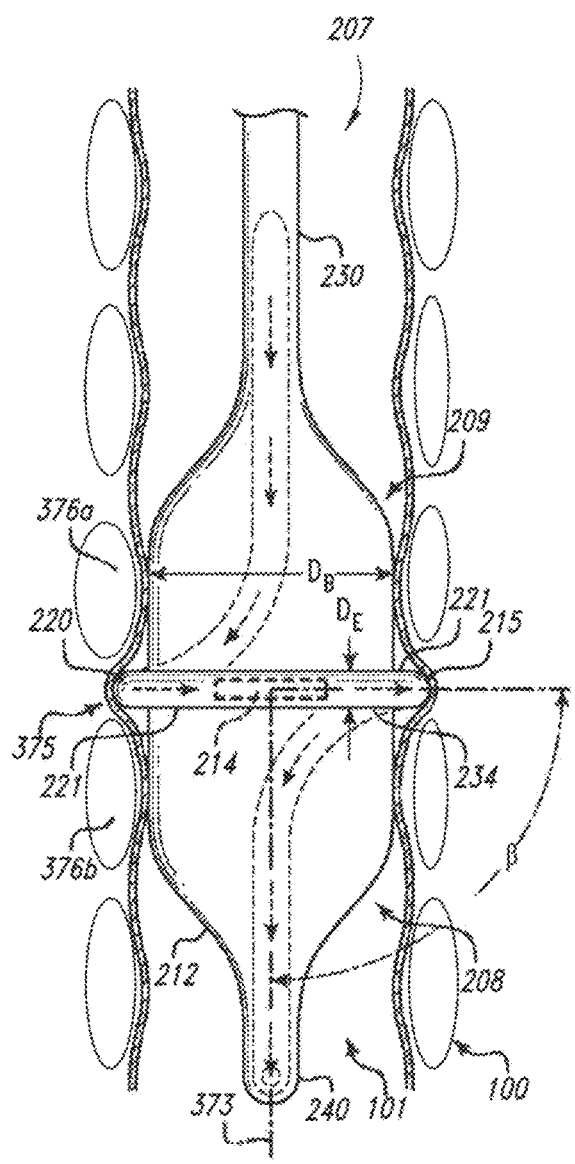
FIG. 16 is a side elevational view of a deployed energy delivery assembly with fluid flowing through an energy emitter assembly.
Figure 17:
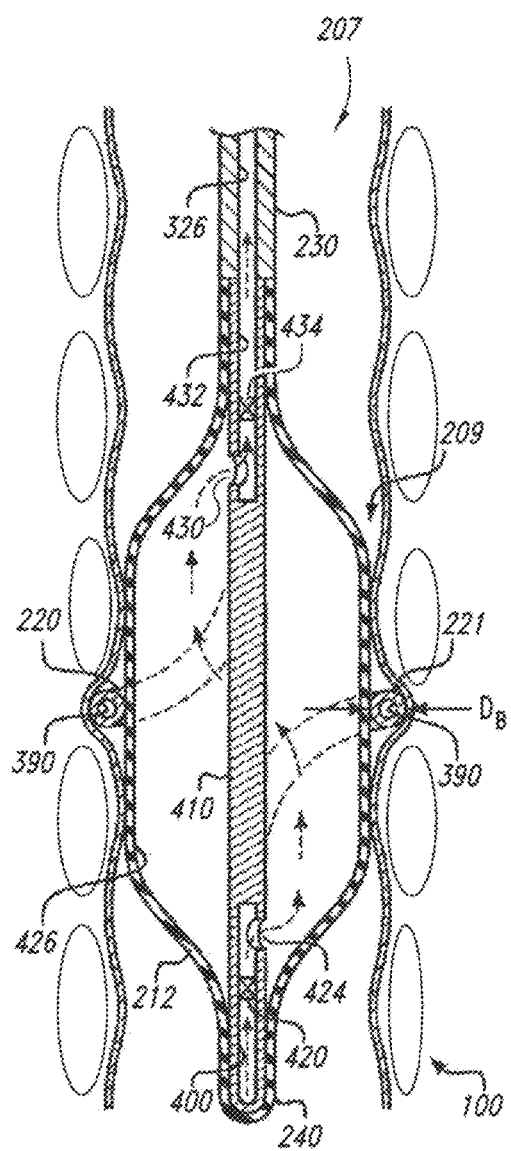
FIG. 17 is a cross-sectional view of the deployed energy delivery assembly with fluid flowing through an expandable member.

FIGS. 15-17 show one exemplary method of using a treatment system 200. A physician can visually inspect the airway 100 using a delivery apparatus 206 to locate and evaluate the treatment site(s) and non-targeted tissues before, during, and/or after performing a therapy. The airway 100 can be part of the trachea, main stem bronchi, or any other airway of the bronchial tree. A delivery apparatus 206 can be a bronchoscope, a guide tube, a delivery sheath, or an endoscope and can include one or more viewing devices, such as optical viewing devices (e.g., cameras), optical trains (e.g., a set of lenses), and the like. For example, the delivery apparatus 206 can be a bronchoscope having one or more lights for illumination and optical fibers for transmitting images. The catheter 207 may be adapted to be delivered over a guidewire (not shown) that passes between the balloon 212 and the energy emitter assembly 220. This provides for rapid exchange capabilities.

When the delivery apparatus 206 of FIG. 15 is moved along a body lumen 101 (e.g., an airway), the collapsed energy delivery assembly 208 is held within a working channel 386 of the delivery apparatus 206. The conduit 234 can form a loop 221 such that the electrode 214 is almost parallel to a long axis 373 when the catheter 207 is in a substantially straight configuration. In the illustrated embodiment of FIG. 15, an angle β is defined between the direction of the long axis 373 of the catheter 207 and a long axis 374 of the electrode 214. The angle β can be in a range of about 0 degrees to about 30 degrees. In some embodiments, the angle β is in a range of about 0 degrees to about 20 degrees. The electrode 214, being curved, can also nest with and partially encircle the elongate shaft 230. In certain embodiments, at least a portion of the elongate shaft 230 is disposed within an arc of the electrode 214 for a further reduced profile. As such, the shaft 230 can be positioned between the ends of the electrode 214. Electrode 214 may have various lengths, depending on the desired length of the lesion to be created in each electrode position. In preferred embodiments, electrode 214 has a length of at least about 1 mm to about 4 mm. In certain embodiments, the length of the electrode 214 is about 2 mm up to about 3 mm. The electrode can have a width (or diameter if cylindrical) no larger than the width of the spaces between the cartilage rings, in some embodiments being about 0.1 mm to about 3 mm.

With continued reference to FIG. 15, the diameter $D_L$ of the working channel 386 can be less than about 8 mm. The diameter $D_B$ of the deflated balloon 212 can be relatively small. For example, a minimum diameter $D_{B\ min}$ can be in a range of about 2 mm to about 3 mm, and a maximum diameter $D_{B\ max}$ in a range of about 5 mm to about 6 mm when the balloon 212 is fully collapsed. If the electrode 214 is collapsible, the diameter $D_{max}$ of the assembly 208 can be less than about 3 mm. In ultra low-profile configurations, the maximum diameter $D_{max}$ can be less than about 2.8 mm.

The balloon 212 can be inflated to move the energy emitter assembly 220 near (e.g., proximate to or in contact with) the airway 100. The angle β can be increased between 70 degrees and about 110 degrees when the balloon 212 is fully inflated. FIG. 16 shows the energy delivery assembly 208 deployed, wherein the electrode 214 can be about perpendicular to the long axis 373. There can be play between the energy emitter assembly 220 and the balloon 212 such that the angle β is in a range of about 60 degrees to about 120 degrees in order to accommodate variations of anatomical structures, misalignment (e.g., misalignment of the catheter shaft 230), or the like. In some embodiments, the electrode 214 moves towards a circumferentially extending orientation as it moves from a delivery orientation to the deployed orientation. The electrode 214 in the deployed orientation extends substantially circumferentially along the wall of the airway 100. In certain embodiments, the electrode 214 will be configured to be positioned entirely within the spaces 375 between cartilage rings 376 along the airway wall when the energy delivery assembly 208 is in the fully deployed configuration.

FIGS. 16 and 17 show the energy emitter assembly 220 fluidically coupled to both the elongate shaft 230 and the balloon 212. Generally, coolant cools the tissue-contacting portion of the energy emitter assembly 220. The cooling section 209 of the energy delivery assembly 208 contacts the airway wall 100 so as to cool tissue adjacent to the tissue-contacting portion while energy is outputted by the electrode 214. The cooling section 209 can be formed by the portions of the energy emitting assembly 220 and the balloon 212 that contact the airway wall 100. If the electrode 214 faces an anterior region of the trachea 18, the assembly 208 can seat between cartilage rings 376 to avoid or limit movement of the electrode 214 along the length of the airway 100. If the energy delivery assembly 208 is positioned in the bronchial tree, especially in the main stem bronchi, the electrode 214 can be seated between spaced apart cartilage rings 376.

As the balloon 212 inflates, the electrode 214 moves (e.g., pivots, rotates, displaces, etc.) from a first orientation of FIG. 15 in which the electrode 214 extends axially along the airway 100 and a second orientation of FIG. 16 in which the entire electrode 214 is disposed in a space 375 between adjacent cartilage rings 376a, 376b. The balloon 212 can both cool the airway 100 and cause the electrode 214 to seat in the space 375.

FIG. 16 shows the energy emitter assembly 220 positioned to locate the electrode 214 in the space 375. In certain embodiments, the electrode 214, in the first orientation, extends a distance with respect to a longitudinal axis 373 (see FIG. 15) that can be greater than the distance the electrode 214, in the second orientation, extends with respect to the longitudinal axis 373.

To deploy the energy emitting assembly 208, coolant from the elongate shaft 230 flows through the energy emitter assembly 220 and into the balloon 212. The electrode 214 can output a sufficient amount of energy to ablate a target region. The electrode 214 can be at a position corresponding to the anatomical location of at least one nerve in or proximate to the airway wall 100. The electrode 214 outputs energy to ablate the targeted nerve tissue. The coolant absorbs thermal energy from electrode 214 and the airway wall 100.

To treat tissue along the trachea, the diameter $D_E$ of the electrode 214 and conduit 234 can be in a range of about 1.5 cm to about 2 cm when pressurized with coolant. In some embodiments, the diameter $D_E$ of the electrode 214 and conduit 234 can be in a range of about 2 cm to about 2.5 cm to treat an average sized adult human. To treat tissue along one of the main stem bronchi, the diameter $D_E$ can be in a range of about 1.5 mm to about 2.5 mm. Such embodiments are well suited to treat tissue outside the lung along the main bronchi. In certain embodiments, the diameter $D_E$ is about 2 mm. In yet other embodiments, the diameter $D_E$ can be in a range of about 0.1 mm to about 3 mm. The diameter $D_E$ of the deflated conduit 234 and electrode 214 can be about 0.1 mm to about 1 mm. For example, to treat a bronchial tree of a human, the diameter of the inflated balloon 212 can be in a range of about 12 mm to about 18 mm. For enhanced treatment flexibility of the bronchial tree, the inflated balloon diameter may be in a range of about 7 mm to about 25 mm. Of course, the balloon 212 can be other sizes to treat other organs or tissue of other animals.

Figure 18:
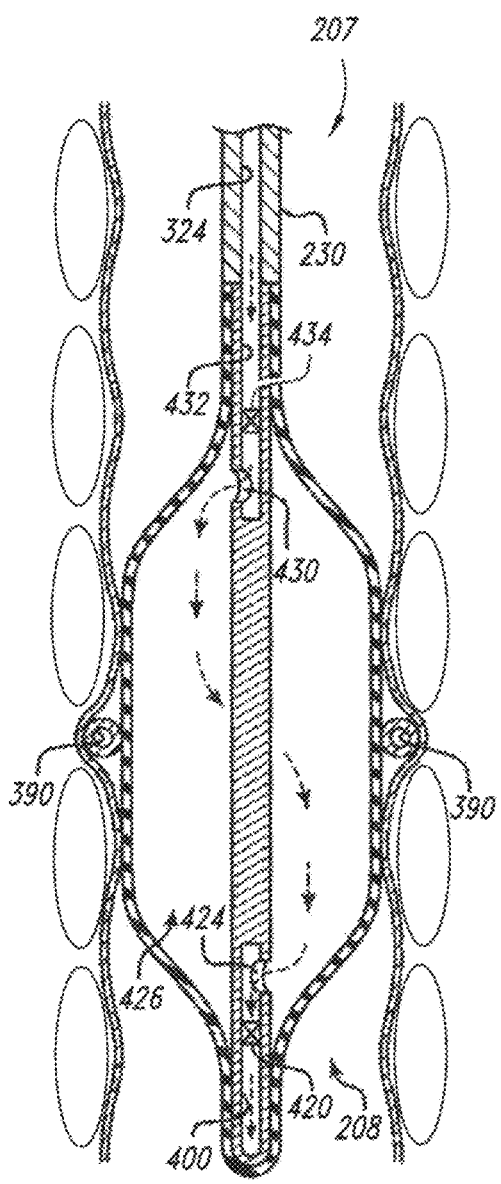
FIG. 18 is a cross-sectional view of the energy delivery assembly with fluid flowing into the expandable member.

The energy delivery assembly 208 provides differential cooling because the coolant in the energy emitter assembly 220 is at a lower temperature and a higher velocity than the coolant in the balloon 212. Coolant, represented by arrows, flows out of the elongate shaft 230 and into the energy emitter assembly 220. The coolant proceeds through the energy emitter assembly 220 and the coolant channel 340 (FIG. 14) of the electrode 214. The coolant absorbs thermal energy from the electrode 214. The heated coolant flows into the tip 240 and proceeds proximally through a lumen 400, as shown in FIG. 18. The coolant flows through a valve 420 (e.g., a throttle) and passes through a port 424. The valve 420 is disposed along a fluid path connecting the energy emitting assembly 220 and the portion of the balloon 212 defining the cooling section 209. The coolant circulates in a chamber 426 and absorbs heat from the tissue. This helps keep shallow tissue below a temperature that would cause cell death or tissue damage.

The coolant flows through a port 430, a lumen 432, and a throttle 434. The throttles 420, 434 can cooperate to maintain a desired pressure. The throttle 420 is configured to maintain a first flow rate of the coolant through the energy emitting assembly 220 and a second flow rate of the coolant through the cooling section 209. The first flow rate can be significantly different from the second flow rate.

The conduit 324 can assume a preset shape when pressurized. The valves 420, 434 can cooperate to maintain the desired pressure within the balloon 212 within a range of about 5 psig to about 15 psig. Such pressures are well suited to help push the electrode 214 between cartilaginous rings. Other pressures can be selected based on the treatment to be performed. The valves 420, 434 can be throttle valves, butterfly valves, check valves, duck bill valves, one-way valves, or other suitable valves.

When RF energy is transmitted to the electrode 214, the electrode 214 outputs RF energy that travels through tissue. The RF energy can heat tissue (e.g., superficial and deep tissue) of the airway wall while the coolant cools the tissue (e.g., superficial tissues). The net effect of this superficial and deep heating by RF energy and superficial cooling by the circulating coolant is the concentration of heat in the outer layers of the airway wall 100. Tissue structures can vary between different types of airways. In the bronchial tree, the temperature of the connective tissue can be higher than the temperatures of the epithelium, stroma, and/or smooth muscle. By example, the temperature of the connective tissue can be sufficiently high to cause damage to the nerve trunk tissue or other deep tissue while other non-targeted tissues of the airway are kept at a lower temperature to prevent or limit damage to the non-targeted tissues.

Heat can be concentrated in one or more of the internal layers (e.g., the stroma) of the airway wall or in the inner lining (e.g., the epithelium) of the airway wall. Furthermore, one or more of the vessels (e.g., vessels of the bronchial artery) may be within the lesion. The heat generated using the electrode 214 can be controlled such that blood flowing through the bronchial artery branches protects those branches from thermal injury while nerve trunk tissue is damaged, even if the nerve tissue is next to the artery branches. The catheter 207 can produce relatively small regions of cell death. For example, a 2 mm to 3 mm section of tissue in the middle of the airway wall 100, along the outer surface of the airway wall 100, or between the airway wall 100 and other body tissue (e.g., tissue of the esophagus) can be destroyed. By the appropriate application of power and the appropriate cooling, lesions can be created at any desired depth.

A circumferential lesion can be formed around all or most of the circumference of the airway wall 100 by ablating tissue while slowly rotating the energy delivery assembly 208 or by positioning the energy delivery assembly 208 in a series of rotational positions at each of which energy is delivered for a desired time period. Some procedures form adjacent lesions that become contiguous and form a circumferential band all the way around the airway wall 100. In some embodiments, the entire loop 221 (FIG. 16) can be an electrode. The loop 221 can be coated with a conductive material and can carry the electrode. A single procedure can produce a circumferential lesion. After forming the lesion, coolant flowing into the balloon 212 can be stopped. The balloon 212 is deflated causing the energy emitter assembly 220 to recoil away from the airway wall 100. The catheter 207 may be repositioned to treat other locations or removed from the subject entirely.

Figure 19:
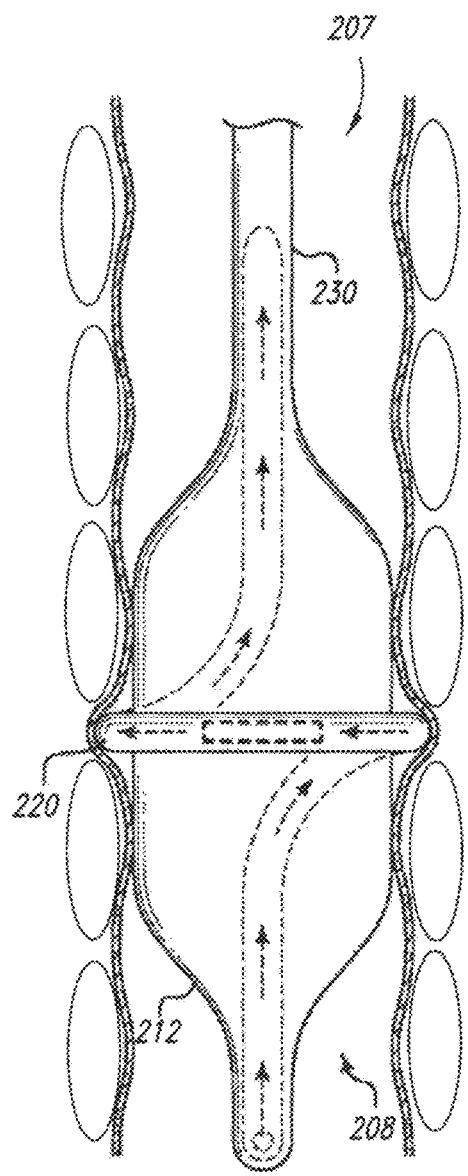
FIG. 19 is an elevational view of the ablation assembly with fluid flowing through the energy emitter assembly.

If the user wants the coolant in the balloon 212 to be at a lower temperature than the coolant in the energy emitter assembly 220, chilled coolant can be delivered into the balloon 212 and then into the energy emitter assembly 220. FIGS. 18 and 19 show such a coolant flow. Low temperature coolant flowing through the elongate body 230 passes through the valve 434 and the port 430. The coolant circulates in the chamber 426 and absorbs heat. The heated coolant flows through the valve 420 and proceeds through the energy emitter assembly 220 to cool the electrode 214.

Airway cartilage rings or cartilage layers typically have a significantly larger electrical resistance than airway soft tissue (e.g., smooth muscle or connective tissue). Airway cartilage impedes energy flow (e.g., electrical radio frequency current flow) and makes the formation of therapeutic lesions with radio frequency electrical energy to affect airway nerve trunk(s) challenging when the electrode is next to cartilage.

Positioners can facilitate positioning of the electrodes. Such positioners include, without limitation, bumps, bulges, protrusions, ribs or other features that help preferentially seat the electrode 214 at a desired location, thus making it easy to perform the treatment or to verify correct positioning. FIGS. 20 and 21 show the energy emitter assembly capable of serving as an intercartilaginous positioner. When the balloon 212 presses against the airway 100, the loop 221 moves along the balloon 212 to preferentially position the electrodes 214 between cartilage rings 452a, 452b. The loop 221 protrudes outwardly from the balloon 212 a sufficient distance to ensure that the energy delivery assembly 208 applies sufficient pressure to the airway wall to cause self-seating. The catheter 207 can be moved back and forth to help position the electrodes 214 next to soft compliant tissue 453 in the space 453. The energy emitter assembly 220 can be configured to displace a distance $D_o$ (e.g., measured along a long axis 310), which is at least half of the distance D between the cartilage rings 452a, 452b. This ensures that the electrodes 214 can be positioned generally midway between the cartilage rings 452a, 452b.

The plurality of electrodes 214 can reduce both treatment time and procedure complexity as compared to a catheter with a single electrode. This is because the multi-electrode catheter may have to be positioned a smaller number of times within a bronchial tree (or other hollow organ) as compared to single electrode catheters to produce a number of lesions of a desired therapeutic size. Multi-electrode catheters can thus precisely and accurately treat a user's respiratory system.

Figure 22:
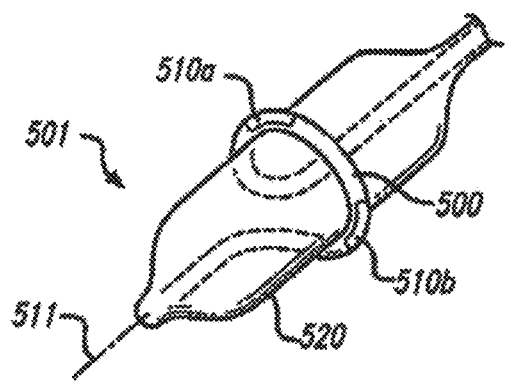
FIG. 22 is an isometric view of an ablation assembly with a pair of electrodes.
Figure 23:
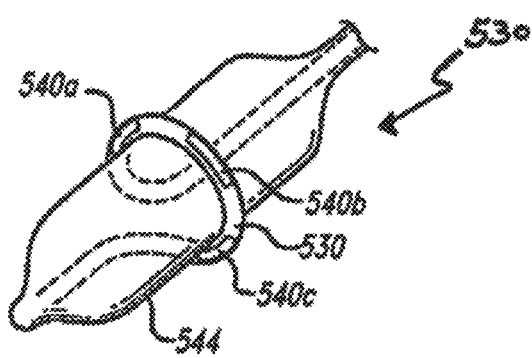
FIG. 23 is an isometric view of an ablation assembly with three electrodes.

FIG. 22 shows an energy emitter assembly 500 that includes two energy delivery elements including electrodes 510a, 510b spaced apart from one another about a circumference of a balloon 520. The electrodes 510a, 510b can be about 45 degrees to 210 degrees from another with respect to a long axis 511 of an ablation assembly 501. Other electrode positions are possible. FIG. 23 shows an energy emitter assembly 530 with three energy delivery elements 540a, 540b, 540c positioned about 60 degrees from one another. In these embodiments, each electrode may be coupled to separate power lines to allow for independent control of each, or all electrodes may be coupled to the same power line so as to be operated together. Further, a pair of electrodes may be operated in a bipolar manner, wherein one electrode is positive and the other negative, with RF power being transmitted from one to the other through the tissue.

Figure 24A:
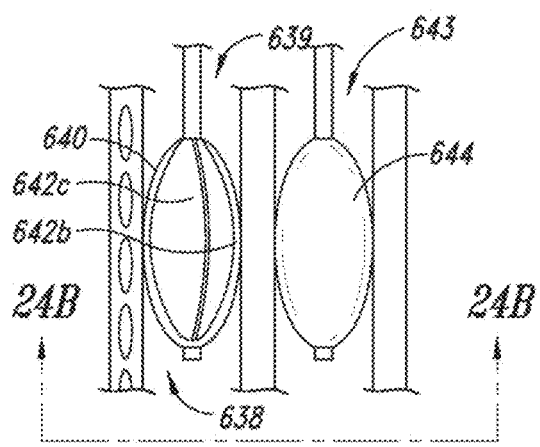
FIG. 24A is a schematic view of a treatment system employing monopolar electrodes for pulmonary treatment and an esophageal device in a subject.
Figure 24B:
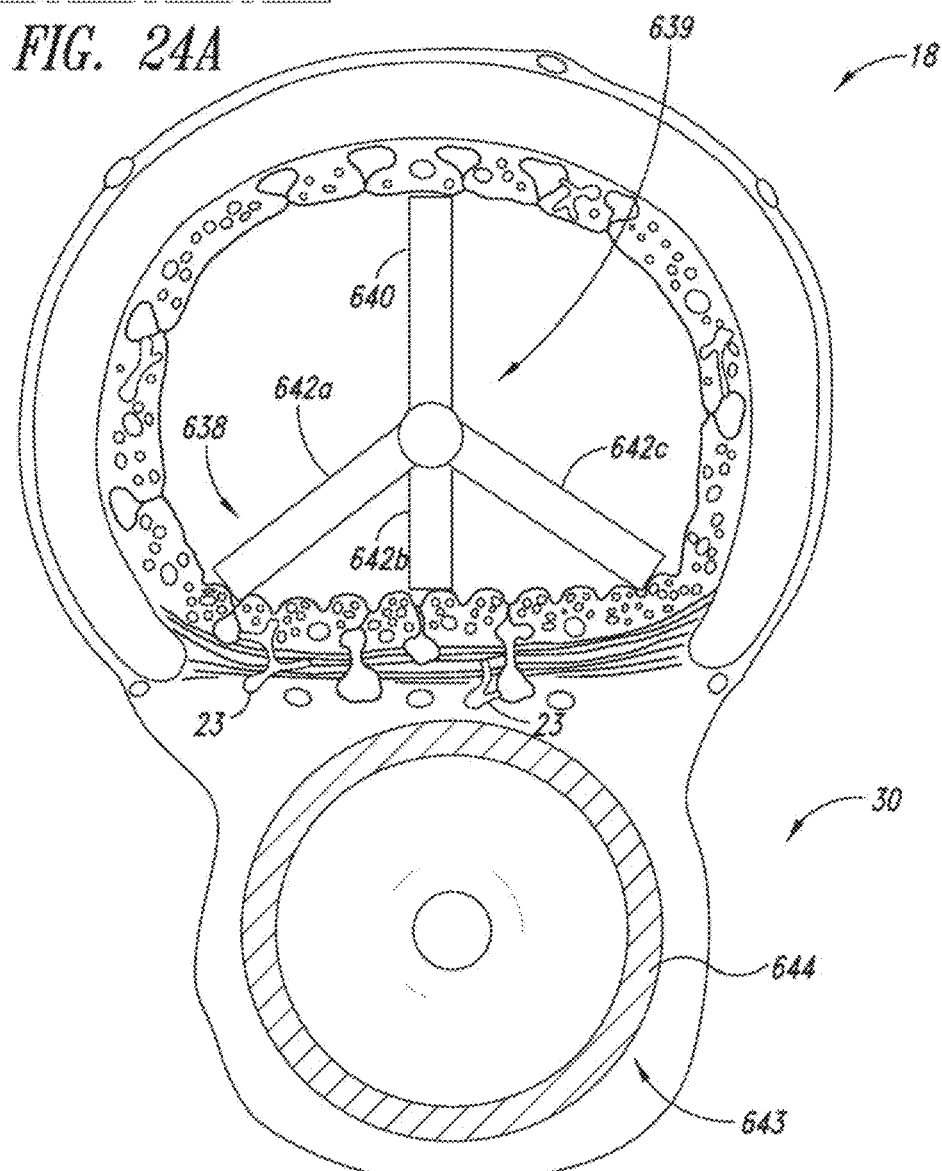
FIG. 24B is a schematic view of an embodiment of the present invention employing monopolar electrodes for treatment.

FIGS. 24A and 24B illustrate a portion of a treatment apparatus in the form of a tracheal device 639 in a delivered configuration for treating the trachea 18 in a monopolar fashion. The tracheal device 639 includes a basket 638 with a positioning member 640 and electrode members 642a, 642b, 642c (collectively "642"). The electrode members 642 can cooperate to treat the posterior plexus nerves 23. In this instance, an active device is placed in the trachea, with a ground pad placed on the patient's skin, typically in the thigh area. In order to prevent damage to the esophagus 30, a cooling or protection device is inserted into the esophagus 30. This device can be inserted through the mouth, or preferably, trans-nasally. The trans-nasal placement keeps the device separated from the manipulations of the device, to be placed in the trachea.

The basket 638 can be a cage or other type of self-expanding device. Advantageously, the basket 638 can be moved from a low profile (or collapsed configuration) to deployed state (or an expanded configuration) without the use of a balloon. Such non-inflatably expandable embodiments can be made of one or more shape memory materials (e.g., Nitinol) capable of assuming different configurations. Additionally or alternatively, the basket 638 can be actuated using one or more pull wires or similar components.

A protection device in the form of a catheter 643 has a cooling balloon 644. In order for such an embodiment to efficiently circulate cooling media, the protection catheter 643 can include an inlet and an outlet to allow circulation of media (e.g., cooling media) through the balloon 644. The protective or cooling media is introduced through one lumen, allowed to inflate and circulate within the balloon 644, and exit through a second lumen. Additionally, the cooling media can be either gas or liquid, and can be chosen from a number of different varieties of either. Example gasses include room temperature or cooled air, nitrogen, cryogenic media, or the like. Example liquids include room temperature or cooled water, saline, ringer's solution, glucose solutions or the like.

Whereas FIGS. 24A, 24B referred to above describe a monopolar device with esophageal protection, FIGS. 25A and 25B illustrate one of a group of embodiments which will be called the trachea-to-esophagus, or T:E devices. In these embodiments, devices 666, 662 are inserted into the trachea 18 and esophagus 30, respectively. The devices 666, 662 cooperate to form a therapy and protection system encompassing the use of both devices to send and receive energy to the targeted tissue, and to protect the non-target tissue as well, as desired and required.

The protection or cooling media in the two different devices 666, 662 can be set up to maintain the same level of protection in both devices and both structures, or they may be set to provide differential cooling to one structure over another. For example, it may be desirable to cool the esophagus 30 more than the trachea 18, in order to provide greater protection to the esophagus 30, and in order to locate the lesion within the tissue bridge between the structures biased toward the trachea side of the bridge. This might better target the neural plexus specifically, while providing greater safety to the esophagus 30.

In FIGS. 25A and 25B, two devices 666, 662, which may be essentially the same in design, are inserted into each of the lumens (trachea and esophagus). The devices 666, 662 have an optional central lumen for guide wire guidance, a balloon with inflation lumens, and optionally, a second lumen for circulation of protective cooling media, and outer electrodes 667, 668. In the embodiments of FIGS. 25A and 25B, the outer electrodes 667, 668 are comprised of a cage of wires surrounding balloons 676, 678. Each cage can be deployed by the respective balloon 676, 678 directly, or they can be made of a suitable shape memory alloy to allow them to expand to contact the tissue independent of balloon action. The electrodes 667, 668 can be comprised of any suitable conductive material, including stainless steel, chromium cobalt, nickel titanium, metal-loaded conductive polymers, or the like. One of the devices can be attached to the energy delivery aspect of a delivery control box, and one acts as the return electrode. Depending on the specific energy density desired, the active device can placed in either the trachea 18 or the esophagus 30, and the return in the other. A cooled fluid may be circulated through balloons 676, 678 to absorb heat from energy delivery elements including electrodes 667, 668 and from the tissue of the esophageal and tracheal wall. During treatment, the balloons 676, 678 can be inflated to physically contact the inner surfaces of the trachea 18 and esophagus 30, respectively. The balloons 676, 678 have a generally circular shape as viewed along the lumen of the trachea 18, similar to the embodiments shown in FIG. 24B. The balloons 676, 678 can have transverse cross-sections that are substantially circular, elliptical, polygonal, or combinations thereof and can have a smoother exterior surface, roughened exterior surface, undulating or wavy exterior surface, or the like. The electrodes 667, 668 deliver energy directly to the tissue. In other treatments, the balloons 676, 678 can be smaller than the lumens of the trachea 18 and the esophagus 30.

Figure 26:
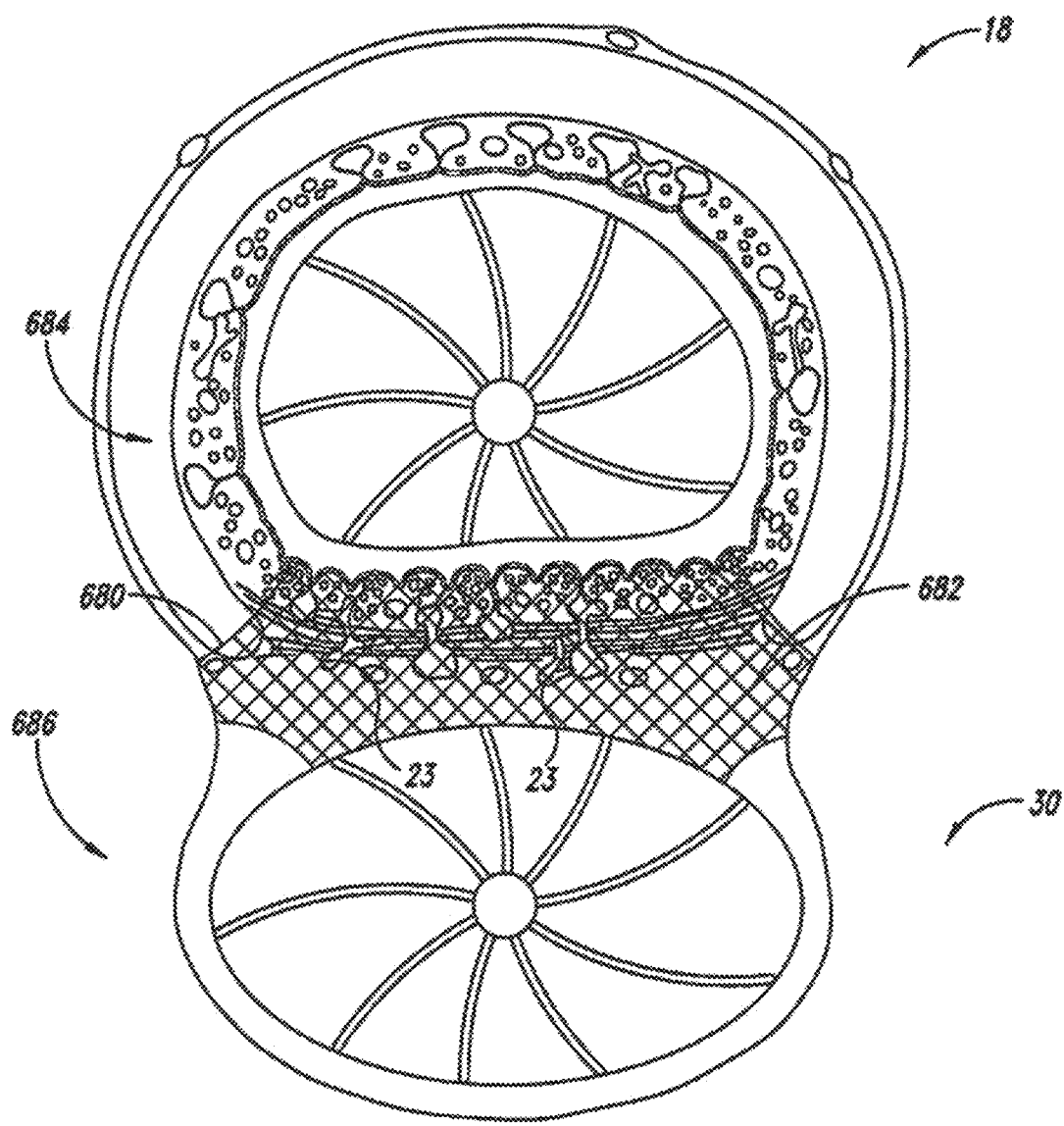
FIG. 26 illustrates a circumferential bipolar energy distribution possible with the embodiment of FIGS. 25A and 25B.

FIG. 26 shows the energy distribution around the esophagus 30 and trachea 18 as may be produced by a system as described in FIGS. 25A and 25B. An area of high energy density 680 (shown hatched) exists in the tissue bridge 682 between the two structures, with relatively lower energy density 684, 686 (shown non-hatched) in other tissues around the perimeter of each of the individual structures. Without cooling, the tissue of the high energy density region 680 is ablated or otherwise altered (e.g., damaged, destroyed, etc.) and preferably includes the posterior plexus nerves 23. In certain treatments, all of the posterior plexus nerves 23 between lumens of the trachea 18 and the esophagus 30 are damaged. In other treatments, targeted posterior plexus nerves 23 are damaged. If cooling media is circulated through one or both balloons, 676, 678, the tissue near the inner surface of the tracheal wall, as well as the tissue of the esophagus, can be protected from injury, while ablating target nerve tissues. Energy delivery and cooling may be adjusted to produce the isotherms of FIGS. 8A and 8B which are well suited for targeting damage to the interior tissue, such as the posterior plexus nerves 23, without damaging other tissue of the trachea 18, esophagus 30, and bridge 682.

Figure 27:
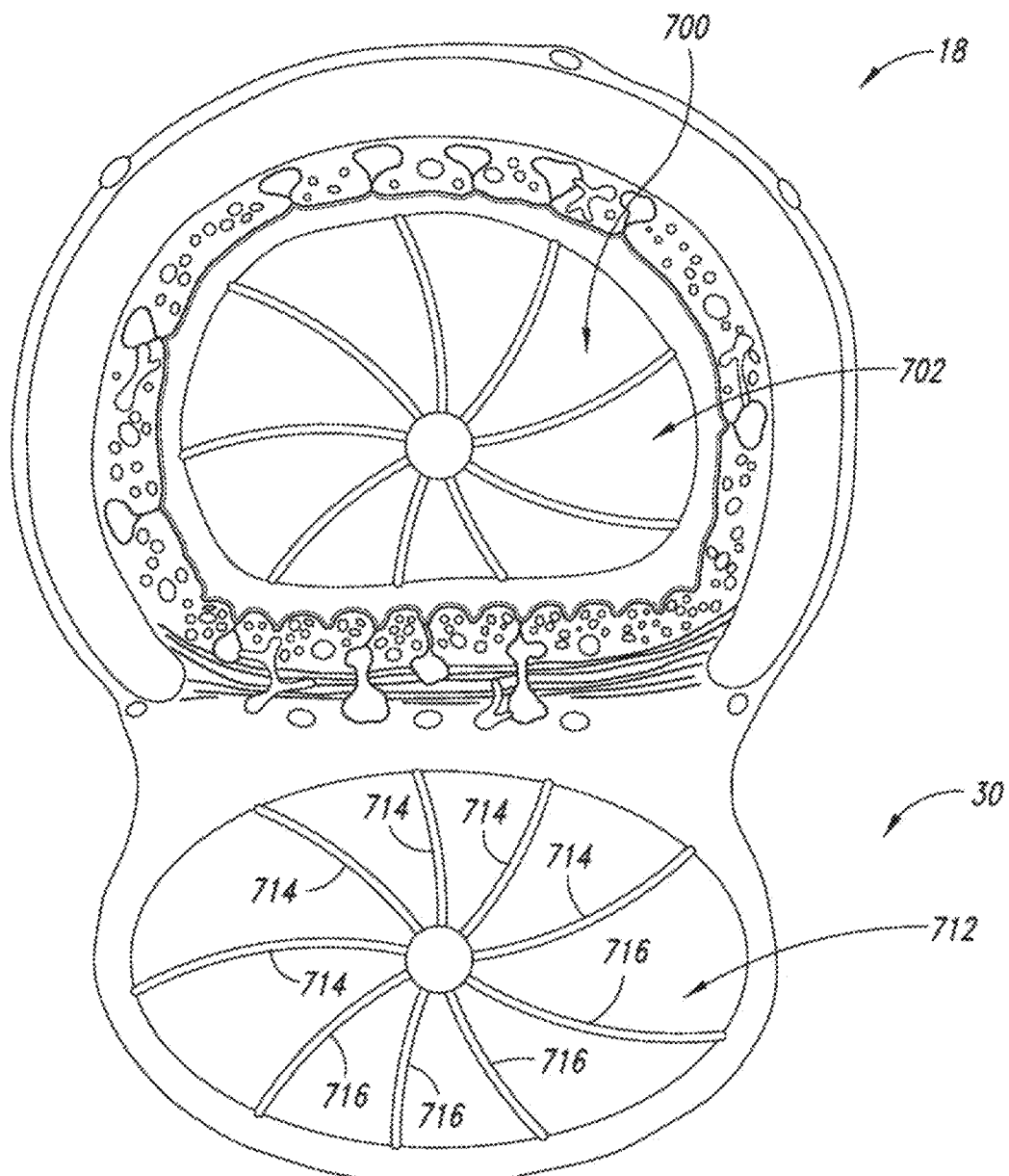
FIG. 27 is a schematic view of an embodiment employing trachea-to-esophagus bipolar, anterior esophageal return electrodes.

An embodiment designed to optimize energy density around the trachea 18 is shown in FIG. 27. In this embodiment, the active electrodes 700 of a device 702 are arranged around the entire circumference in the trachea 18, and the return electrodes 714 are disposed only on the anterior aspect of the esophageal device 712. In this case, the anteriorly oriented support electrodes 714 are conductive, while the posterior and optionally the posterior-lateral elements 716 are non-conductive. To render them non-conductive, they could simply be insulated from the return leads at the points of connection at the distal and proximal ends of the balloon, insulated over the length of the members via insulating shrink tubing, polymer coextrusion or coating, or made of completely non-conductive materials, such as an extruded polymer.

Figure 28:
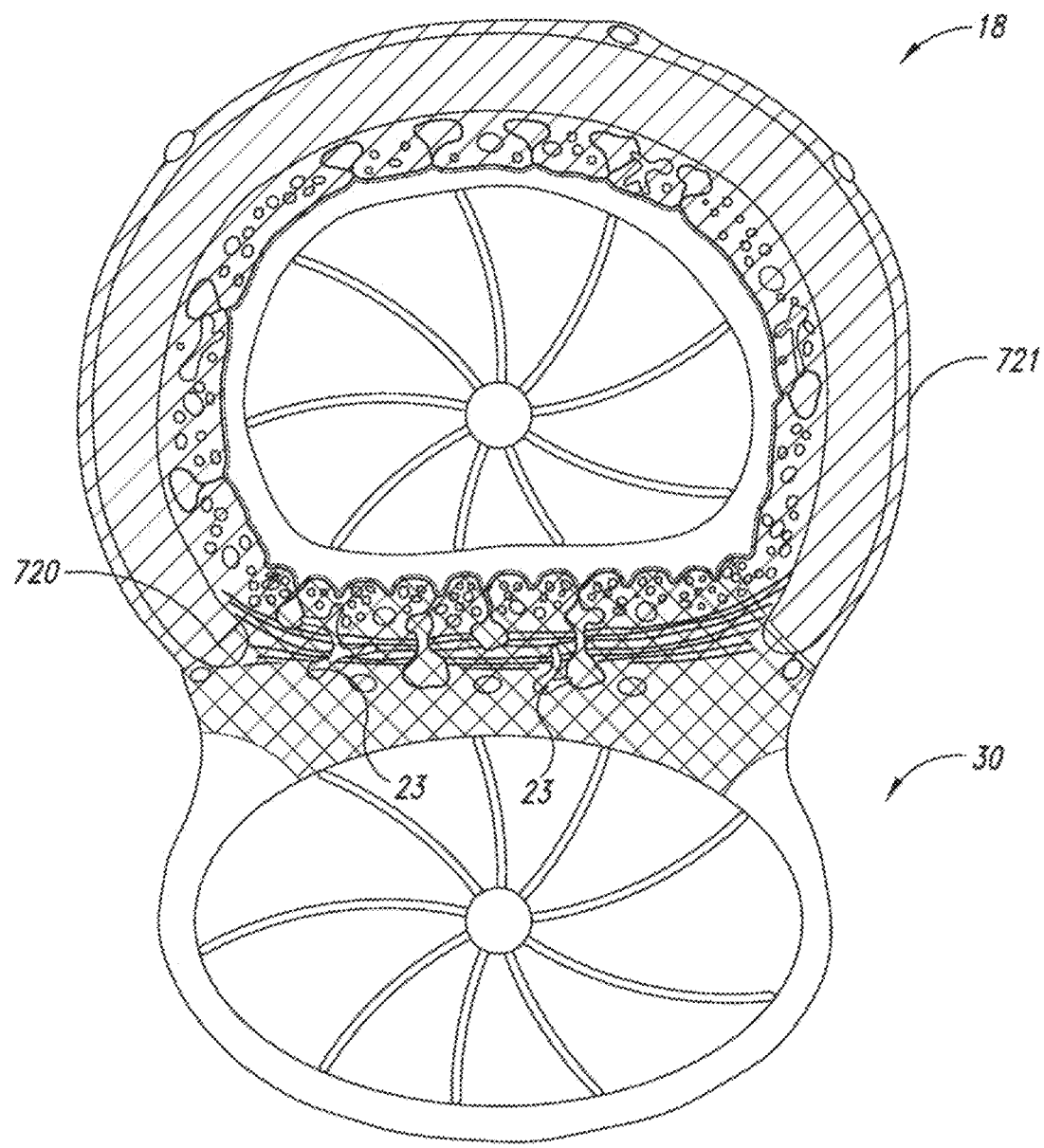
FIG. 28 illustrates a bipolar energy density distribution possible with the embodiment of FIG. 27.

FIG. 28 illustrates a resultant energy density distribution that may be created by the system of FIG. 27. A relatively high energy density 720 (shown hatched) develops between the trachea 18 and esophagus 30, in the area of the posterior plexus 23, with a slightly lower density 721 developing around the lateral and anterior aspects of the trachea 18 (still sufficient to ablate the anterior plexus), and almost no field develops around the majority of the circumference of the esophagus 30. By circulating cooling media through the balloon of the esophageal device, the tissue of the esophagus may be protected from injury. Further, by circulating cooling fluid through the balloon of the tracheal device, the surface tissue on the inner wall of the trachea may be protected.

Figure 29:
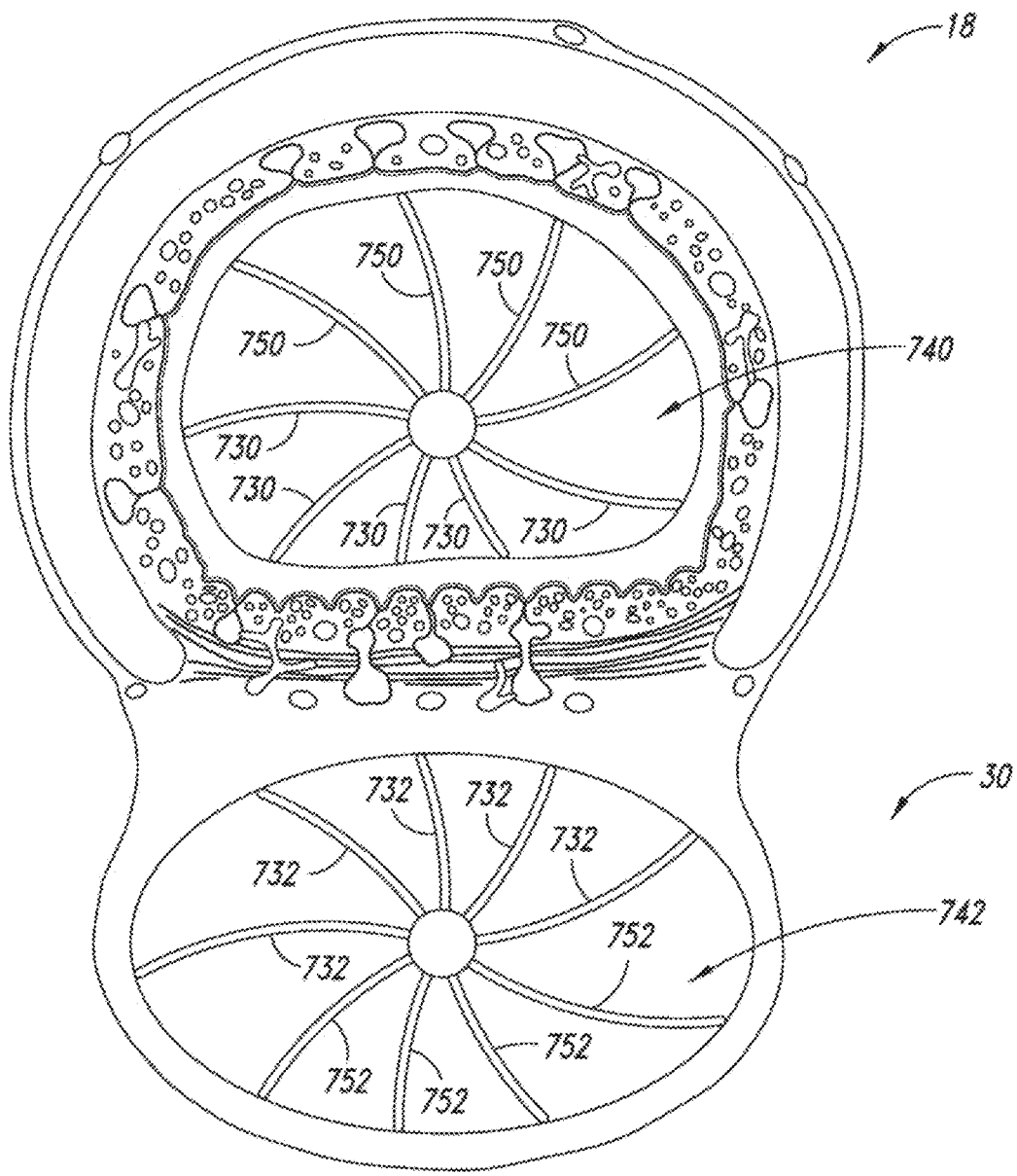
FIG. 29 is a schematic view of an embodiment of the present invention employing trachea-to-esophagus bipolar, posterior isolated electrodes.

A further localization of the energy field may be achieved through alternative embodiments, for example, as shown in FIG. 29. In this embodiment, the active electrodes 730, 732 are confined to the posterior aspect of the tracheal device 740 and the anterior aspect of the esophageal device 742. The opposing arms 750, 752 of the devices 740, 742 can be passive (e.g., ground electrodes). All of the aforementioned alternatives for achieving this electrode localization apply, as well as those describing the potential differential cooling/protection options.

Figure 30:
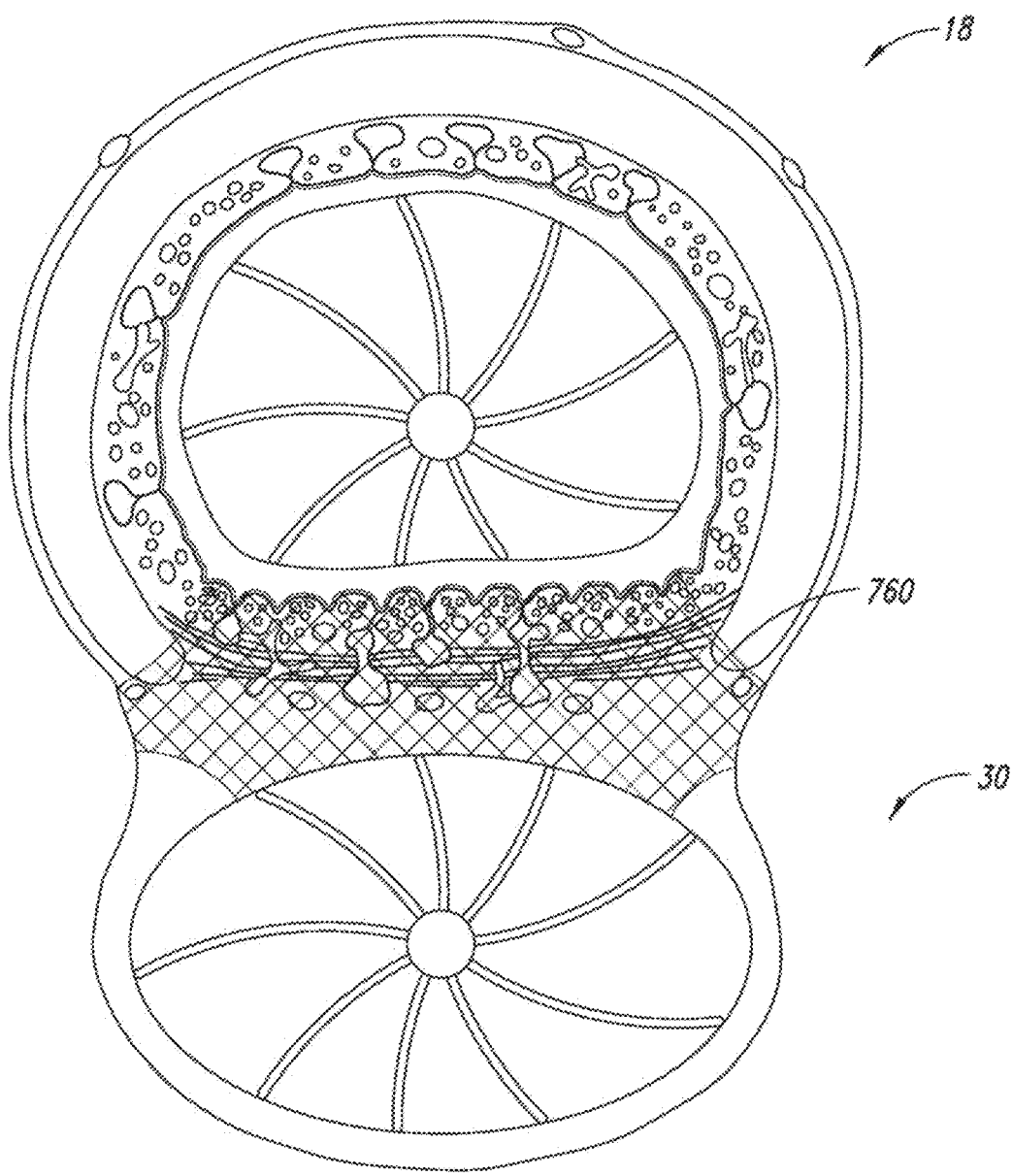
FIG. 30 illustrates a bipolar energy distribution possible with the embodiment of FIG. 29.

FIG. 30 illustrates an energy density localization as may be achieved by the embodiment of FIG. 29. Such embodiments localize the energy density in the region 760 between the trachea 18 and the esophagus 30, and target more specifically the posterior plexus. Again, esophageal cooling may be applied to minimize damage to esophageal tissue.

Figure 31A:
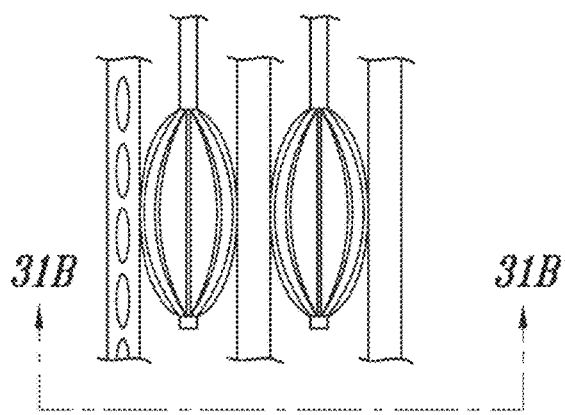
Figure 31B:
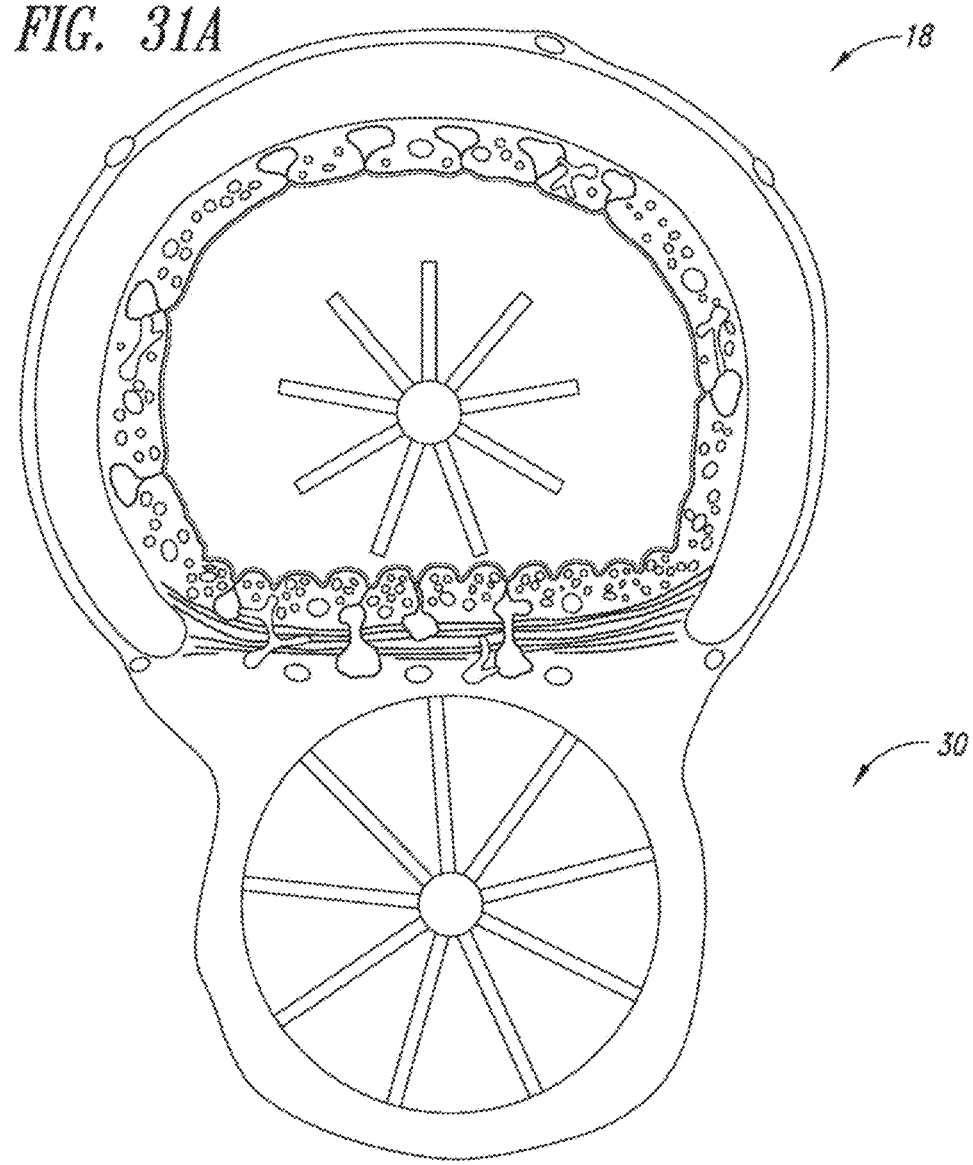

It should also be appreciated that any of the above balloon supported embodiments (FIGS. 25A through 30) can be made with the electrode and support elements only without the use of balloons, and can be made to create the same ablation patterns seen in all of the above balloon supported embodiments. For example, FIGS. 31A and 31B illustrate an alternative embodiment similar to the embodiment described in connection with FIGS. 29 and 30, but in a non-balloon-supported embodiment. An energy density distribution pattern such as shown in FIG. 30 also may be produced by the embodiment of FIGS. 31A and 31B.

Figure 32:
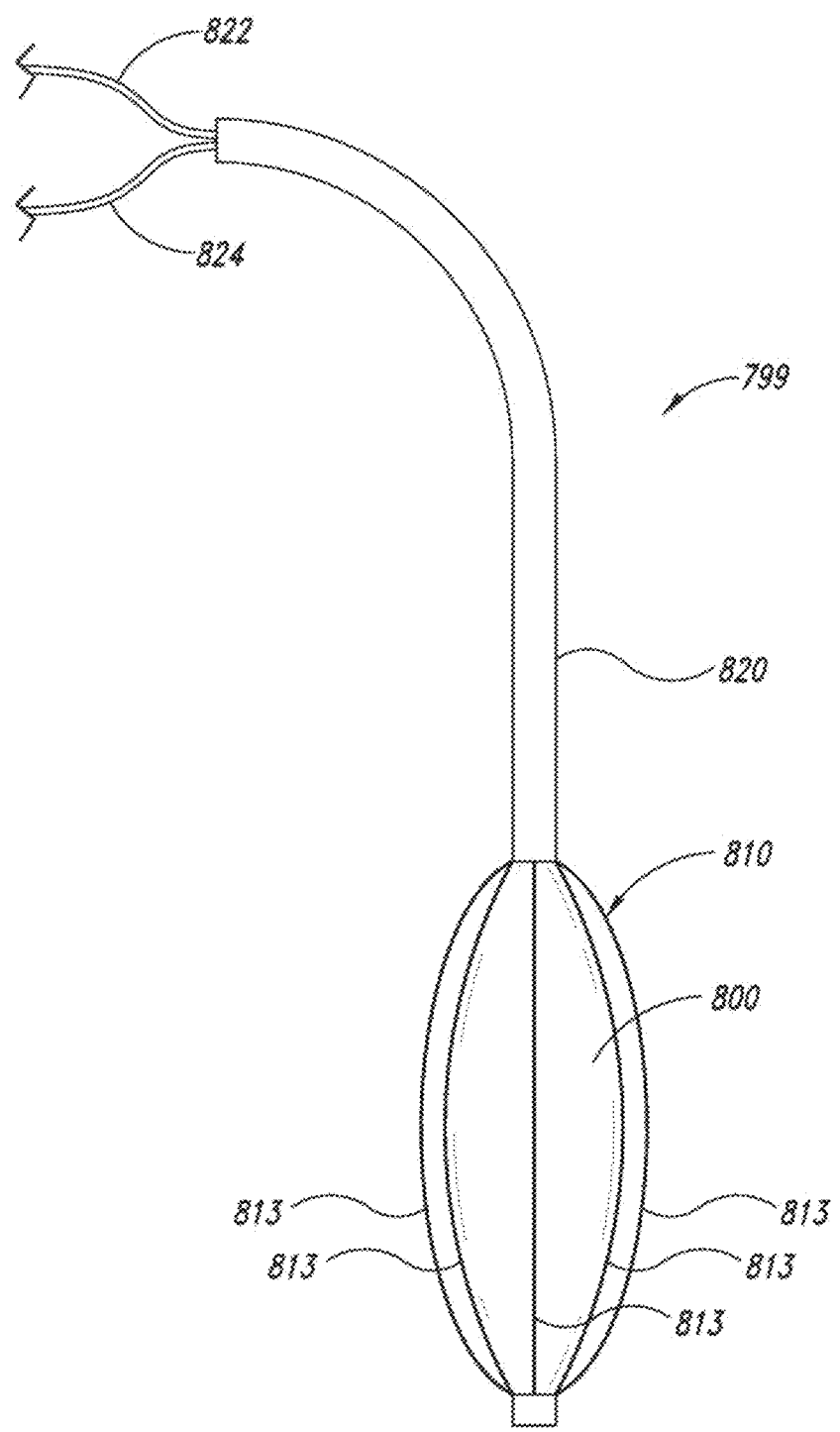
FIG. 32 is an elevational view of an exemplary basket embodiment according to the present invention.

FIG. 32 illustrates an embodiment of the present invention in side elevation that may correspond to the types of device described in the previous embodiments. Note that in FIG. 32, the device 799 includes a balloon 800 shown in conjunction with the basket electrode array 810. In some embodiments, as described, the balloon 800 is eliminated and the basket array 810 is carried directly on a central shaft 820. The basket array 810 includes a plurality of flexible, resilient, elongated electrode struts 813 oriented in a longitudinal direction and arranged around the circumference of shaft 820. Electrode struts 813 bow outwardly into an expanded, arcuate shape either under the expansion force of balloon 800, or by pulling on the distal ends thereof in a proximal direction, whereby electrode struts 813 bow outwardly under compression. The device 799 includes in inflow conduit 822 and an outflow conduit 824 used to circulate media through the balloon 800.

Figures 33A, 33B:
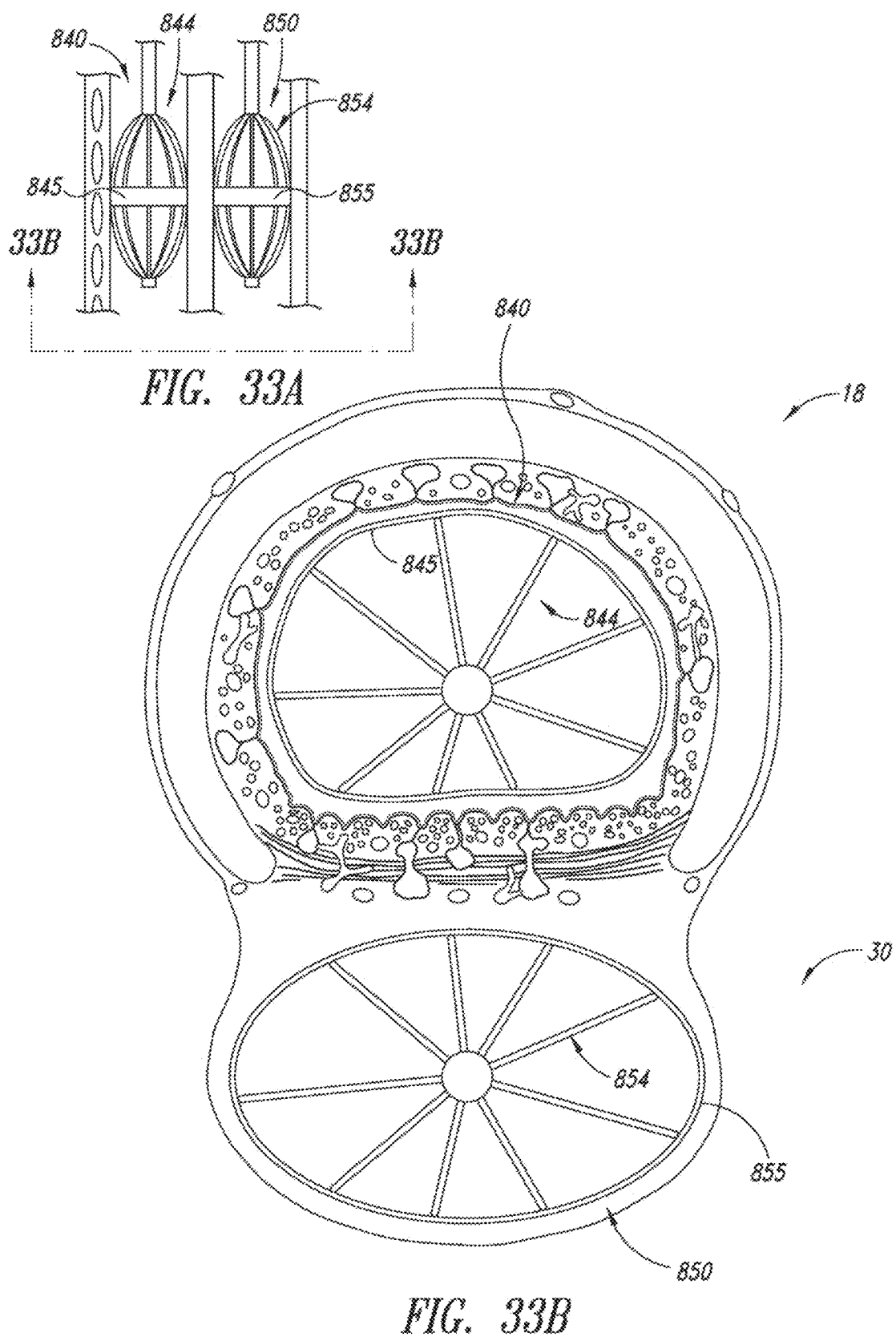
FIGS. 33A and 33B are schematic views of an embodiment employing a bipolar wire cage with circumferential electrode bands.

Other variations of the embodiments described so far are shown in FIGS. 33A and 33B. In FIGS. 33A and 33B, a tracheal device 840 includes a support cage 844 which carries on its periphery a circumferential band 845 that can be selectively insulated and energized to create any of a variety of energy density patterns, including those shown in FIG. 26, 28 or 30. The band 845 can be a conductive flexible member that is in the form of a conductive strip, tubular band, or the like. The band may have one or more discontinuities or a sinusoidal or other shape to allow it to expand circumferentially. The band 845 can be movable from a contracted configuration to an expanded configuration. Spaced apart struts of the support cage 844 extend radially outward to the circumferential band 845. Any number of bands of different sizes and configurations can be carried by the cage 844.

Figures 34A, 34B:
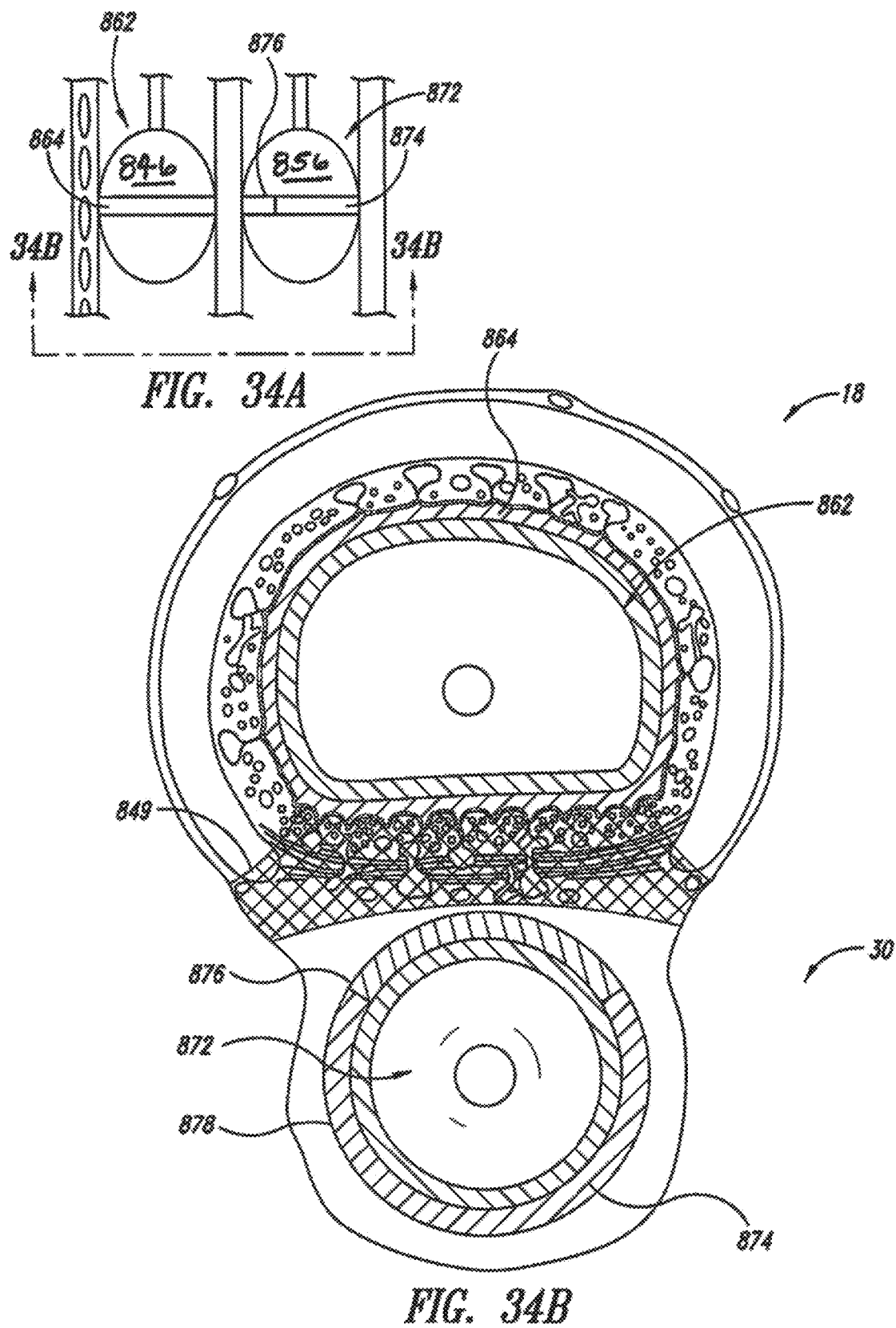
FIGS. 34A and 34B are schematic views of an embodiment of the present invention employing bipolar balloons with circumferential electrode bands.

The esophageal device 850 includes a support cage 854 that may also carry on its periphery a circumferential band 855 that can be selectively insulated and energized to create any of the energy density patterns shown in FIG. 26, 28 or 30 or a variety of other patterns. Similarly, the support structures 844, 854 for the circumferential band of FIGS. 33A and 33B could be replaced by a balloon 846, as shown in FIGS. 34A and 34B. FIG. 34B also show one possible energy density pattern, including high energy density region 849 (shown hatched), achieved by the embodiments in either FIGS. 33A-33B or FIGS. 34A-34B.

A tracheal device 862 of FIGS. 34A and 34B can include a band 864 with an active electrode. In some embodiments, the entire band 864 is an electrode. In other embodiments, one or more portions of the band 864 can be electrodes while other portions are insulated. A device 872 includes a band 874 with an active portion 876 and a passive portion 878. The active portion 876 can be an electrode that cooperates with the band 864 to target the posterior pulmonary plexus or other target region. The bands 864, 874 can be portions of a balloon or other type of inflatable or expandable member. In some embodiments, the walls of the balloons include electrodes mounted or adhered thereto. The balloon (wire basket or cage) can be an actuable device movable between a delivery configuration and a deployed configuration to move the band 874.

Eliminating the balloon in the longitudinal support structure embodiments described above may require different means for providing cooling or protection. Further description of such alternative embodiments are provided later in the present disclosure.

Figure 35:
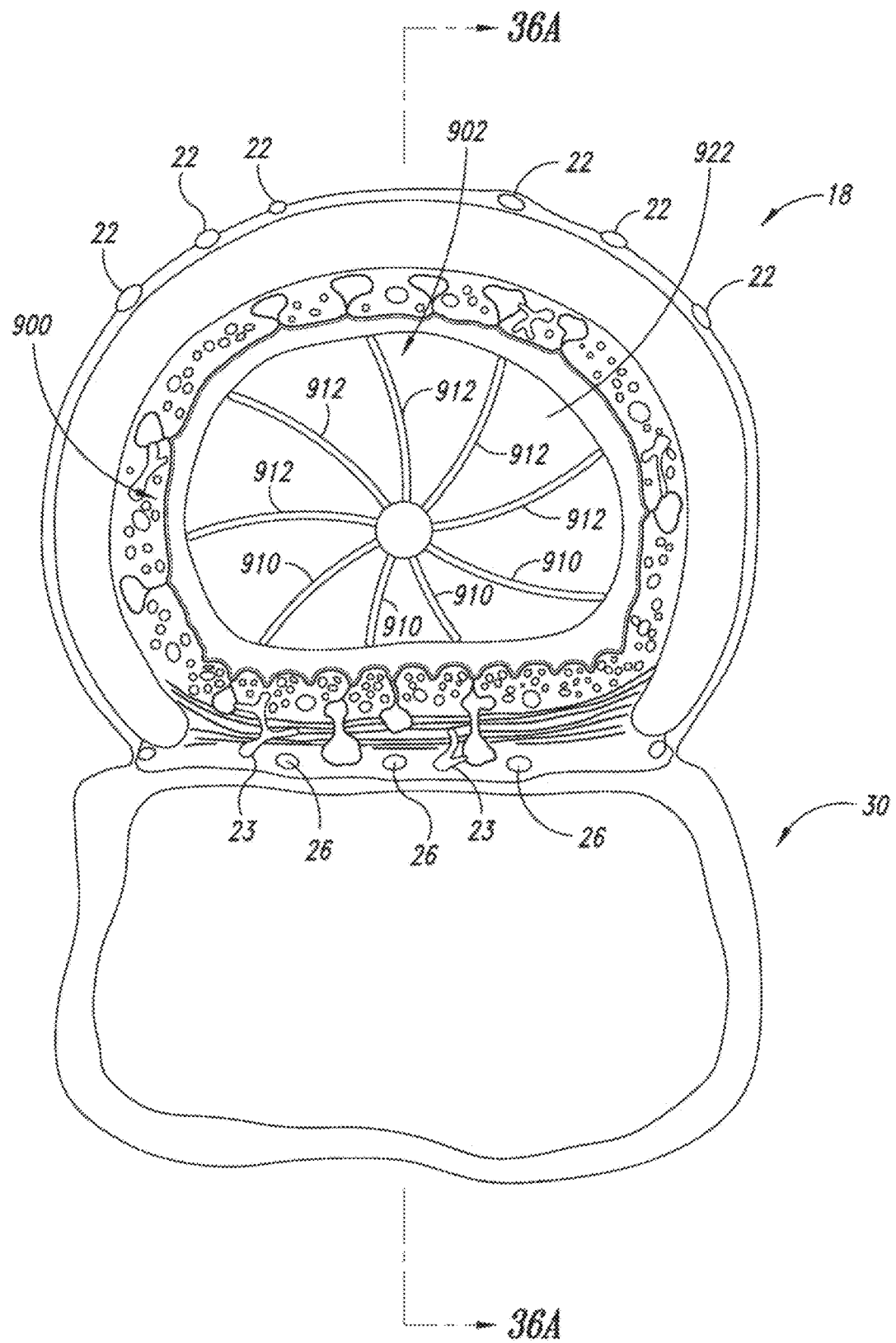
FIG. 35 is a schematic view of an embodiment of the present invention employing tracheal bipolar electrodes with a single tracheal protection zone.

Embodiments described to this point have either shown monopolar devices within the trachea, or bipolar devices which energize from trachea to esophagus, or vice versa. FIG. 35 illustrates a further embodiment whereby bipolar energy can be delivered from within the trachea 18 alone, in order to concentrate the energy density around the circumference of the trachea 18 and target both the anterior plexus 22 and posterior plexus 23, with potentially higher energy density than would be achievable by monopolar energy alone.

In the embodiment of FIG. 35, a device 900 includes an electrode array 902 that is divided into two distinct sections, wherein one section serves as the active electrodes 910 and the other section serves as return electrodes 912 (e.g., ground electrodes). In this way energy may be delivered from active electrodes 910 to return electrodes 912 via the tissue in the tracheal wall to produce the desired energy density pattern. Other aspects of electrode design and material selection previously described apply to this embodiment as well.

Figure 36A:
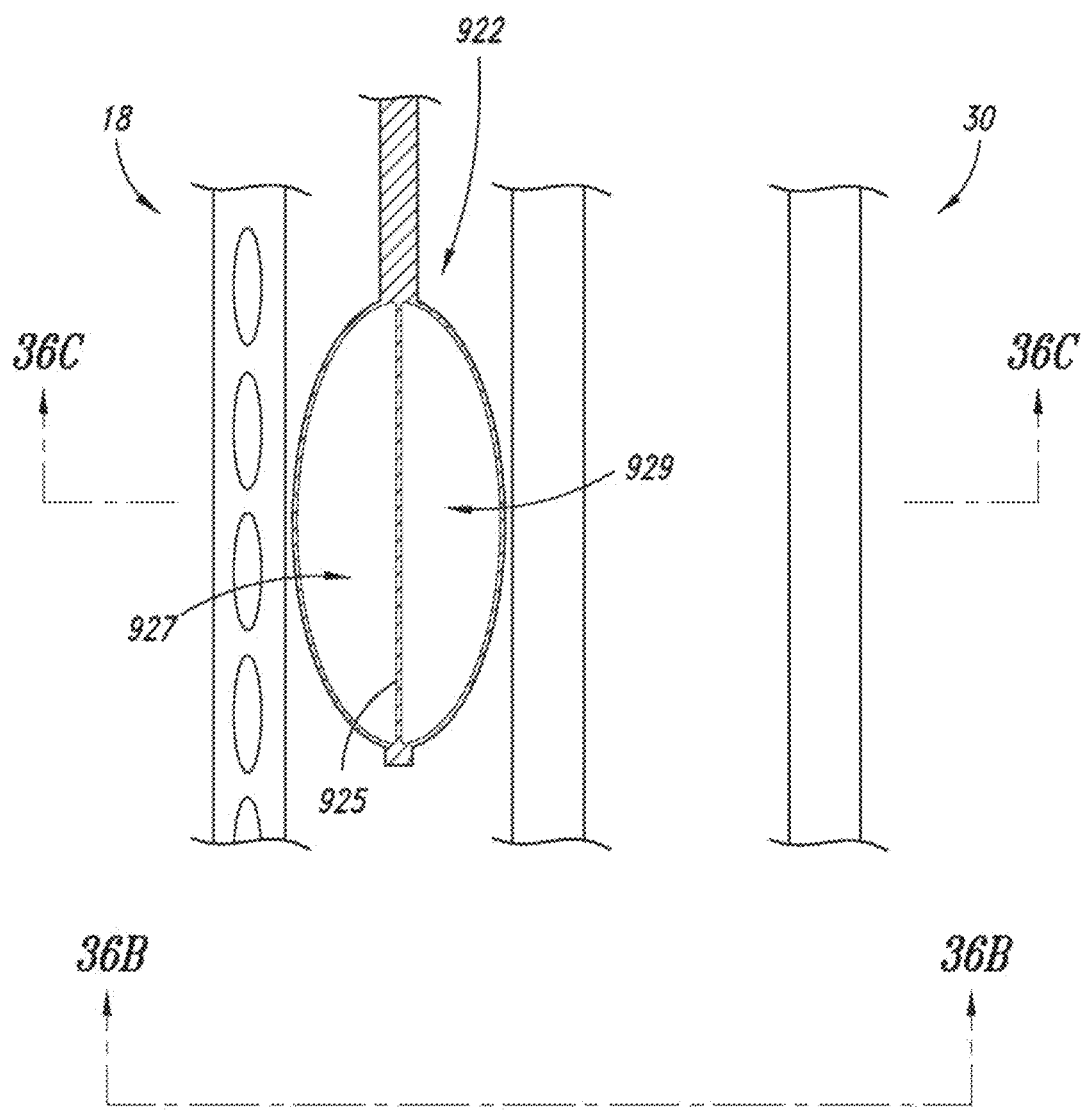
FIG. 36A is a schematic view of an embodiment of the present invention in an airway and employing tracheal bipolar electrodes with a dual tracheal protection zone.
Figure 36B:
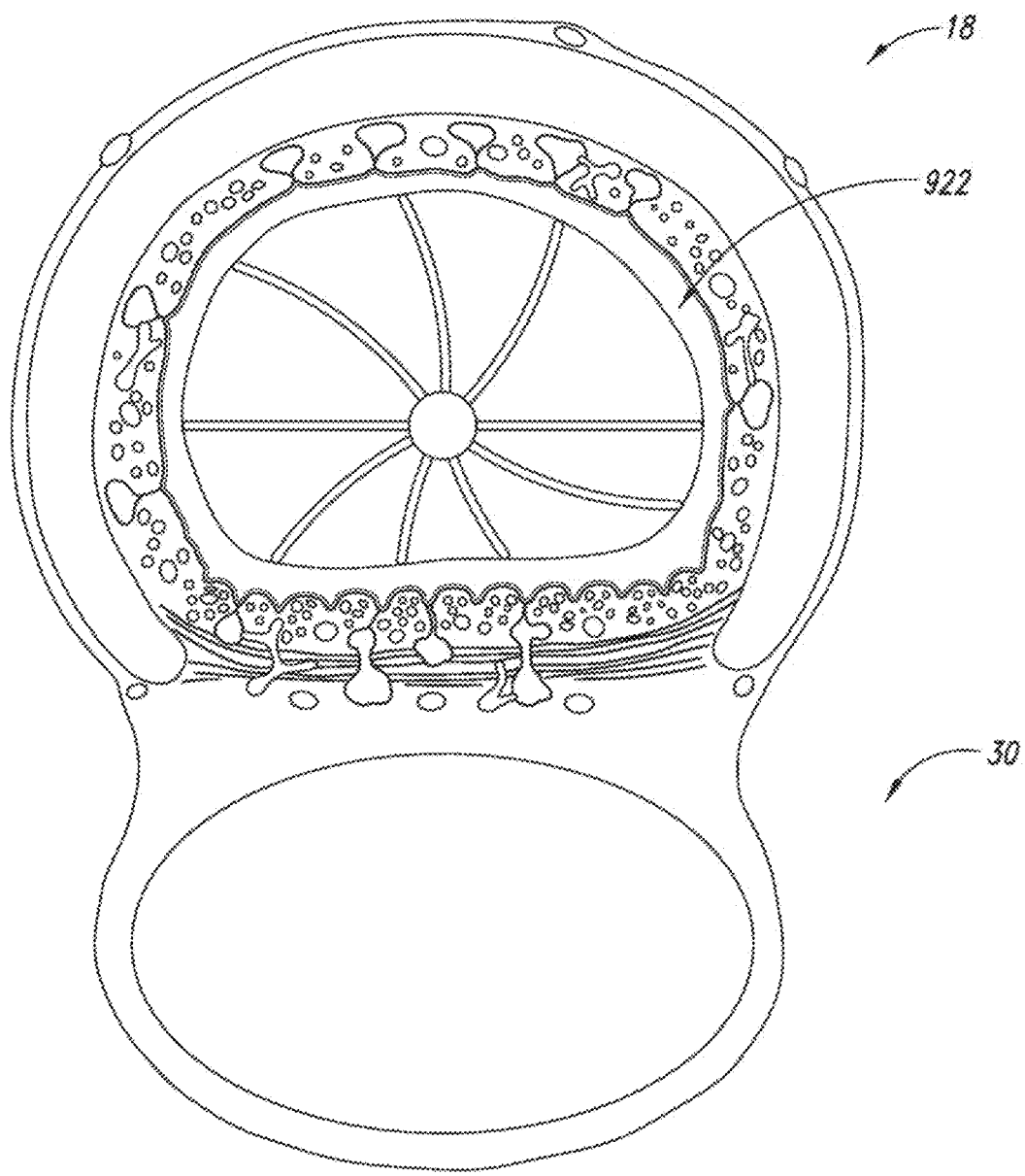
FIG. 36B is a schematic view of the tracheal device of FIG. 36A.
Figure 36C:
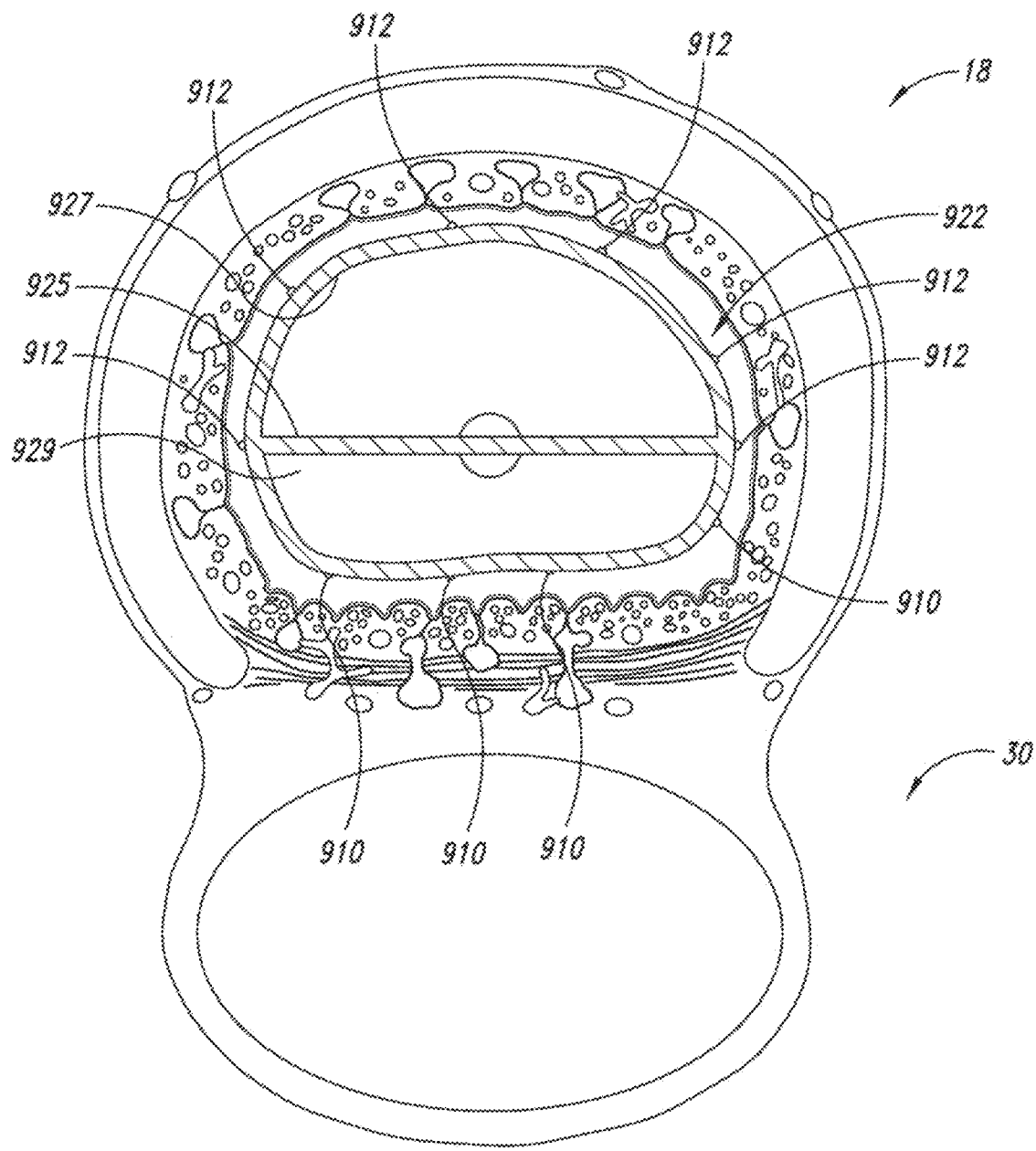
FIG. 36C is a top plan view of the tracheal device of FIG. 36A.

FIGS. 36A-36C show a variation of the bipolar system in FIG. 35. The system includes a basket-type electrode array as described in previous embodiments having a plurality of electrode bands. The electrode array is disposed around a balloon 922. The balloon 922 is divided into different sections by a septum 925 within the balloon 922. The septum 925 divides chambers 927, 929. Fluid at different temperatures can be delivered to the chambers 927, 929 to provide differential cooling between opposing surfaces of the balloon 922. In a further alternative, there would be a dual balloon system having one balloon facing the anterior and one balloon facing the posterior portion of the trachea 18. Different temperatures or different flow rates of media can be introduced into the different cooling/protection zones in order to provide greater protection for one area than the other. This differential in temperature profiles can also be used to direct the area of ablation more deeply into the wall of the trachea 18, directing it more towards the nerves. For example, if the nerves 23 on the posterior side are more deeply embedded in the bridge tissue between the trachea 18 and esophagus 30, more cooling might be desired here than on the anterior side. Another scenario is one in which the user only wants to protect the superficial mucosa on the anterior side, and so a comparatively low level of protection is required. On the posterior side, on the other hand, more protection may be required to preserve the integrity and function of the esophagus 30, and to prevent fistulas from occurring. A wide range of different types of split or multi-chambered inflatable members can be used.

It can also be appreciated that embodiments disclosed herein, such as the embodiment of FIGS. 36A-36C, which occlude the lung during treatment, can be deployed and retracted in order to allow for ventilation. Alternatively (not shown), any of these occlusive devices can be designed with a lumen or lumens which provide flow through the devices, allowing for ventilation of the lung distal to the occlusion site. Room air, oxygen or the like can be supplied to the distal lung.

The following family of designs shares a common attribute in that they take advantage of the cartilaginous rings which surround the upper airways to actually locate the delivery portions between the insulating rings, directing the energy directly into the only weakness in the wall of the airway from which the energy can reach the nerves on the anterior side.

FIGS. 37A-37C illustrate an embodiment with a device 1000 that includes a stack of a plurality of ring electrodes 1002 attached to a central or offset shaft 1010 which lends support and provides electrical connection to the control box of the system. The illustrated ring electrodes 1002 extend circumferentially about the inner wall of the trachea. The shaft 1010 extends vertically from the rings along a lumen of the trachea. The diameter and width of the ring material is chosen such that it fits entirely or substantially within the gap between two adjacent cartilaginous rings.

The diameter of the rings 1002 can be set to slightly oversize or to roughly match the diameter of the airway 1016, as shown in FIG. 37A. The rings 1002 themselves may be resilient and expandable similar to a self-expanding vascular stent such that, regardless of airway diameter, they expand to fill the airway circumference. Various designs and methods to vary the diameter of the rings 1002 can be employed in these designs. For example, one end of a given ring may be fixed to the longitudinal spine of the device, and the other formed to engage another longitudinal element which winds the ring down into a smaller diameter for more distal placement (not shown).

The impedance sensors 1003 (shown in dashed line) of FIG. 37B detect the impedance of the tissue of the airway wall and any external structures that may be in contact with the airway wall, such as the pulmonary artery or esophagus. Each of the various tissues and fluids in and surrounding the airway, such as smooth muscle, cartilage, nerves, blood vessels, mucous, air, and blood, has a different impedance. Moreover, previously treated (ablated) tissue will have different impedance than untreated tissue. Thus, the longitudinal and rotational position of the sensor (and hence the electrode) may be detected by measuring the impedance at the location and comparing it to a reference value or to the impedance of tissue at other locations. In this way, the power level or degree of cooling or both may selected based upon the location of the electrode to ensure target nerve structures are ablated without damaging other critical structures such as the esophagus. In addition, the presence of previously created lesions may be detected so that overlapping such lesions and over-treating tissue can be avoided.

Impedance sensors 1003 may be adapted to be manually activated by the user at any particular electrode location. Alternatively, the system may be configured to run the sensors continuously or automatically trigger them prior to or simultaneous with energy delivery through the electrode at each treatment location. Prior to energy delivery, the system may provide an indication of the impedance to the user so that power or coolant delivery may be adjusted, or the system may automatically adjust the power delivered through the electrode based on the measured impedance.

Impedance may also be detected using the electrodes themselves without a separate sensor. The RF generator may be equipped with an impedance detection system which calculates the impedance seen by the electrode when power is delivered. In this way prior to lesion creation at any particular location a very low power signal may be delivered from the electrode and impedance then calculated to ensure proper positioning and power settings.

In use, the rings 1002 are deployed within the desired treatment area. They can be delivered within a sheath or tubular cannula in a compressed state and released when in position to expand into contact with the airway wall. Once deployed, the system is withdrawn proximally, or pushed distally by a small amount. Tactile feedback lets the physician know when the rings have slipped into place. In some embodiments, an active electrode is configured to fit between a first pair of adjacent cartilage rings of the airway in the expanded configuration. Return electrodes are configured to fit between a second pair of adjacent cartilage rings of the airway while the active electrode is positioned between the first pair of adjacent cartilage rings. Alternatively, tissue impedance can be measured, with lower impedance signaling the electrodes are between rings, and in position to access the nerves.

As an alternative to the stacked ring design, a coil could be formed to provide the same inter-cartilaginous locking functionality as the stacked ring design. FIG. 38A shows a device 1040 that includes a coiled or corkscrew-shaped ring 1044. The pitch of the coils 1044 is set such that adjacent turns of the coil lock into separate neighboring inter-cartilaginous regions. In one version of the coiled ring design, a length of resilient coil is provided straightened out inside of a delivery catheter or capture sheath. When the distal tip of the capture sheath is in place at the distal end of the treatment region, a distal tip 1045 and the coils 1044 are delivered to the distal end of the treatment region. The capture sheath is withdrawn until the entire treatment area of interest is covered by the coiled elements. Again, tactile feedback confirms that the rings are locked into place, or impedance is measured. A shaft 1046 extends from the coiled ring 1044 along the lumen of the trachea.

FIGS. 39A and 39B show another embodiment of the coiled ring system 1060 wherein the distal and proximal ends of the coils are both attached to longitudinal members. Coil diameter can be varied by twisting the two elements relative to one another in order to tighten or loosen the diameter of the coils. The coils can seat between the cartilage rings. The system 1060 includes a winding arm 1061 and a proximal electrode 1063.

The locking ring electrode concept can be incorporated into a number of the previously described tracheal-esophageal embodiments in order to recreate the energy density distributions shown in FIGS. 26, 28, and 30. A ring-type device in the lung could be used in combination with any of the previously described esophageal devices to provide esophageal cooling, or to provide esophageal electrodes for a bipolar delivery system.

Figure 40A:
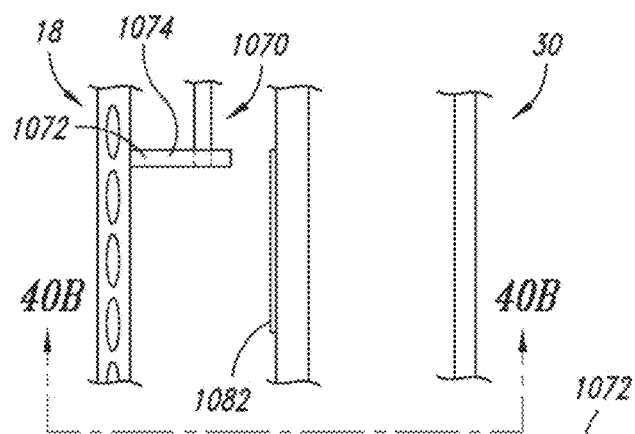
FIGS. 40A and 40B are schematic views of an embodiment of the present invention employing inter-cartilage electrodes with adjustable D-shaped rings in a bipolar configuration.
Figure 40B:
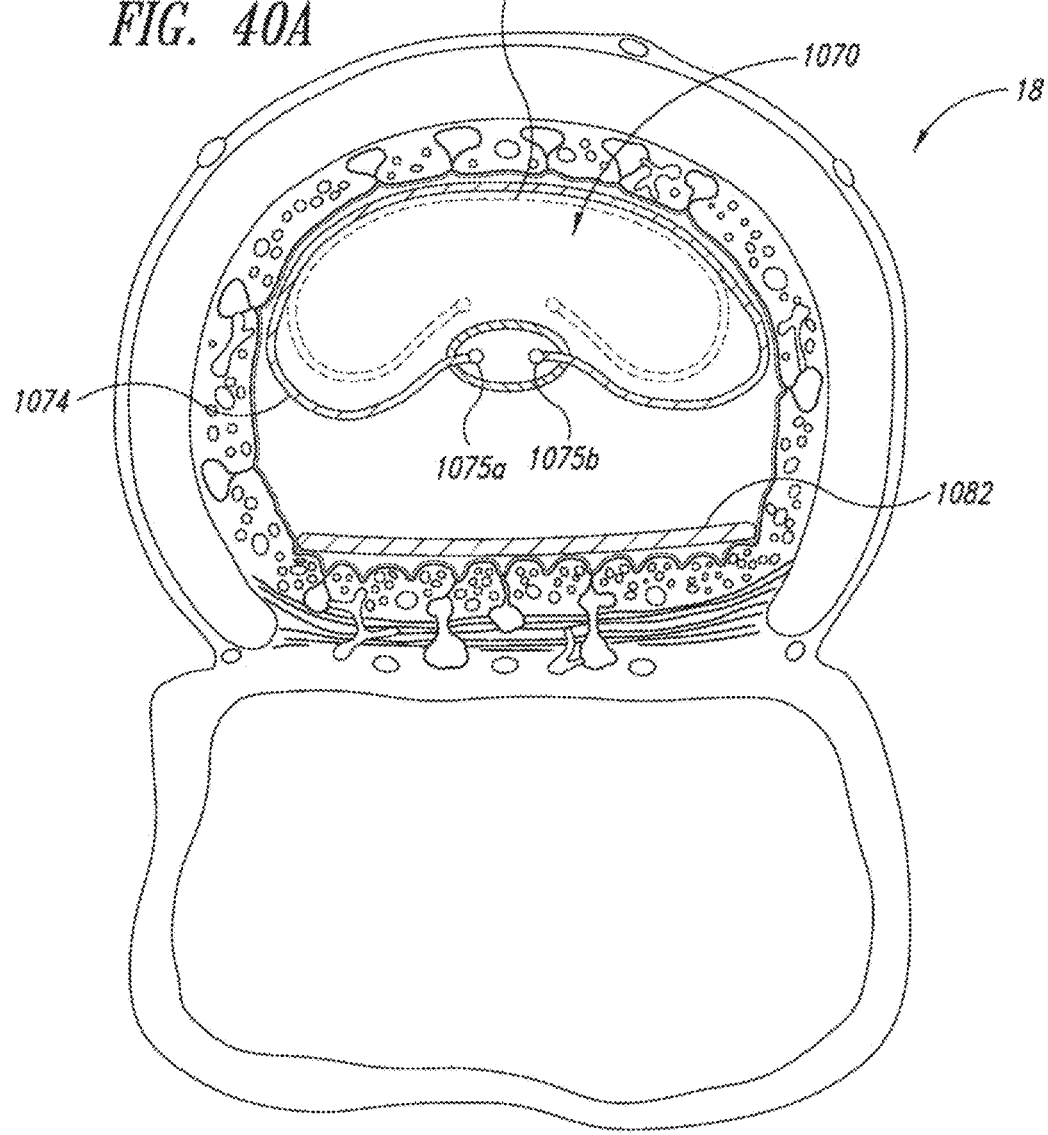

Another variation of the locking ring embodiment is shown in FIGS. 40A and 40B. In this case, a device 1070 includes an anterior portion 1072 defined by a resilient member 1074 formed into a roughly "D" or kidney-shaped or rabbit ear-shaped member or ring. The ends of member 1074 may be wrapped around two independently rotatable longitudinal members 1075*a*, 1075*b*, so that the size and shape of the "D" can be modified by rotating the longitudinal members 1075*a*, 1075*b* to wrap or unwrap the resilient member. For example, rotating the left longitudinal member 1075*a* counter-clockwise and the right one 1075*b* clockwise in FIG. 40B would result in the D ring reducing in size (as shown by the dashed lines).

A plurality of these D-rings can be attached above or below one another in a configuration similar to the one shown in FIG. 37A, and if desired can all be made expandable and contractible as described above. If a bipolar energy pattern is desired, a second set of b-rings can be positioned to contact the posterior wall of the trachea as well (not shown). The anterior and posterior rings can be alternated, or interleaved, such that each subsequent ring faces the opposite direction, or a series of rings can face one direction, and then a separate series of rings faces the opposite direction. The latter configuration provides longitudinal separation of the active and return electrode as well as the anterior/posterior separation provided by the interleaved design.

Alternatively, as shown in FIGS. 40A and 40B, a non-ring electrode 1082 can be used along the posterior aspect of the trachea 18. Since there are no cartilaginous rings on the posterior aspect, an electrode 1082 can be in the form of a mesh electrode, arrays of longitudinal spine electrodes, or any other suitable electrode design can be used in conjunction with the ring or D-ring electrodes described above to allow bipolar energy delivery.

Figure 41A:
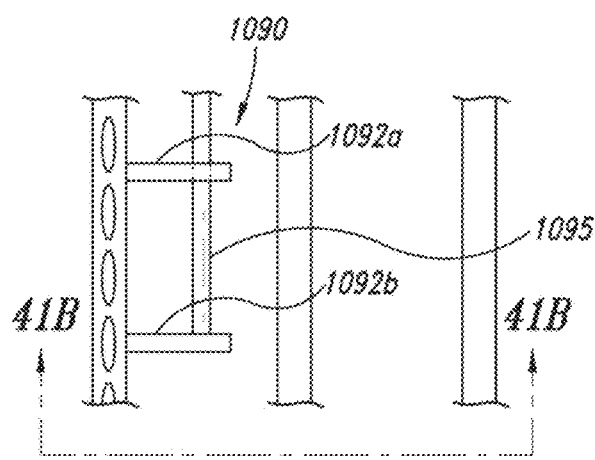
FIGS. 41A and 41B are schematic views of an embodiment of the present invention employing inter-cartilage electrodes with adjustable D-shaped rings in a bipolar configuration with cooling means.
Figure 41B:
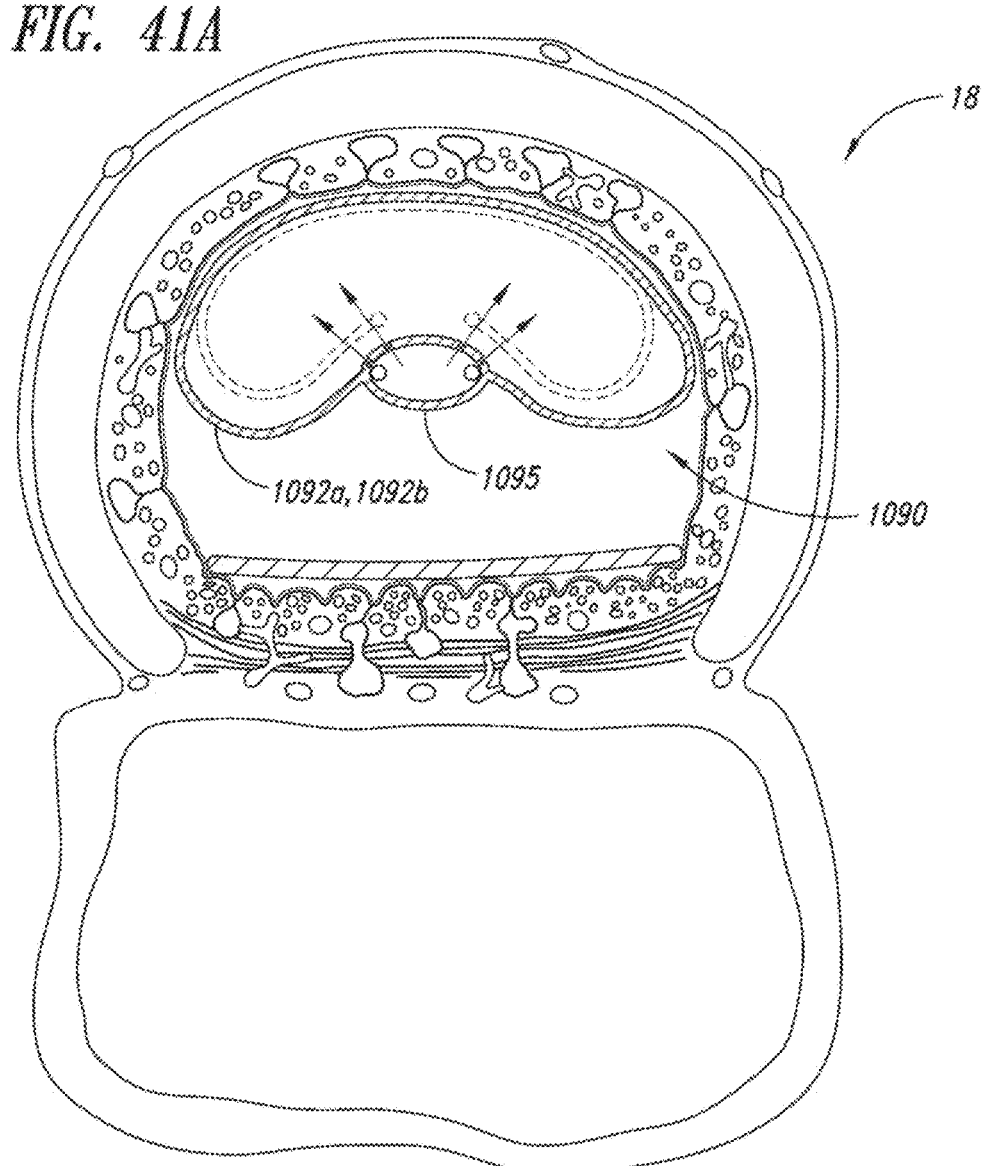

FIGS. 41A and 41B illustrate a further alternative device 1090 that includes holes or vents for introduction of cooling media, and a plurality of spaced apart ring electrodes 1092*a*, 1092*b*. Cooling vents may be disposed in the shaft 1095 to which the electrodes 1092*a*, 1092*b* are attached. Through these vents cooling or protectant media (represented by arrows) can be directly applied to the electrodes and/or to the tissue adjacent to the electrodes. The media can be any of the aforementioned media. Alternatively, any of the vented designs described in this disclosure can use a liquefied gas wherein the gas flows into the system liquefied and cools via an endothermic phase transition.

Figure 42:
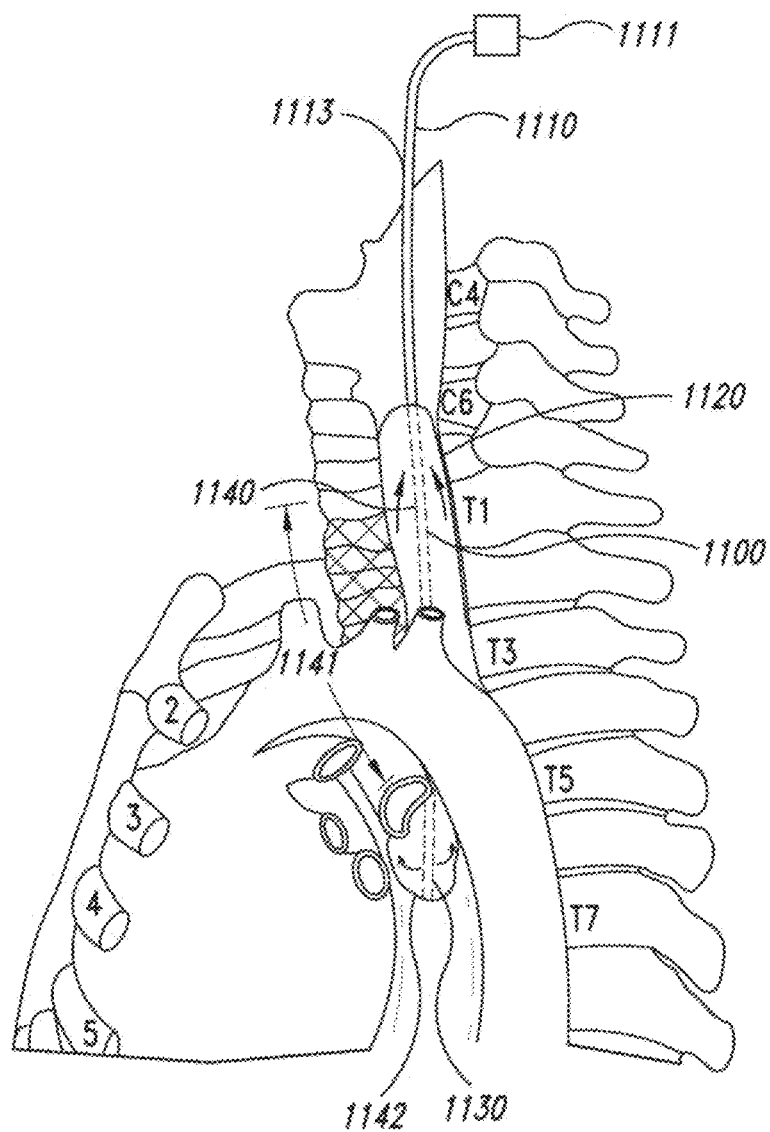
FIG. 42 is a schematic view of an embodiment of the present invention employing an esophageal protection device.

In another exemplary embodiment, shown in FIG. 42, the esophagus is protected by an esophageal device 1100 in the situation where the tracheal device (not shown) alone is involved in the modification or ablation of the nerves. The tracheal device can be monopolar RF, bipolar RF with both leads in the trachea, or microwave.

The embodiment of FIG. 42 is shown to cover a substantial portion of the entire zone of the esophagus 1141 which could potentially suffer tissue damage from a delivery device positioned within the trachea. This affords protection of the entire exposed esophageal territory with a single device placement. Alternatively, the esophageal device could be made shorter, and moved either in concert with, or at appropriate intervals to the movement of the tracheal device. Such an embodiment may include features such as an elongate shaft to insert the balloon and circulate cooling fluid through a balloon 1142, multiple lumens to effectively circulate protectant, and/or an optional guide wire lumen to aid in placement of the device.

Although there is an area of the trachea shown in crosshatch FIG. 42 as the treatment area of the trachea, it should be noted in this and all figures that show exemplary treatment areas that this area is not the only potential treatment area. It is shown merely to point out that in some embodiments the esophageal device covers substantially the entire potential intended treatment zone.

A catheter shaft 1113 of FIG. 42 is connected to a generator/pump unit and can be a multi-lumen shaft to allow bidirectional fluid flow. In certain embodiments, the catheter shaft 1113 has two lumens coupled to side holes. Fluid can be delivered into a proximal balloon end 1142 through one lumen. Media can be circulated within the balloon 1142 to cool the tissue surrounding the esophagus. The media can flow out of the balloon 1142 using the other lumen.

The catheter shaft 1113 can have a sealed tip 1130. A fluid can be delivered through the chamber of the balloon 1142 and returned via the body 1110. One or more conductive elements 1140 can be positioned to be adjacent to or to contact the potential ablative zone. During ablation, the conductive element can help conduct heat between the tissue and the cooling media circulating within the expandable balloon 1142 covering the potential ablative zone 1141.

Figure 43:
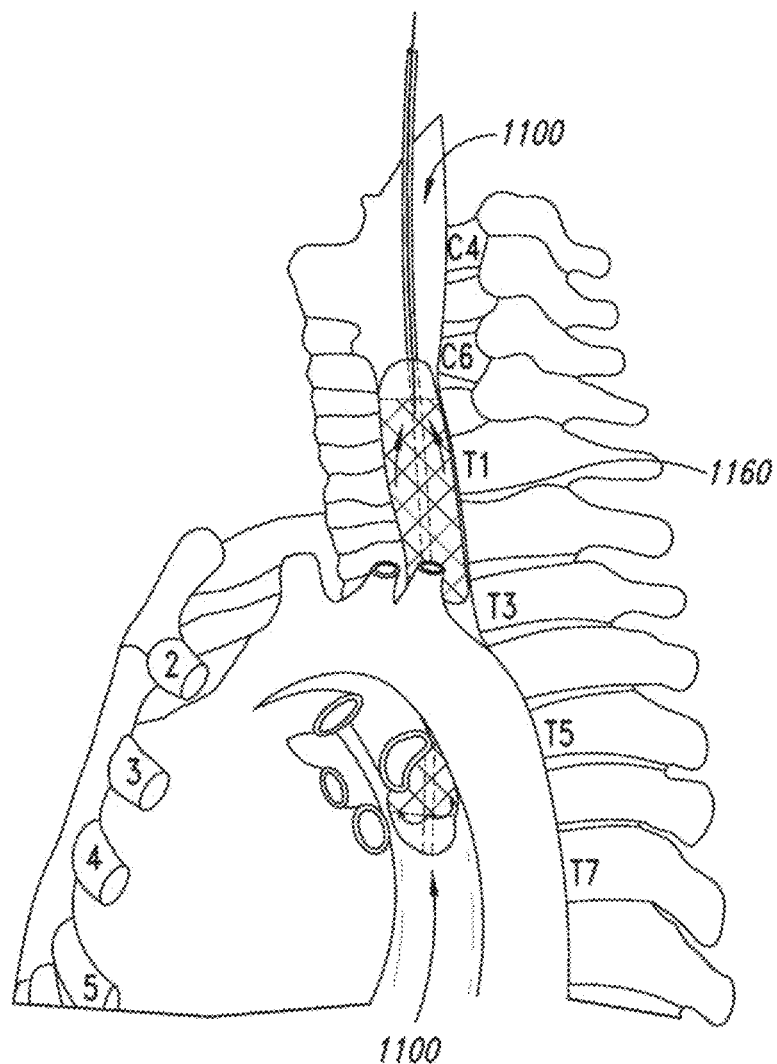
FIG. 43 is a schematic view of an embodiment of the present invention employing esophageal protection with conductive elements.

The exemplary embodiment illustrated in FIG. 43 is a variation of the embodiment of FIG. 42, in which conductive means are added to the basic protection system to allow for bipolar trachea-to-esophagus treatment options. All of the previously mentioned features and benefits apply the embodiment of FIG. 43 as well. While FIG. 43 shows a circumferential conductive zone, such as a wire mesh 1160 on the device, it should be appreciated that any of the conductive elements described herein (wire cages, ring electrodes, etc.) could be configured onto the protective device 1100. In the case where the protective device is long enough to cover substantially all of the potential treatment area, the conductive elements of the protective device will also cover substantially the entire potential treatment zone.

Figure 44:
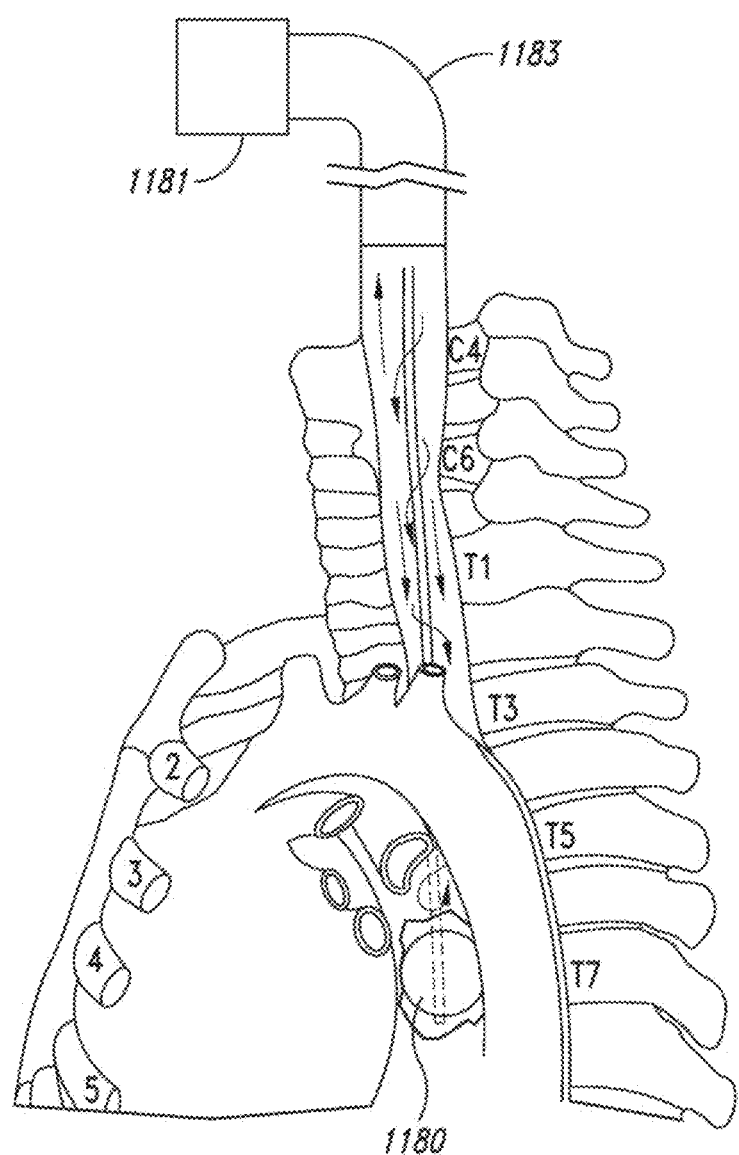
FIG. 44 is a schematic view of an embodiment of the present invention employing a distal occlusion device with a gas protectant.

FIG. 44 illustrates another alternative embodiment including means for protecting the esophagus during nerve modification. In this case, a relatively short occlusion device 1180 is delivered to the esophagus distal to the most likely termination of the potential treatment zone. Behind this occlusion device 1180, protectant media is circulated freely in the esophagus. In this embodiment, cooled gasses are most likely to be used. Room air, nitrogen, oxygen, etc., may be used. Forced media (e.g., forced cool air) can be circulated above the occlusion device 1180 illustrated as a balloon. A wide range of different types of sources 1181 with one or more pumps (e.g., piston pumps, positive displacement pumps, roller pumps, etc.) or blowers can pass media through a conduit 1183. The illustrated conduit 1183 is positioned in the lumen of the esophagus 30 to circulate the media in the lumen of the esophagus 30. The media can flow at a relatively high flow rate to protect the trachea and/or esophagus. The occlusion device 1180 prevents media from distending the stomach and/or the gastrointestinal tract.

As shown in the exemplary embodiment of FIG. 44, the occlusion device 1180 is a balloon, but other devices which provide substantial blockage to the passage of gas can be used. Additionally, FIG. 44 shows the protectant being introduced via the nose or the mouth directly. Custom nose plugs or facemasks can be designed to effect this delivery. For example, a pump or blower can deliver chilled media to the airway or esophagus of the patient via a facemask. Alternatively (not shown), side holes in the shaft of the occlusion device can be used for introduction of protectant. In this case, liquefied gas that is allowed to warm in the catheter shaft and exit the catheter as a gas can be used. The degree of protection, as with all of the protective devices, can be varied through temperature of the protective media, or through the flow rate of the protective media.

Figure 45:
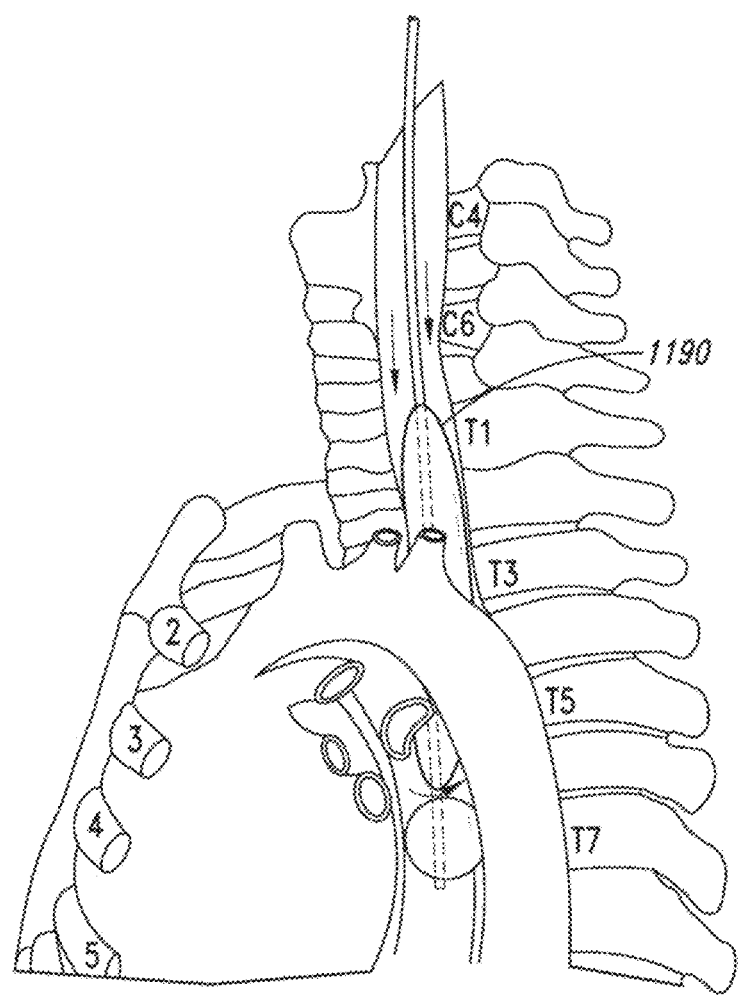
FIG. 45 is a schematic view of an embodiment of the present invention employing a distal occlusion device with a gas protectant and conductive elements.
Figure 46:
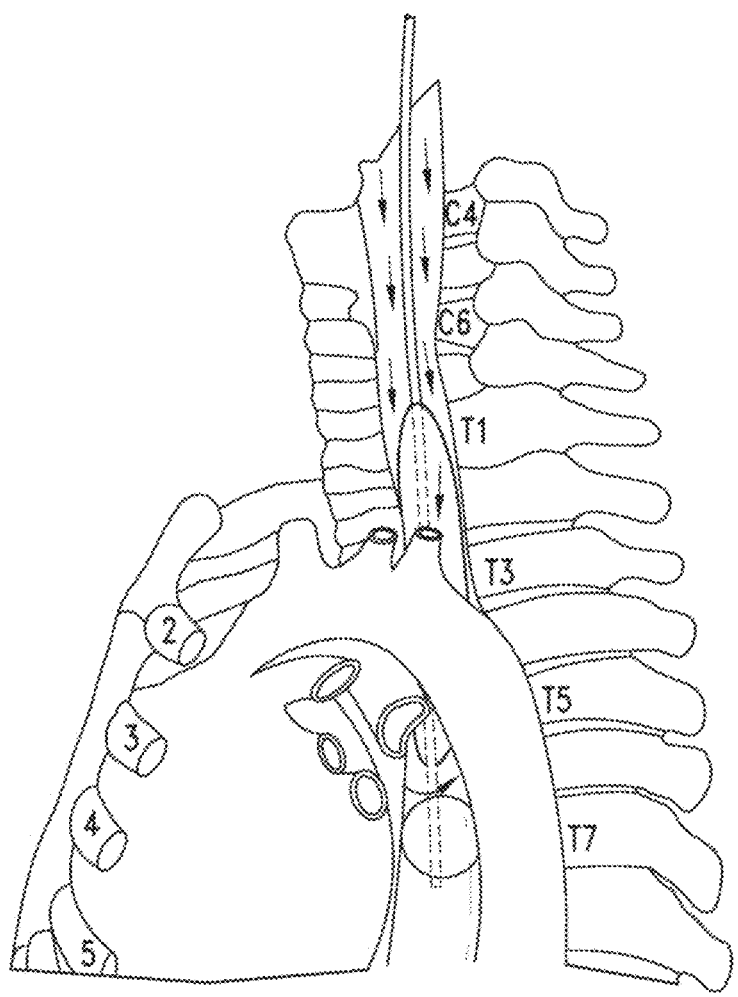
FIG. 46 is a schematic view of an embodiment of the present invention employing a distal occlusion device with a gas protectant and conductive elements showing the protective gas flow.

FIGS. 45 and 46 show further alternative embodiments of a distal occlusion protective device wherein a conductive element is incorporated into the system. This enables bipolar trachea-to-esophagus treatment. The conductive element may be attached to the same shaft as the occlusion device, such that the entire system is introduced at once. Alternatively, the conductive elements could be a separate device which is placed alongside of or over top of the occlusion device, and which is insertable and operable separately from the occlusion device. The conductive element may be constructed similarly to any of the esophageal devices described herein, such as a basket electrode array 1190 having a plurality of electrode bands.

FIG. 46 shows the embodiment of FIG. 45 with protectant circulating around and through the elements of the conductive system. As with prior embodiments, the protectant can be introduced through the nose or mouth, through the central shafts of the devices, or through the conductive elements themselves. Introduction through the conductive elements themselves provides the added bonus of cooling those elements and preventing tissue charring during thermal ablation. Charring on the electrodes greatly increases the impedance of the system and decreases or eliminates the effectiveness of the ablation.

Microwave energy has found increasing uses over the past few years and may be used in embodiments of the present invention as an alternative energy system. Principally, microwave energy is delivered through an antenna. There are a number of different types of microwave antennae. With suitable modifications based on the teachings of the instant disclosure, some the basic microwave antenna forms may be incorporated into devices designed for modulating or modifying pulmonary nerves as described herein. Of particular use for the application of catheter based microwave energy within the trachea-to-esophagus region is the family of antenna based upon coaxial wire leads. There are a number of different designs using the coaxial leads. These types of antennae come in many different configurations—monopole, dipole, slot, capped, choked, cap-choke, sleeved, etc. Each antenna variation is intended to either shift the field orientation, to improve the efficiency of energy delivery, or both. Wave guide antennae are another known antennae for microwave applications. Wave guide antennae are typically a metal jacketed dielectric, which is fed with a coaxial cable inserted into a side hole in the device.

Examples of basic configurations for microwave antennae that may be modified and configured for use with embodiments of the present invention by persons of ordinary skill in the art may be found in the following publications: Microwave Catheter Design; Robert D. Nevels, G. Dickey Arndt, George W. Raffoul, James R. Carl, and Antonio Pacifico. *IEEE TRANSACTIONS ON BIOMEDICAL ENGINEERING*, VOL. 45, NO. 7, July 1998, and A Review of Coaxial-Based Interstitial Antennas for Hepatic Microwave Ablation, John M. Bertram, Deshan Yang, Mark C. Converse, John G. Webster, & David M. Mahvi; *Critical Reviews™ in Biomedical Engineering,* 34(3):187-213 (2006). Both of these publications are incorporated by reference in their entirety. Among the reasons that such antennae designs cannot be directly incorporated into embodiments of the present invention is their unsuitability for pulmonary devices without modification. Among the parameters that must be reconfigured for deployment in the pulmonary tree according to embodiments of the present invention are the size, stiffness and general deliverability.

In pulmonary applications, the devices need to be introduced through or in conjunction with bronchoscopes, and manipulated down tortuous paths into the area of the lung to be treated. This necessitates the translation of conventional microwave antenna designs into application specific embodiments, such as the exemplary embodiments shown in FIGS. 51A-54C. One generally common aspect for these pulmonary devices is flexibility, although in some cases a flexible body member is coupled to more rigid segments in the area of the slots, caps, and chokes. Other aspects that must be specially considered for pulmonary applications are features to provide tissue coupling, maintain positioning relative to the target tissue, cool non-target tissue, etc.

Figure 47:
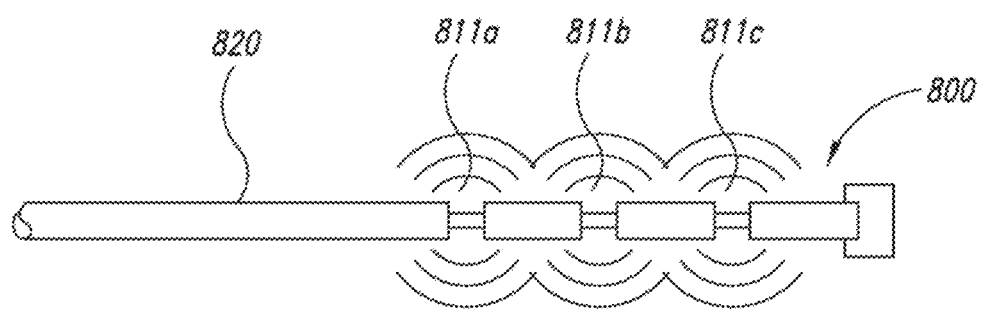
FIG. 47 is a schematic view of an embodiment of the present invention employing a multi-slot coaxial microwave antenna.

In one exemplary embodiment, an antenna that may be particularly effective in pulmonary applications for microwave energy delivery is a multi-slot coaxial design such as shown FIG. 47. In this embodiment, in addition to a slot near the tip, a plurality of additional slots are positioned at appropriate distances down the shaft of the device, with the distances being determined by wavelengths of operation, desired specific absorption rate (SAR) pattern, etc. Specific absorption rate, or SAR, is a proxy for energy delivery to the tissue, or heating profiles of the tissue, and are the standard way in which antenna designs are evaluated and optimized.

In many microwave antenna applications in medicine, the desire is to provide the largest effective area of energy delivery to tissue, with the area of treatment extending from the edge of the antenna or applicator to the periphery of the largest area possible. However, in the case of pulmonary nerve modulation, protection of the structures immediately adjacent the applicator is preferred. Ideally, the energy would pass through a cooling or protective layer, heat tissue within a few millimeters of a zone, and then drop off in intensity in order not to harm critical non-target tissues such as the esophagus and alveoli. This is not possible in any of the antenna designs shown from the prior art. Embodiments to achieve these ends are shown and described in detail below in FIGS. 58A-53.

In microwave terms, the more "lossy" a material is, the higher the propensity of that material to heat up. Lossy materials in the body are typically those with higher water content. This is due to the fact that microwaves heat dipole molecules by causing rotation of the dipole molecule under the oscillations of the wave. Water is a strong dipole molecule, and heats extremely well under microwaves.

The tables below show various electrical properties of different tissues at two different commonly used medical microwave frequencies, 915 MHz and 2.45 GHz. One aspect that is apparent from these data is that as microwave frequency increases, depth of penetration decreases—so lesions are made more shallowly. For this reason, it is likely that the preferred frequency for pulmonary nerve modulation will be 2.45 GHz or higher. At least one microwave system designed by Microsulis Inc. operates at frequencies in the 9 GHz region. The frequency can be selected so that the microwave energy penetrates the tissue to a depth of the target tissue with an intensity sufficient to alter the target tissue while having insufficient intensity in non-target tissue, such as non-target tissue beyond the nerve tissue.

Frequency alone does not determine depth and character of penetration and tissue modification. It is known that standing waves can develop in microwave fields, and specific systems must be modeled with FEA systems to determine the most likely resultant SAR patterns within a given tissue system.

For example, the permittivities of most of the tissue types listed below are roughly in a similar range, indicating that they will heat similarly. However, there are a couple of exceptions—the esophagus may heat more easily than other tissues, and so may require the protection that has been discussed throughout this disclosure. Also, it is of particular interest that the permittivity of the lung differs significantly as between the inflated and deflated states.

| Tissue Name | Frequency [Hz] | Conductivity [S/m] | Relative permittivity | Loss tangent | Wavelength [m] | Penetration depth [m] |
| --- | --- | --- | --- | --- | --- | --- |
| Cartilage | 15000000 | 0.7892 | 42.6 | 0.36394 | 0.049412 | 0.044603 |
| Cartilage | 2450000000 | 1.7559 | 38.77 | 0.33228 | 0.019393 | 0.019077 |

| Tissue name | Frequency [Hz] | Conductivity [S/m] | Relative permittivity | Loss tangent | Wavelength [m] | Penetration depth [m] |
| --- | --- | --- | --- | --- | --- | --- |
| LungInflated | 915000000 | 0.45926 | 21.972 | 0.41063 | 0.068523 | 0.05527 |
| LungInflated | 2450000000 | 0.80416 | 20.477 | 0.28813 | 0.02677 | 0.030175 |

| Tissue name | Frequency [Hz] | Conductivity [S/m] | Relative permittivity | Loss tangent | Wavelength [m] | Penetration depth [m] |
| --- | --- | --- | --- | --- | --- | --- |
| Mucous Membrane | 915000000 | 0.85015 | 46.021 | 0.36291 | 0.047545 | 0.043032 |
| Mucous Membrane | 2450000000 | 1.5919 | 42.853 | 0.27255 | 0.018524 | 0.022029 |

| Tissue name | Frequency [Hz] | Conductivity [S/m] | Relative permittivity | Loss tangent | Wavelength [m] | Penetration depth [m] |
|---|---|---|---|---|---|---|
| Nerve | 915000000 | 0.57759 | 32.486 | 0.34929 | 0.056652 | 0.053157 |
| Nerve | 2450000000 | 1.0886 | 30.145 | 0.26494 | 0.022097 | 0.027006 |

| Tissue name | Frequency [Hz] | Conductivity [S/m] | Relative permittivity | Loss tangent | Wavelength [m] | Penetration depth [m] |
|---|---|---|---|---|---|---|
| Oesophagus | 915000000 | 1.1932 | 65.02 | 0.36053 | 0.040007 | 0.036435 |
| Oesophagus | 2450000000 | 2.2105 | 62.158 | 0.26092 | 0.015392 | 0.019092 |

| Tissue name | Frequency [Hz] | Conductivity [S/m] | Relative permittivity | Loss tangent | Wavelength [m] | Penetration depth [m] |
|---|---|---|---|---|---|---|
| Trachea | 915000000 | 0.7757 | 41.971 | 0.36308 | 0.049785 | 0.04504 |
| Trachea | 2450000000 | 1.4488 | 39.733 | 0.26753 | 0.019244 | 0.023299 |

The significance of the change in permittivity of the lung upon inspiration may be of particular interest in a case where the nerve modulation is to be conducted at or below the area of the carina. Once into the right and left bronchi, tissue surrounding the bronchi is increasingly alveolar tissues—highly compliant, and highly air-filled. It is this air that is likely responsible for the decrease in permittivity of filled lungs. The permittivity of air is 1—it does not heat in any significant way in the presence of microwaves.

One significance of this fact for the subject applications is that it may be beneficial to tie the application of microwave energy to the inspiration cycle of respiration, when the lung is filled with air. Alternatively, the method of treatment could include a breath-hold or a ventilatory hold induced by a ventilator machine in order to ensure air-filled tissue surrounding the bronchi supporting the nerves to be treated.

Microwaves encountering materials of different permittivities can also act in unusual ways. Reflections can be created at tissue interfaces or air/tissue interfaces which can be exploited to focus ablative or modulatory energy more specifically on the tissues to be treated.

Figure 48A:
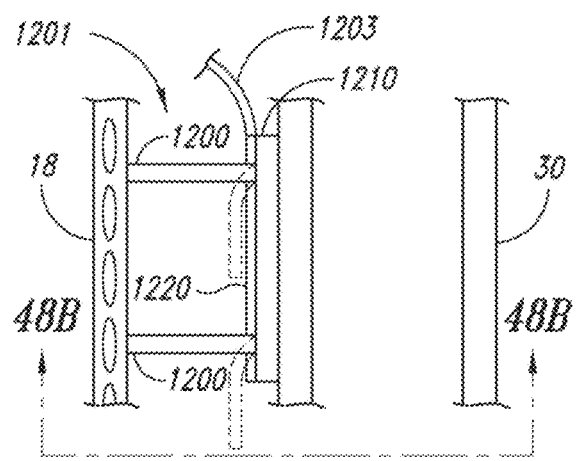
FIG. 48A is a schematic side view of a tracheal device employing a single antenna microwave system.
Figure 48B:
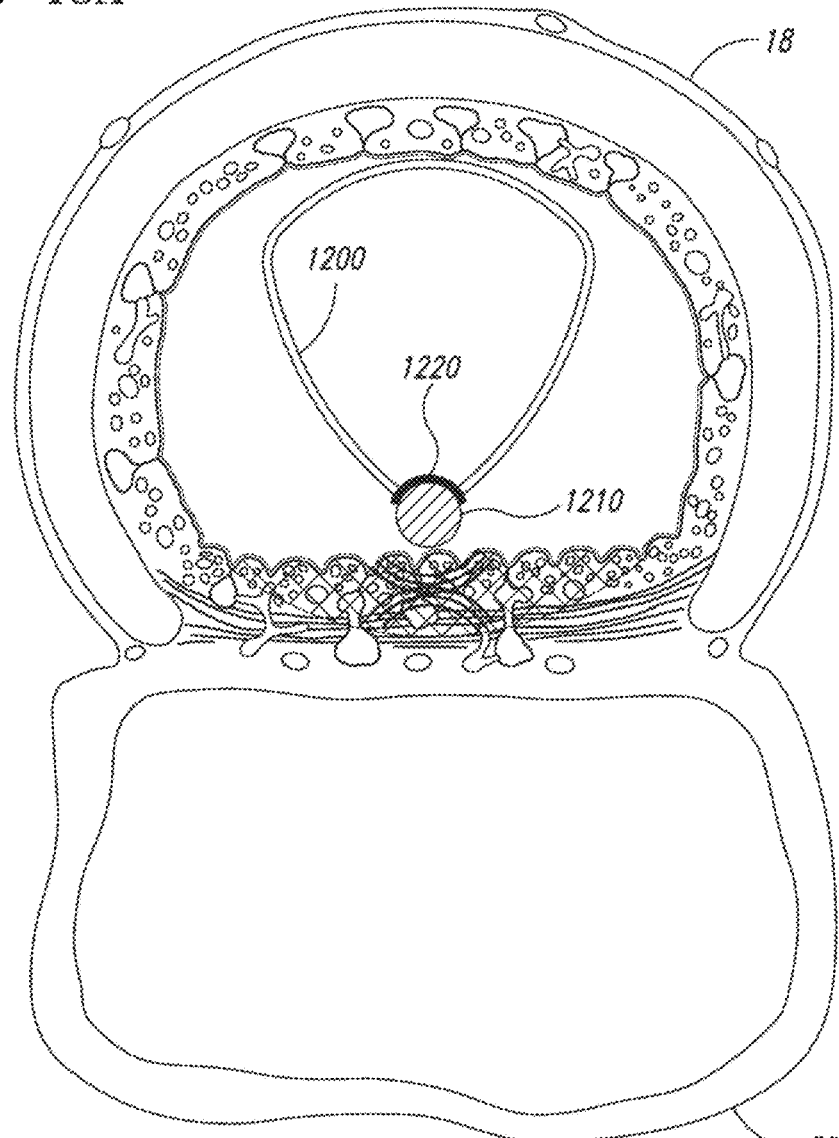
FIG. 48B is a schematic view of the tracheal device of FIG. 48A.

FIGS. 48A and 48B show embodiments of microwave systems. The pulmonary treatment apparatus 1201 includes an elongate member 1203 and a microwave antenna 1210 coupled the elongate member 1203. The microwave antenna 1210 is positioned at treatment location proximate a target site in or proximate to the airway. The microwave antenna 1210 delivers microwave energy so as to alter nerve tissue in a manner which disrupts transmission of nerve signals while non-target tissue disposed between the microwave antenna 1210 and the nerve tissue is not permanently injured.

Expandable or deployable supporting elements 1200 are provided which ensure solid coupling of the antenna 1210 to the tissue. The supporting elements 1200 are movable from a contracted position (shown in dashed line in FIG. 48A) to the illustrated expanded position. These elements can be wires, balloons, fingers, or the like. The supporting elements 1200 of FIGS. 48A and 48B are illustrated as a pair of elongate members 1210 configured to bow outwardly to engage the anterior wall of the airway. Optionally, shielding 1220 can be provided on one or more sides of the device to further focus the microwave energy into the tissue and/or to protect non-target tissues. Shielding 1220 can be metallic foil, metal loaded polymer, metallic mesh with mesh opening of an appropriate fraction of the wavelength in use so as to block transmission of the waves therethrough, or any known microwave shielding material. Not shown in FIGS. 48A and 48B is an optional esophageal protection system. This system can take any of the forms previously disclosed.

Figure 49:
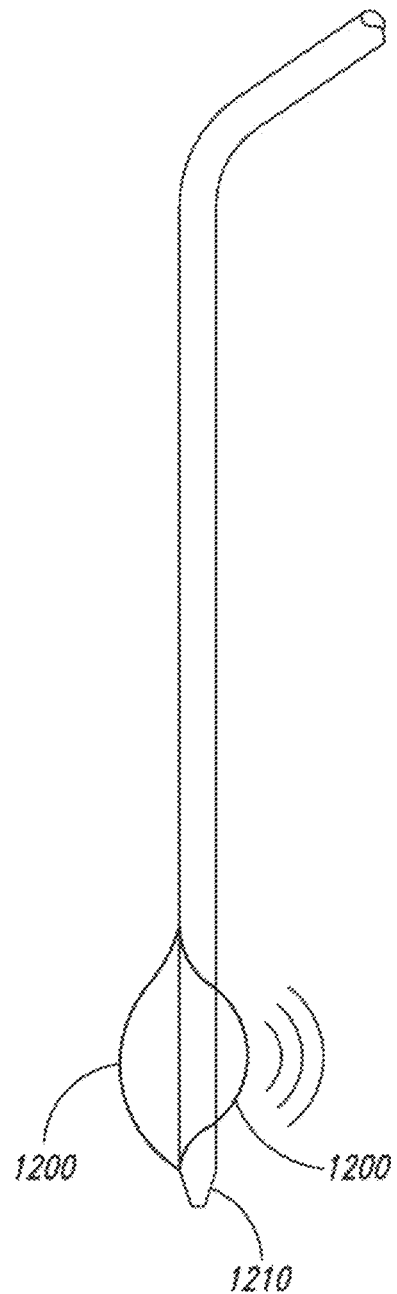
FIG. 49 is a side view of a tracheal device.

Also noted in FIG. 48B is a tissue plane discontinuity between the esophagus and the trachea. If therapy is to be delivered at this level rather than down in the bronchi below the carina, it is possible that the differences in tissue properties will cause reflection, or that the air in the esophagus, or the protectant system in the esophagus, will cause reflection of the microwaves. Reflection of waves can result in cancellation, summation, or additive power of the waves, or it can result in standing waves. Cancellation would tend to negate clinical effectiveness and must be avoided in the system design. Summation or standing waves can be beneficial, and may be designed into the system to provide higher effective energy levels at the target tissue than the level of energy delivered by the system alone. FIG. 49 shows emitted waves.

Figure 50A:
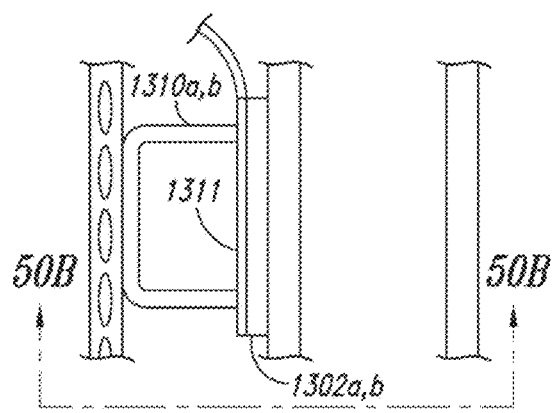
FIG. 50A is a schematic side view of a tracheal device with a dual antenna microwave system.
Figure 50B:
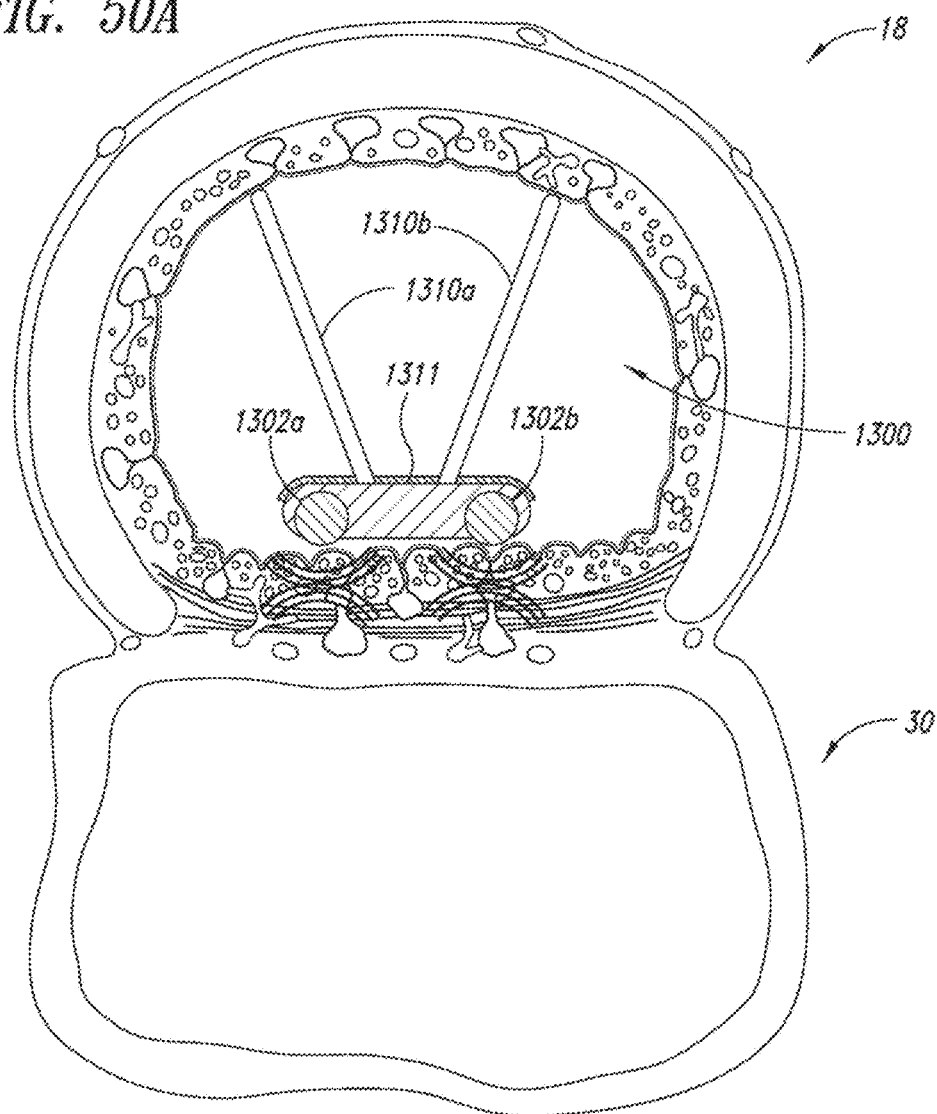
FIG. 50B is a schematic front view of the tracheal device of FIG. 53A.

FIGS. 50A and 50B illustrate a further alternative embodiment of the present invention including a dual antenna system 1300 built on the same basic principles as described in connection with the embodiments disclosed above. A shield of dielectric material 1311 can be mechanically coupled to antennae 1302a, 1302b. Support structures 1310a, 1310b can help hold the antennae 1302a, 1302b proximate or against the posterior tissue of the trachea 18. The support structures 1310a, 1310b can be elongate arms, ribs, inflatable members, or the like. The antennae 1302a, 1302b can cooperate to form standing waves in a desired configuration. Optionally, a protective device can be used to protect tissue of the esophagus 30 or any other bridging tissue proximate or adjacent to the trachea 18 and/or the esophagus 30. Note that while two antennae 1302a, 1302b are shown in this embodiment, any number of antennae can be included without departing from the teachings of the present invention. The antennae may be bound edge-to-edge down the longitudinal axis of the catheters, or they may be separated by an appropriate dielectric material. The antennae 1302a, 1302b can be fired simultaneously, in sequence, alternating or in various other patterns to modify or optimize the SAR distribution to the desired tissue.

Figure 51A:
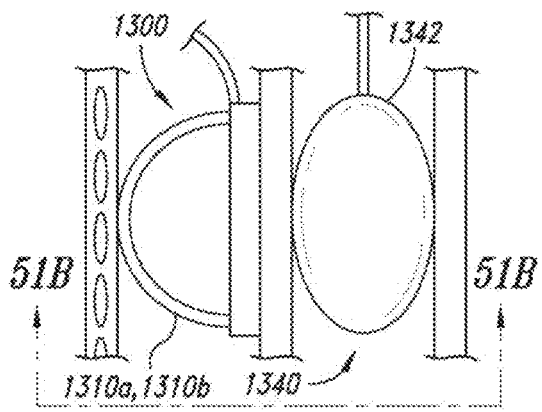
FIG. 51A is a schematic side view of a tracheal device with a dual antenna microwave system and an esophageal reflector/protector.
Figure 51B:
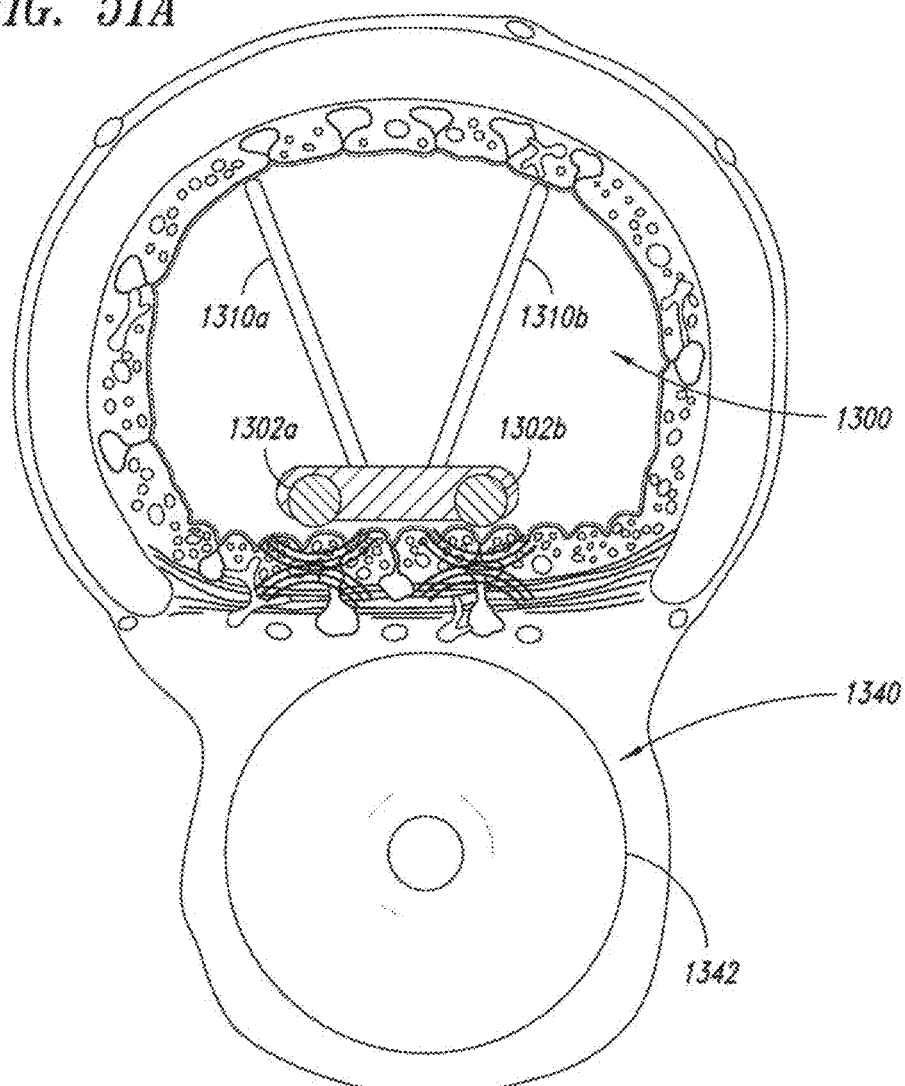
FIG. 51B is a schematic front view of the tracheal device and esophageal reflector/protector device of FIG. 51A.

FIGS. 51A and 51B illustrates yet another embodiment of the microwave therapy system wherein an esophageal device 1340 is included to modify or optimize the microwave SAR pattern in the target tissues. The esophageal device 1340 shown here is a reflector 1342. The reflector 1342 includes a balloon filled with inflation media chosen for specific dielectric properties that alter the SAR pattern in the tissue therebetween. This alteration of the SAR pattern acts to reflect microwave energy back toward the delivering device in order to sum the wave energies or to create a standing wave within the tissue. It could alternatively be used to provide negation of oncoming waves, or it could be used to absorb microwave energy in order to draw the energy deeper into the tissue and then negate it at the device. The balloon 1342 can be connected to the media source. The media source can be the media delivery system 246 discussed in connection with FIG. 10.

While a balloon is shown in the embodiment of FIGS. 51A and 51B, persons of ordinary skill in the art will recognize based on the teachings herein that other devices may be used whose materials, design, use or any combination of these factors provide an alteration to the SAR pattern created by the matched microwave antenna when used in concert with that antenna. Other types of reflectors may include, without limitation, one or more balloons, plates, or the like. Also note that although the microwave embodiment in FIG. 51B is a dual antenna design, any contemplated antenna design could be substituted in this system. Although the use of the dielectric SAR altering device is described with that device in the esophagus and the microwave antenna in the trachea or bronchi, the devices could be placed in the reverse arrangement as desired.

Figure 52A:
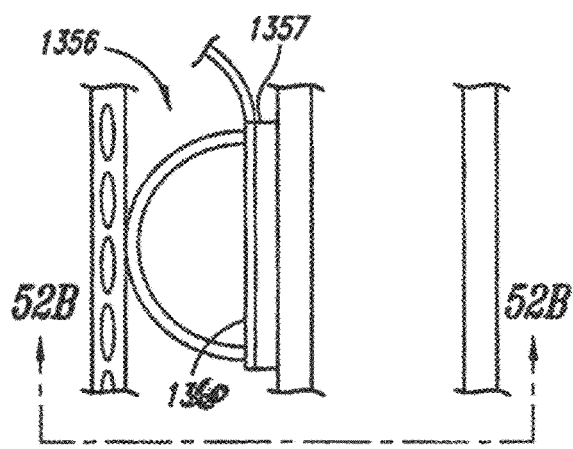
FIG. 52A is a schematic side view of a tracheal device with a microwave device with a cooling or coupling jacket.
Figure 52B:
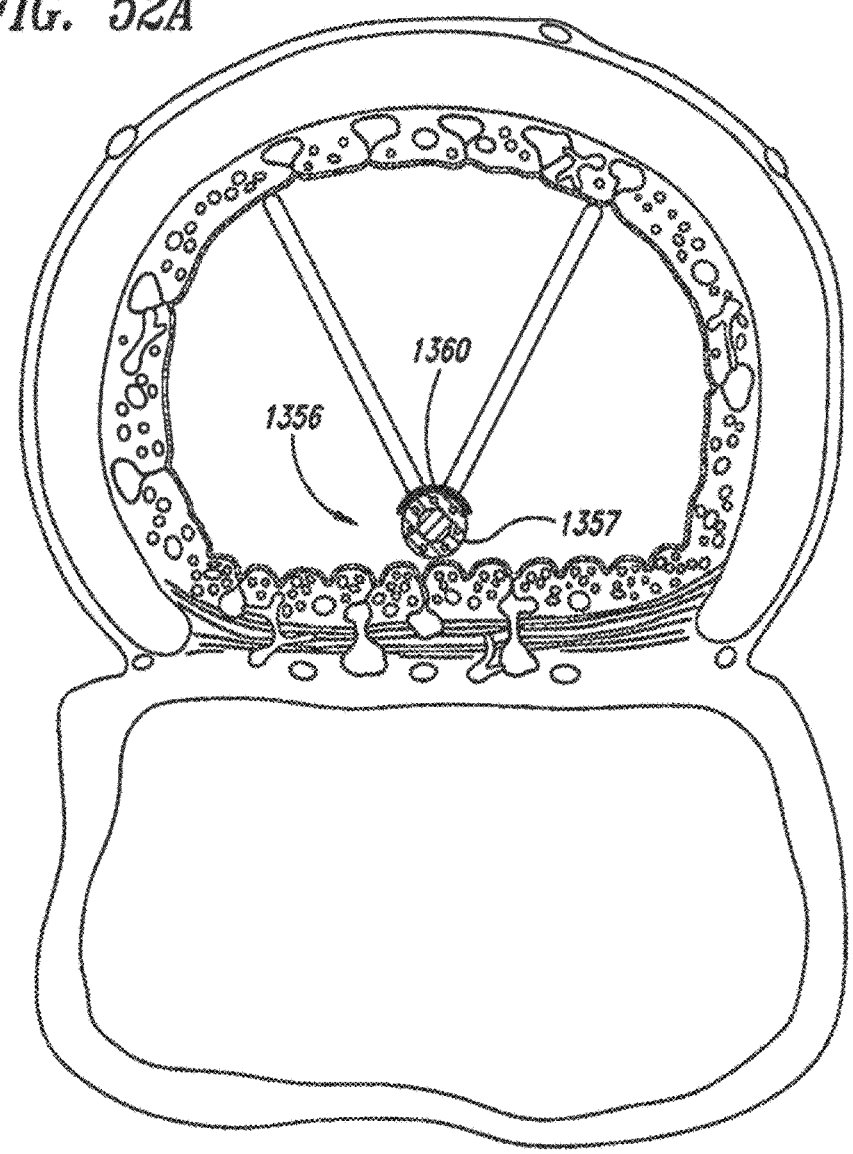
FIG. 52B is a schematic front view of the tracheal device of FIG. 55A.

In another alternative embodiment, as shown in FIGS. 52A and 52B, microwave systems such as those shown in FIGS. 48A-50B can be outfitted with a cooling device in the form of an outer jacket 1356 through which media can be introduced or circulated. A plurality of channels can extend through a main body 1357. This media can serve as a cooling agent via temperature control or flow control of the media, or a combination of the two. The media may be chosen for dielectric properties which provide better coupling between the antenna and the tissue. The outer jacket 1356 may also include shielding 1360.

Figure 53:
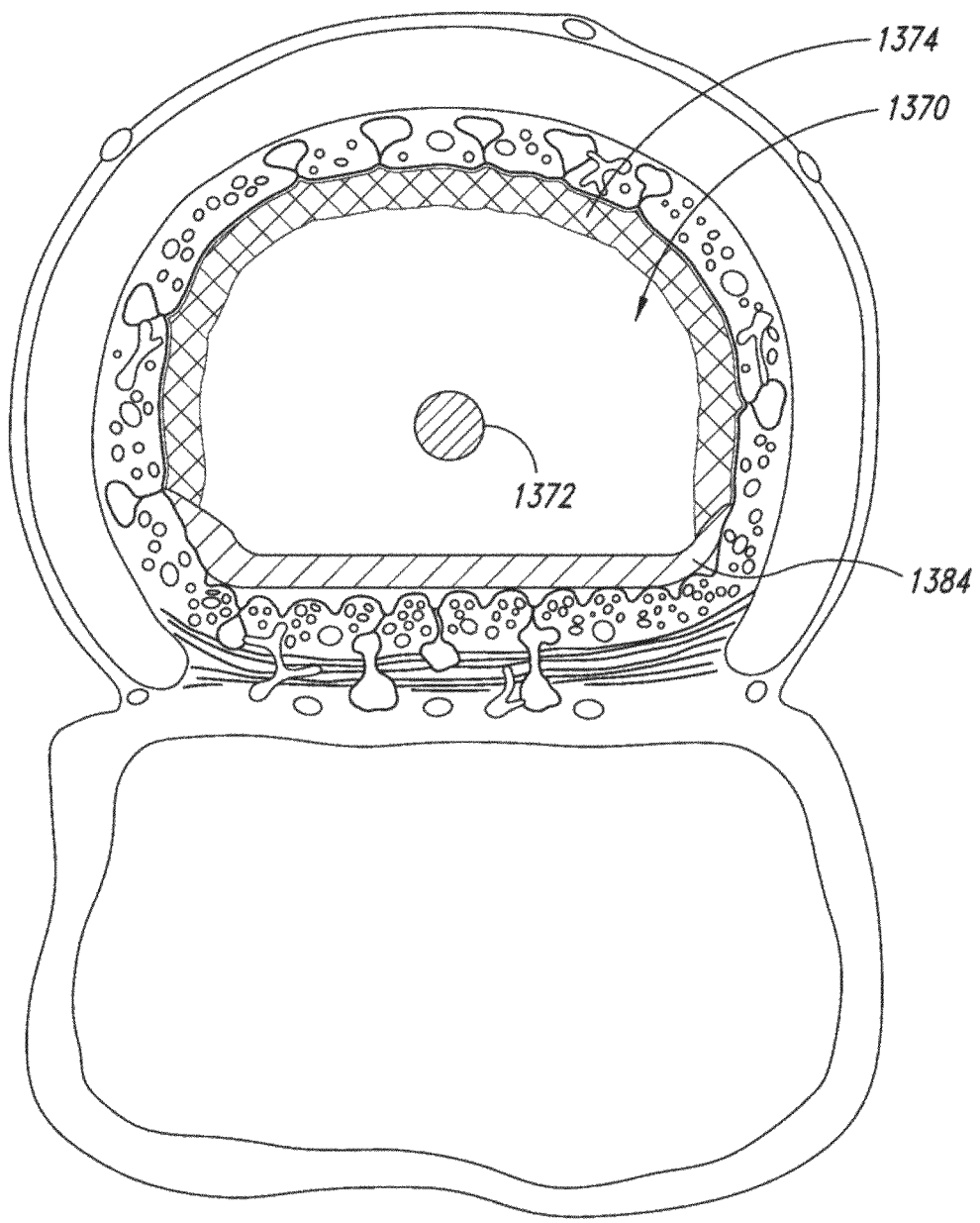
FIG. 53 is a cross-sectional view of a tracheal device positioned within the trachea.

FIG. 53 illustrates another alternative embodiment including cooling or coupling media in a chamber 1370 to surround an antenna 1372. In this embodiment, a cooling device includes an outer member 1374 (illustrated as a balloon wall) of the device that surrounds the antenna 1372 and couples with substantially the entire circumference of the trachea or bronchi. The outer member 1374 cools at least a portion of the non-target tissue while the microwave antenna 1372 delivers the microwave energy. Thus, the wall of the outer member 1374 is positioned between the microwave antenna 1372 and the wall of the airway. The microwave energy can pass through the outer member 1374 and penetrates the airway wall to a depth of the target tissue with an intensity sufficient to alter the tissue. Optionally, shielding 1384 may be built into the device to block transmission on a portion of the circumference to protect that portion from treatment as explained below. In other embodiments, the shielding 1384 can absorb the microwave energy. This shielding could be used to protect the esophagus, for example.

Alternatively, the embodiment of FIG. 53 could be used in a method of treatment for which multiple embodiments throughout this disclosure may be used. To use the device in FIG. 53 with shielding, as an example of a method of treatment according to one embodiment of the present invention, the device would be introduced to a point along the desired treatment zone of the airway. Energy is delivered to a portion of the circumference of the airway which is less than 360 degrees. The device is then advanced or withdrawn so that the next treatment zone either barely overlaps, or allows a small gap between it and the last treatment zone. Additionally, the device is rotated such that there is either a slight overlap or a slight gap circumferentially as compared to the prior treatment site. By repositioning the device both longitudinally and circumferentially, in two or more treatments the entire circumference of the airway could be treated, but not contiguously. In effect, there is a spiral treatment area created, with the proximal and distal ends of the spiral approximately matched or overlapped when compared circumferentially, but which are separated longitudinally.

This spiral or displaced treatment pattern would allow modulation or ablation of the nerves surrounding an airway, without risking the creation of a circumferential zone of treatment which could cause unwanted wall effects such as hyperproliferation of cells during healing, scarring, stenosis or the like.

Another embodiment that would provide the spiral treatment pattern desired would be a multi-slotted antennae 800 as was described in connection with FIG. 47. In addition to the extra slots 811*a*, 811*b*, 811*c*, and hence extra treatment zones spaced longitudinally down a catheter shaft 820, the spiral design may have partial-circumferential shielding (device not shown). FIG. 47 also shows a SAR pattern. The position of the shielding would vary by position along the length of the catheter. For example, a multi-slot design providing four treatment areas longitudinally could be shielded from 12-3 o'clock in longitudinal segment 1, 3-6 o'clock in longitudinal segment 2, 6-9 o'clock in longitudinal segment 3, and 9-12 o'clock in the final longitudinal segment. Thus, it is possible with a single energy application that the entire spiral-shaped energy deposition is made.

Figure 54A:
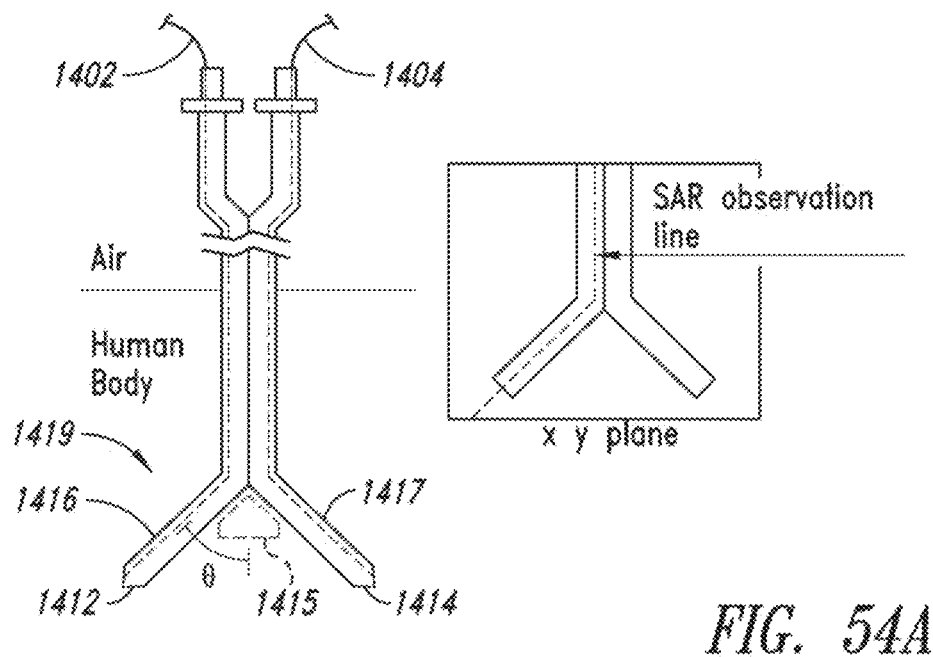
FIG. 54A is a schematic view of an alternative embodiment of the present invention employing a microwave device with a cooling/coupling element.
Figure 54B:
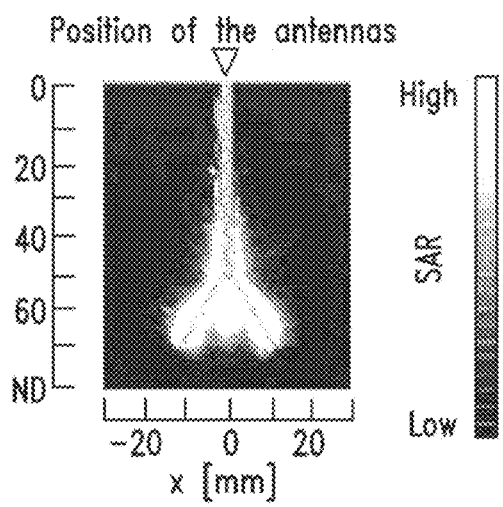
FIG. 54B illustrates a specific absorption rate profile generated by the treatment system of FIG. 54A.
Figure 54C:
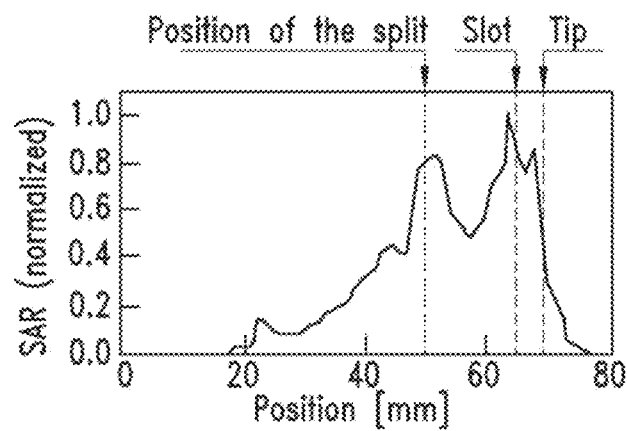
FIG. 54C is a graph of an axial profile along a specific absorption rate observation line.

FIG. 54A shows a further alternative embodiment for a microwave antenna intended to create as large an area of ablation as possible for a given insertion into the body. While the bifurcated shape of the antenna in FIGS. 54A and 54B are interesting for lung applications, several issues make it infeasible to use for this application as shown. Given the rigidity of coaxial cable used in antennae such as that shown in FIGS. 54A and 54B, it may require specific device designs to achieve delivery of such a split tip design to the lung. Pull wires 1402, 1404 attached to the tips 1412, 1414 could be added to deflect the tips 1412, 1414 actively as desired. Memory materials could be built into the shafts of the split segments to bias them outward, and an outer sheath provided to hold them together for delivery. Given the stiffness of some coaxial wire, a wedge-shaped element 1415 (illustrated in dashed line) can be added between legs 1416, 1417 of the split tip 1419, which when retracted via pull wires 1402, 1404 or the like, the legs 1416, 1417 are forced outward and apart.

Additionally, the actual SAR pattern of the antenna shown is not applicable in the pulmonary indication. Note the "tail" of the SAR pattern which extends downward between the legs 1416, 1417 of the device shown in FIG. 54B. This energy deposition would occur in non-target tissues if used in the lung as designed—most probably, the heart.

Significant redesign of the system shown can be performed for pulmonary applications. One embodiment which would provide both the deployment of the legs 1416, 1417 of the split antenna device as well as creating a more desirable SAR pattern would be to provide a sliding wedge element 1415 to separate the legs 1416, 1417, but the material of which is a dielectric material selected to modify the SAR pattern to more closely follow the legs 1416, 1417 of the antennae, without the unwanted "tail" energy directed towards the heart.

High intensity ultrasound (HIFU) is another energy modality that can be employed to provide pulmonary nerve modulation. In HIFU, ultrasound transducers are shaped, or in some cases multiple transducers are electronically beam-formed to a focal point. At the focal point, relatively low intensity ultrasound departs the ultrasound transducer(s) and converges at the focal point designed into the transducer to create a zone of heating and tissue ablation.

A jacketed esophageal HIFU device appears in "US2007/0027445 Method and Apparatus for Noninvasively Treating Patent Foramen Ovale Using High Intensity Focused Ultrasound" by the present inventors, which disclosure is incorporated herein by reference in its entirety. This device is a transesophageal HIFU device coupled to the target tissue with a cooling jacket or balloon surrounding the HIFU elements. This device was initially designed to treat atrial fibrillation by targeting the posterior wall of the heart from the esophagus. However, the same or similar device could be adapted for use in the currently disclosed methods for pulmonary treatment.

HIFU devices are to be used to fire energy into structures which are either tissue or fluid. While reflections of ultrasound may occur at transitions between different tissue types, all of the structures are essentially acoustic conductors. Air, however, will not conduct ultrasound. So in the unique case of pulmonary neuromodulation, HIFU fired from either the airway or esophagus will encounter an air barrier just beyond the target tissue, and become attenuated, or reflect to form a standing wave within the target tissues.

In order to maximize the desired effects, a device similar to the one shown in FIGS. 54A and 54B may be employed wherein the microwave device would be replaced with a HIFU transducer. For HIFU, the dielectric properties of the fluid in the balloon 1342 would be replaced by specific acoustic properties, to either enhance the absorption or reflection of the applied acoustic power.

Figure 55B:
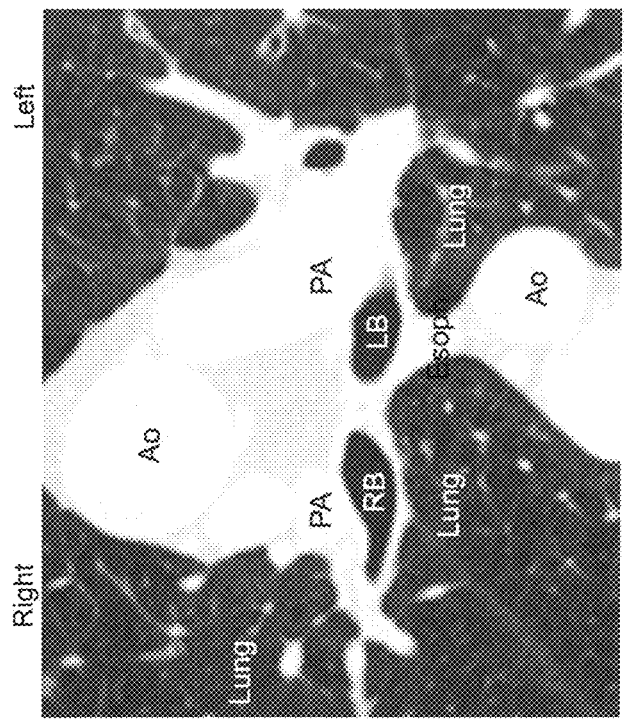
FIG. 55B is a cross-sectional view of FIG. 55A.
Figure 55A:
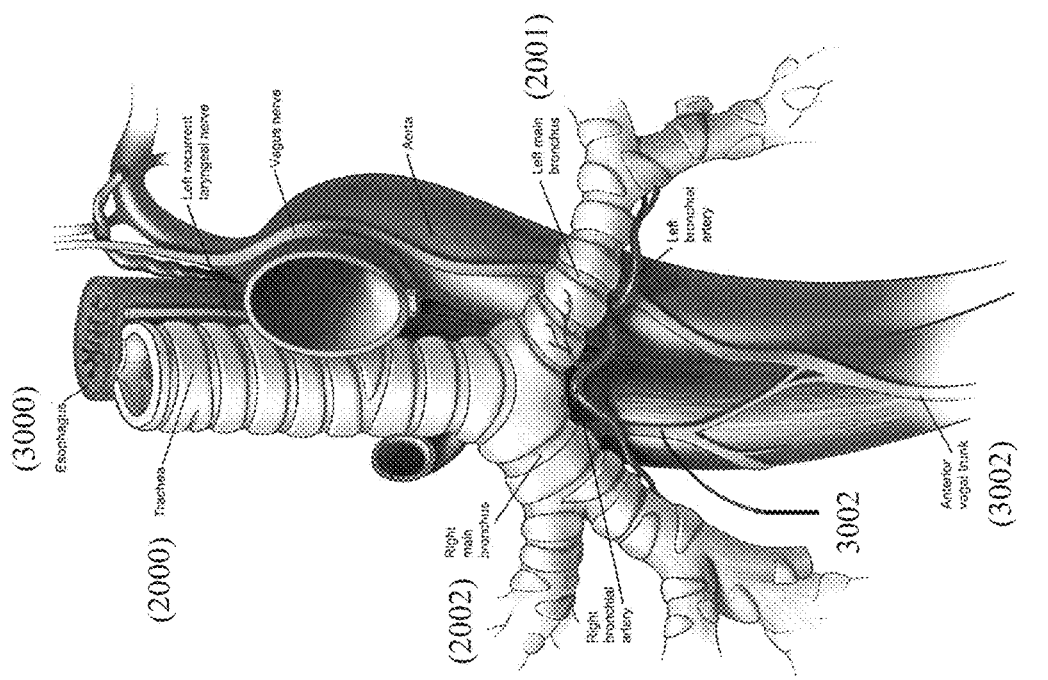
FIG. 55A is an illustration of a portion of a human airway in relation to other anatomical structures.

Referring to FIGS. 55A-55B, a partial representation of a human airway in relation to other anatomical structures is depicted. A trachea 2000 extends downwardly from the nose and mouth and divides into a left main bronchus 2001 and a right main bronchus 2002. The left main bronchus 2001 and right main bronchus 2002 each branch to form lobar, segmental bronchi, and sub-segmental bronchi, which have successively smaller diameters and shorter lengths in the outward direction (i.e., the distal direction). As is apparent from the Figures, trachea 2000 and left main bronchus 2001 are in close proximity to the esophagus 3000 and portions of the vagus nerve 3002 that run along the outside of esophagus 3000.

Referring now generally to FIGS. 56-62, a number of possible approaches are presented to avoid or minimize the risk of injuring esophagus 3000 and branches of the vagus nerve running along esophagus 3000 during pulmonary ablation treatments 5000 (e.g. targeted lung denervation or "TLD"). As used herein, the term "ablation" in the context of pulmonary ablation applications includes sufficiently altering nerve tissue properties to substantially block transmission of electrical signals through the ablated nerve tissue. These approaches include moving the therapy device farther away from the esophagus; reducing the power output of the therapy device, either generally or only when applying energy to a treatment site within the vicinity of the esophagus; cooling the esophagus during pulmonary ablation therapy; monitoring the temperature of the esophagus during pulmonary ablation therapy and halting therapy as necessary to prevent esophageal damage; physically moving the esophagus farther away from the pulmonary treatment site during the pulmonary ablation therapy; avoid delivering pulmonary ablation therapy near the esophagus, either by conducting an imaging procedure prior to the pulmonary ablation therapy, and/or by obtaining imaging at the same time as the pulmonary ablation therapy. One of ordinary skill in the art would appreciate that one or any combination of these approaches can be employed.

Figure 56:
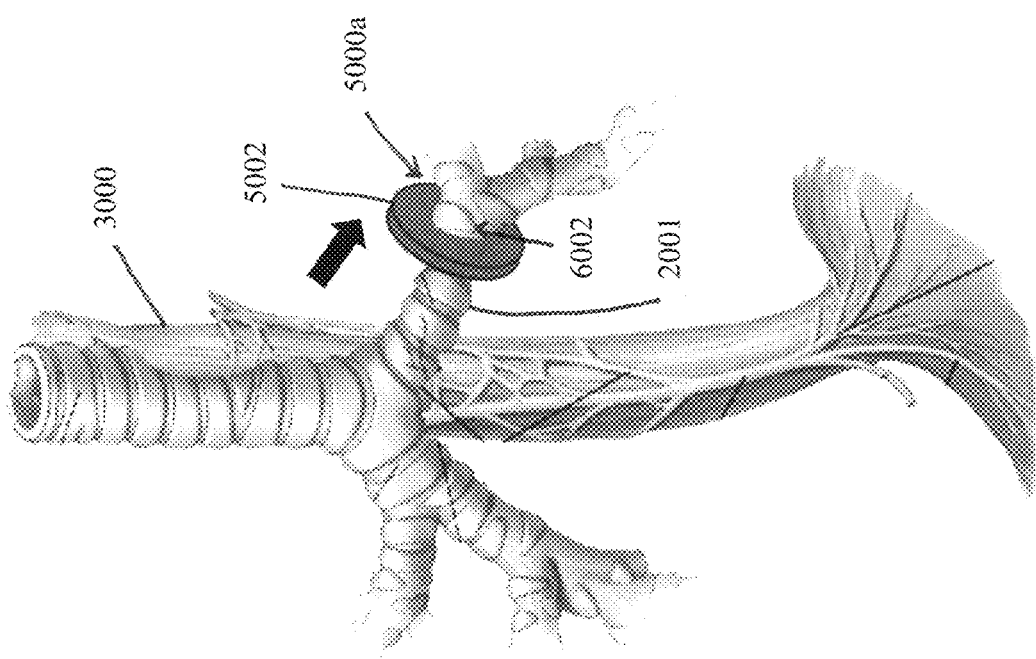
FIG. 56 depicts an approach for treating an airway of a patient according to an embodiment of the invention.

According to an embodiment of the invention, depicted in FIG. 56, pulmonary ablation treatment 5000*b* is delivered as desired, but from a location farther distal from the esophagus 3000. As the left bronchus 2001 extends away from the bifurcation 2003, the separation between left bronchus 2001 and the esophagus 3000 increases, thereby protecting esophagus 3000 and esophageal branches of the vagus nerve 3002 during delivery of pulmonary ablation treatment. Thus, a treatment 5000*b* having a likely range of effect 5002 delivered from a more distal position 6002 will likely avoid damage to the esophagus without having to reduce the amount of energy of treatment 5000*b*. This distal approach is likely to prevent or greatly minimize any damage to esophagus 3000 and esophageal branches of the vagus nerve 3002 during pulmonary ablation treatment in most patients, with no harmful side effects.

Figure 57:
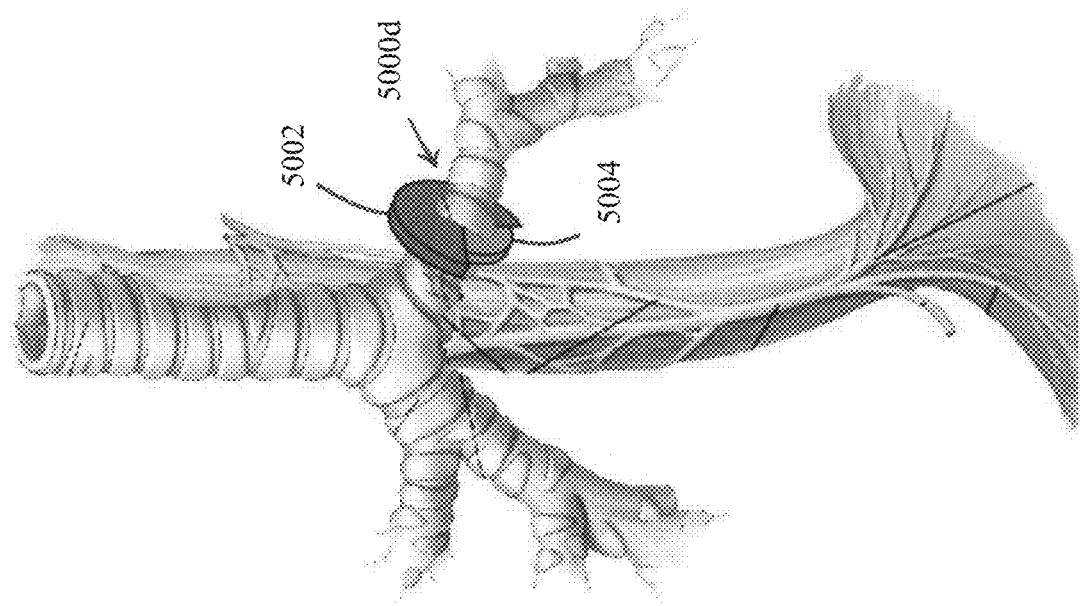
FIG. 57 depicts an approach for treating an airway of a patient according to another embodiment of the invention.

In another approach depicted in FIG. 57, pulmonary ablation treatment 5000*c* is delivered from desired location 6000 proximate esophagus 3000, but the treatment is delivered at a reduced energy level resulting in a reduced likely range of effect 5004. By reducing the energy level, the potential for damage to esophagus 3000 or esophageal branches of the vagus nerve 3002 is lessened. This reduced energy approach is likely to prevent or greatly minimize any damage to esophagus 3000 during pulmonary ablation treatment 5000*c* in most patients, with no harmful side effects. By carefully selecting the power level to be as high as possible while still avoiding esophageal injury, satisfactory procedural efficacy can be achieved.

Figure 58:
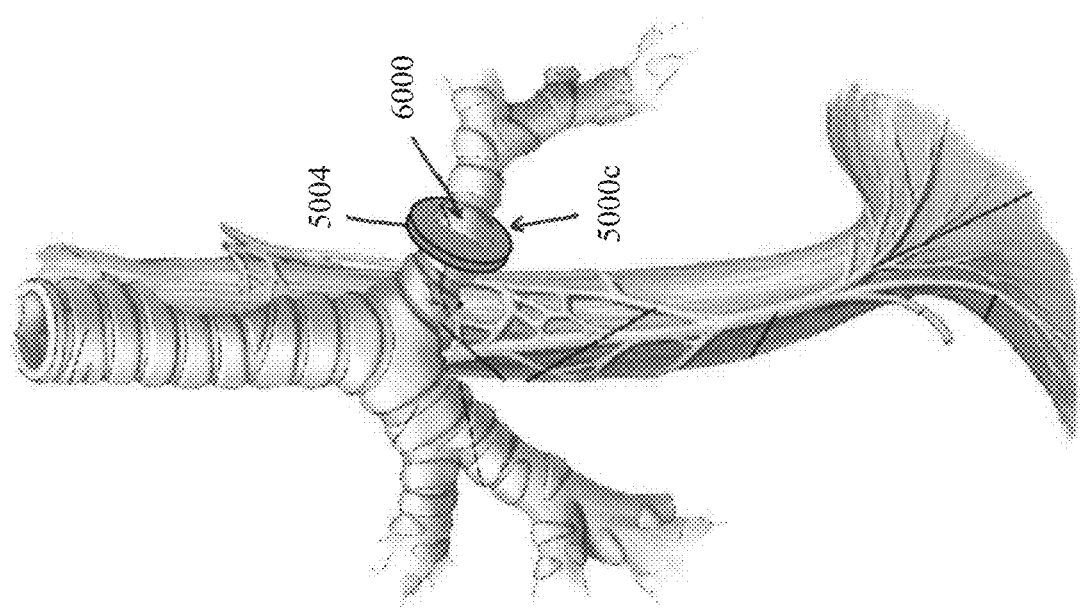
FIG. 58 depicts an approach for treating an airway of a patient according to another embodiment of the invention.

The approach depicted in FIG. 57 may be modified, as depicted in FIG. 58. In the approach depicted in FIG. 58, pulmonary ablation treatment 5000*d* is delivered from desired location 6000 proximate esophagus 3000. In the portion of the circumference of left bronchus 2001 most proximate esophagus 3000, treatment 5000*d* is delivered at a reduced energy level resulting in a reduced likely range of effect 5004. At other portions of the circumference of left bronchus 2001, treatment 5000*d* is delivered at a desired energy level resulting in likely range of effect 5002, as illustrated in FIG. 58. By identifying and limiting the specific region where reduced power is applied, this modified approach avoids damaging esophagus 3000 and esophageal branches 3002 without significant loss of efficacy.

Figure 59:
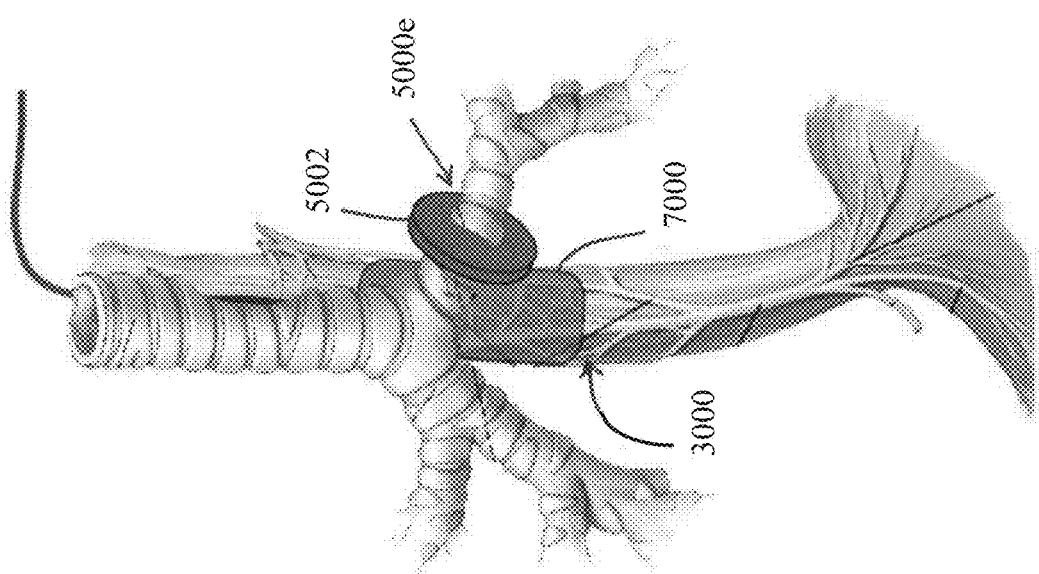
FIG. 59 depicts an approach for treating an airway of a patient according to another embodiment of the invention.

In another approach depicted in FIG. 59, and similar to embodiments described supra, esophagus 3000 is actively cooled during a pulmonary ablation treatment 5000*e*. For example, a cooling balloon 7000 may be introduced into the esophagus and positioned proximate the left bronchus treatment site. Coolant may be circulated through balloon 7000 in order to lower the temperature of tissue within and around the esophagus and the esophageal branches of the vagus nerve. This cooling approach counteracts the potentially damaging heat created by pulmonary ablation treatment 5000*e*, so as to prevent or greatly minimize any damage to esophagus 3000 and the esophageal branches 3002 during pulmonary ablation treatment. Pulmonary treatment 5000e is delivered at a desired energy level and from desired location 6000, resulting in a likely range of effect 5002 without any significant reduction in the efficacy of treatment 5000e.

Figure 60:
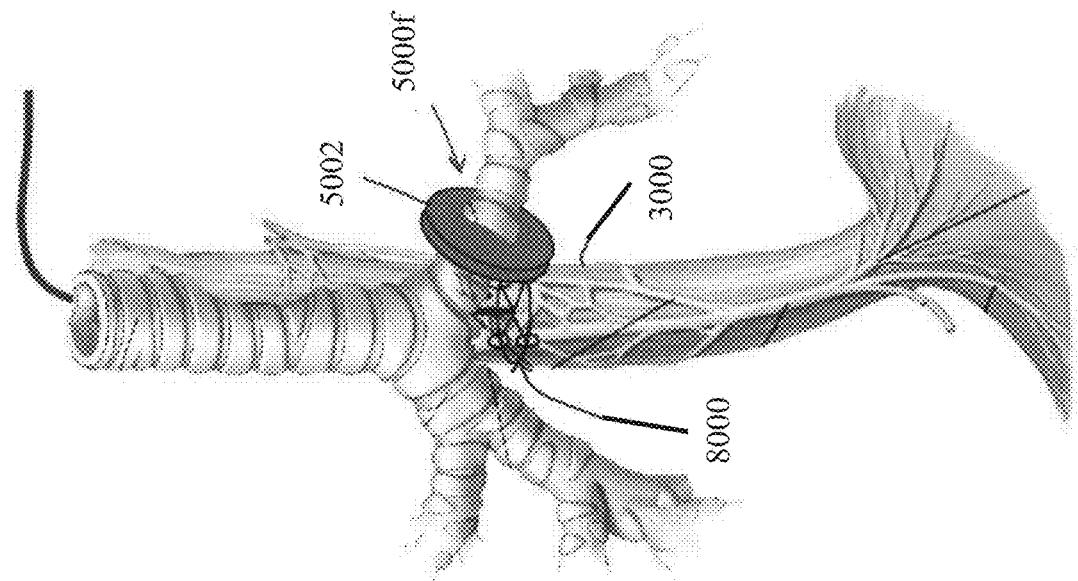
FIG. 60 depicts an approach for treating an airway of a patient according to another embodiment of the invention.

In another approach depicted in FIG. 60, the temperature of esophagus 3000 is monitored during a pulmonary ablation treatment 5000f. As treatment 5000f is delivered at the desired energy level from the desired location 6000 within left bronchus 2001, the temperature of one or more portions of esophagus 3000 and/or surrounding tissue is monitored, such as with the use of a temperature probe 8000 placed in and/or around the esophagus. In the event the observed temperature rises to an unacceptable or undesirable level, pulmonary ablation treatment 5000f may be reduced (e.g. by lowering power output and/or increasing cooling) or altogether halted. This technique may be utilized alone or in combination with any of the other esophageal protection approaches disclosed herein.

Figure 61:
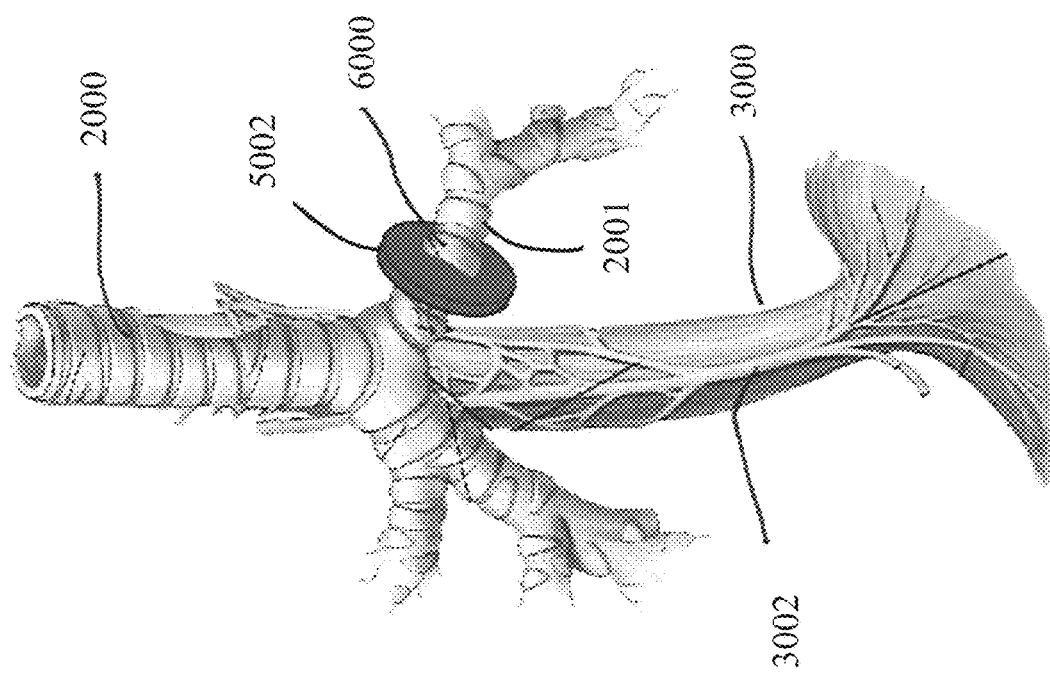
FIG. 61 depicts an approach for treating an airway of a patient according to another embodiment of the invention.

In another approach depicted in FIG. 61, esophagus 3000 may be physically moved during a pulmonary ablation treatment, or during energy deliver at specific pulmonary locations, to a position where esophagus 3000 and esophageal branches are less susceptible to being damaged. An esophagoscope or other suitable instrument such as a rigid or flexible catheter (not shown) may be placed in the esophagus and utilized to temporarily re-position the esophagus 3000 further from a treatment site 5002 (e.g., in left bronchus 2001) of a pulmonary ablation treatment. Esophagus 3000 is typically able to be moved sufficiently to avoid being damaged during the pulmonary ablation treatment, without any harmful consequences to the patient. Following energy delivery, the esophagus is repositioned back to its normal, pre-procedure location. As shown in FIG. 61, esophagus 3000 has been displaced laterally from treatment site 5002 such that it is spaced from left bronchus 2001 and treatment site 5002.

In an alternative embodiment for moving the esophagus (not shown), a minimally invasive procedure is employed in which a device, such as an expandable member (e.g. a balloon catheter), thermal shield (e.g. a foam or heat conductive pad), or other heat sinking, reflective, or protective device, is percutaneously inserted and positioned interstitially between the airway proximate the pulmonary ablation treatment site and the esophagus. The device is positioned to physically lift and/or thermally shield the esophagus from the treatment site. For example, in an embodiment in which the device comprises a balloon catheter, the balloon catheter is deployed, such as by filling with a gas or liquid, thereby lifting the esophagus away from the airway. Optionally, the liquid or gas can be cooled and circulated within the balloon catheter to provide additional protection via cooling of the esophagus. Optionally, a contrast media can be circulated within the balloon for imaging of the catheter. In an alternative embodiment, an expandable member can comprise an expandable basket, or other non-balloon type devices.

In another approach not shown, an imaging procedure is conducted prior to a pulmonary ablation treatment, in order to more accurately determine the position of the esophagus with respect to a desired treatment site. Imaging may be obtained through the use of, for example, a computed tomography (CT) scan, ultrasound, fluoroscopy, x-ray, or other suitable methods. The patient-specific images can then be examined to determine the likelihood a patient will suffer esophageal damage during a pulmonary ablation treatment, and also provide an indication of one or more locations to avoid delivering treatment from. This technique could be used alone or in combination with any of the esophageal protection approaches described elsewhere herein.

In another approach, an imaging procedure is performed in conjunction with a pulmonary ablation treatment, in order to more accurately determine the position of the esophagus with respect to a desired treatment site. Imaging may be obtained through the use of, for example, fluoroscopy or ultrasound, or other suitable methods. The use of real-time imaging provides an accurate indication the position of the esophagus with respect to a desired treatment site, so that the treatment may be modified if needed. For example, when the treatment device or treatment site is in close proximity to the esophagus, as indicated by the real-time imaging procedure, the pulmonary ablation treatment may be delivered at a reduced energy (or power) level, thereby decreasing the potential for damage to the esophagus or esophageal branches of the vagus nerve. Alternately, the delivery of treatment at the reduced level may be limited only to the portion of the circumference of the airway most proximate the esophagus. Alternately, treatment may be suspended when the treatment device is in close proximity to the esophagus, as indicated by the real-time imaging procedure.

Figure 62:
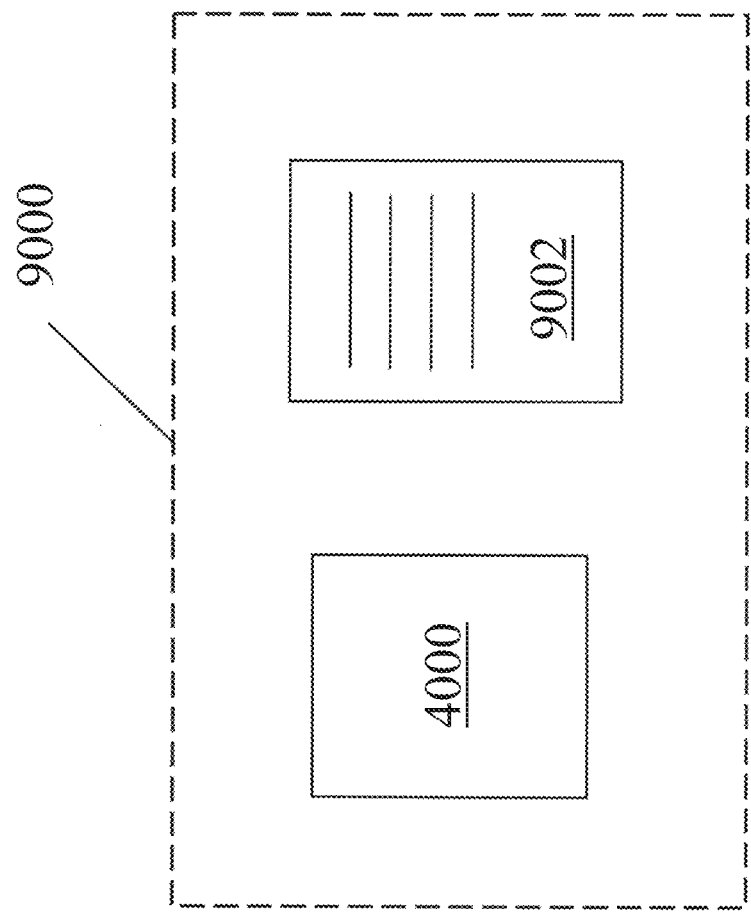
FIG. 62 is a schematic representation of a kit according to an embodiment of the present invention.

In an embodiment depicted in FIG. 62, the present invention comprises a kit 9000 which includes a pulmonary ablation treatment device 4000 and a set of instructions 9002 for using the contents of the kit. Optionally, the kit 9000 includes a device for, or means for, minimizing or preventing damage to an esophagus of a patient during operation of the pulmonary ablation treatment device. For example, kit 9000 can include an intraluminal esophageal catheter, scope or other device for esophageal cooling and/or repositioning. The kit 9000 may be comprised of one or more hermetically sealed and sterilized packages, and the contents of kit 9000 may be provided already assembled as necessary, or the contents may be provided individually and instructions 9002 include the steps of assembling the contents as necessary. Kit 9000 and/or the individual contents of the kit may be provided by causing kit 9000 and/or contents to be manufactured and made available to a user.

The instructions 9002 provided in kit 9000 include instructions for operating the pulmonary ablation treatment device, and instructions for minimizing or preventing damage to an esophagus of a patient during operation of the device according to the various methods described herein. Instructions 9002 may comprise any of a variety of tangible or intangible media including, but not limited to a written manual, a CD or CD-ROM, CD, CD-ROM, DVD, BluRay, digitally downloadable or viewable on onto a personal device, such as a computer, tablet, smart device, and/or via verbal instruction by a provider of kit 9000. In another embodiment, instructions for using the assemblies in accordance with the various embodiments described herein are provided, for example, by a manufacturer or supplier of the assemblies, separately from providing the assemblies, such as by way of information that is accessible using the Internet or by way of seminars, lectures, training sessions or the like.

According to any of the embodiments described above, different types of modifications can be made to treat tissue with different types of energy. Energy can be used to damage target regions. As used herein, the term "energy" is broadly construed to include, without limitation, thermal energy, cryogenic energy (e.g., cooling energy), electrical energy, acoustic energy (e.g., ultrasonic energy), HIFU energy, RF energy, pulsed high voltage energy, mechanical energy, ionizing radiation, optical energy (e.g., light energy), microwave energy, and combinations thereof, as well as other types of energy suitable for treating tissue. In some embodiments, the catheter system, devices, or apparatus disclosed herein delivers energy and one or more substances (e.g., radioactive seeds, radioactive materials, etc.), treatment agents, and the like. For example, the assembly 208 of FIGS. 5 and 6 can include one or more ports through which a treatment agent is delivered. Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, or combinations thereof. For example, long acting or short acting nerve blocking drugs (e.g., anticholinergics) can be delivered to the nerve tissue to temporarily or permanently attenuate signal transmission. Substances can also be delivered to chemically damage the nerve tissue. The electrodes, antenna, or other energy emitting components can be replaced with other types of components based on the desired type of energy to be used for treatment.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

What is claimed is:

1. A method of treating one or more pulmonary diseases while minimizing or preventing damage to an esophagus and esophageal branches of the vagus nerve of a subject, the method comprising:
    inserting an elongate member through at least a portion of a trachea, the elongate member having an energy delivery element coupled to a distal end;
    positioning the energy delivery element in the airway and proximate a treatment site in or along the airway;
    delivering radiofrequency (RF) energy from an active portion of the energy delivery element positioned within the airway to ablate nerve tissue at the treatment site to attenuate nervous system signals transmitted to a portion of the bronchial tree to reduce airway constriction in the subject;
    simultaneously while delivering RF energy, protecting the esophagus and esophageal branches of the vagus nerve outside of the airway to prevent or inhibit permanent damage to the esophagus and/or surrounding tissue proximate or adjacent to the esophagus by at least one of moving the esophagus away from the treatment site, reducing a power level to the active portion of the energy delivery element, and dissipating or removing heat from the esophagus and/or surrounding tissue proximate or adjacent to the esophagus; and
    simultaneously while delivering RF energy, protecting tissue between the treatment site and the active portion of the energy delivery element by cooling the energy delivery element.

2. The method of claim 1, wherein delivering RF energy while simultaneously protecting the esophagus and esophageal branches of the vagus nerve comprises:
    delivering RF energy at a first power level from the active portion of the energy delivery element to the treatment site to create a first lesion covering a first portion of a circumference of the airway;
    moving the energy delivery element; and
    delivering RF energy at a second power level from the active portion of the energy delivery element to the treatment site to create a second lesion covering a second portion of the circumference of the airway displaced from the first portion and positioned in closer proximity to the esophagus than the first portion;
    wherein the first power level is substantially greater than the second power level.

3. The method of claim 1, wherein delivering RF energy while simultaneously protecting the esophagus and esophageal branches of the vagus nerve comprises:
    delivering RF energy at a first power level from the active portion of the energy delivery element to the treatment site to create a first lesion covering a first portion of a circumference of the airway, wherein the first portion is located at a distance from the esophagus such that minimal or no permanent damage to the esophagus and esophageal branches of the vagus nerve occurs during delivery of energy to the first portion; and
    delivering no energy to a second portion of the circumference of the airway displaced from the first portion and positioned in closer proximity to the esophagus than the first portion.

4. The method of claim 1, wherein positioning the energy delivery element coupled to the elongate member proximate a treatment site in an airway comprises positioning the energy delivery element in one of the left or right main bronchus distal from a bifurcation of the left and right bronchus such that minimal or no permanent damage to the esophagus and esophageal branches of the vagus nerve occurs during delivery of RF energy to the treatment site.

5. The method of claim 1, wherein delivering RF energy while simultaneously protecting the esophagus and esophageal branches of the vagus nerve comprises:
    monitoring a temperature of one or more portions of the esophagus and/or surrounding tissue during RF energy delivery; and reducing or halting RF energy delivery if an observed temperature rises to or beyond a predetermined threshold temperature level.

6. The method of claim 5, wherein the temperature is monitored by placing one or more temperature probes in or around the esophagus.

7. The method of claim 1, wherein protecting the esophagus and esophageal branches of the vagus nerve comprises:
before energy delivery, moving the esophagus from a first position proximate the treatment site, to a second position distal the treatment site; and
after energy delivery, moving the esophagus from the second position back to the first position.

8. The method of claim 7, wherein moving the esophagus from the first position to the second position comprises:
providing an expandable member expandable between a retracted configuration and an expanded configuration;
percutaneously inserting the expandable member in the retracted configuration between the esophagus and the airway; and
at least partly expanding the expandable member to shift the esophagus from the first position to the second position.

9. The method of claim 8, further comprising:
circulating a coolant through the expandable member during energy delivery to cool or remove heat from the esophagus and/or tissue surrounding the esophagus.

10. The method of claim 7, wherein moving the esophagus from the second position to the first position comprises:
deflating or retracting the expandable member; and
removing the expandable member.

11. The method of claim 1, wherein protecting the esophagus and esophageal branches of the vagus nerve comprises:
before energy delivery, percutaneously introducing a heat shielding or heat dissipating member between the esophagus and the airway proximate the treatment site.

12. The method of claim 1, wherein the active portion of the energy delivery element comprises at least one electrode, and wherein delivering radiofrequency (RF) energy while simultaneously protecting the esophagus and esophageal branches of the vagus nerve comprises delivering RF energy to the treatment site while dissipating and/or removing heat from the esophagus and/or the surrounding tissues of the esophagus.

* * * * *